United States Patent [19]

Kamiya et al.

[11] 4,181,800

[45] Jan. 1, 1980

[54] 2-AZETIDINONE COMPOUNDS AND PROCESSES FOR PREPARATION THEREOF

[75] Inventors: Takashi Kamiya, Suita; Masashi Hashimoto, Toyonaka; Osamu Nakaguti; Teruo Oku, both of Osaka; Yoshiharu Nakai, Otsu; Hidekazu Takeno, Nara, all of Japan

[73] Assignee: Fujisawa Pharmaceutical Co., Ltd., Osaka, Japan

[21] Appl. No.: 730,012

[22] Filed: Oct. 6, 1976

[30] Foreign Application Priority Data

Oct. 6, 1975 [GB] United Kingdom ............... 40893/75
Jan. 2, 1976 [GB] United Kingdom ..................... 94/76
Jan. 5, 1976 [GB] United Kingdom ................... 242/76
May 25, 1976 [GB] United Kingdom ............... 21507/76
Jun. 21, 1976 [GB] United Kingdom ............... 25746/76

[51] Int. Cl.$^2$ ....................... C07D 251/00; A01N 9/00
[52] U.S. Cl. ...................................... 544/180; 424/249
[58] Field of Search ................... 260/248 NS; 544/180

[56] References Cited

U.S. PATENT DOCUMENTS 3,538,092  11/1970  Dexter ........................... 260/248 NS

*Primary Examiner*—Alan Siegel
*Attorney, Agent, or Firm*—Dayton R. Stemple, Jr.

[57] ABSTRACT

This invention relates to new 2-azetidinone compounds, which have antimicrobial activities, and to processes for the preparation thereof, and more particularly, this invention provides new 2-azetidinone compounds, especially ones having various substituted carboxyalkyl radicals at the first position and having various groups at the fourth position of the azetidinone nucleus, which have antimicrobial activities against various pathogenic microorganisms and are useful as antibiotics in treatment for microbial infections in mammal including human being and animals.

35 Claims, No Drawings

2-AZETIDINONE COMPOUNDS AND PROCESSES FOR PREPARATION THEREOF

Only for the purpose of illustrating the state of the arts, the following known compounds are exemplified.

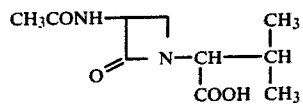

(Tetrahedron, Vol. 23, p. 4769, 1967)

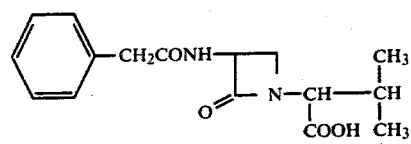

(Tetrahedron, Vol. 23, p. 4769, 1967)

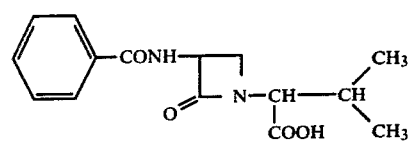

(Tetrahedron, Vol. 23, p. 4769, 1967)

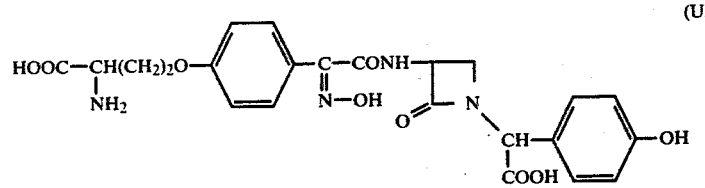

(U.S.P.3923.977)

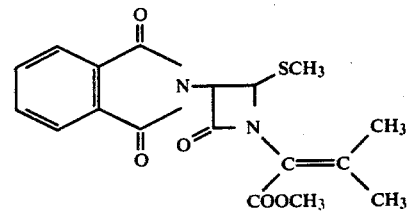

(Tetrahedron Letters, No.9. P725-728)

These above known compounds, however, scarecely possess antimicrobial activity against pathogenic microorganism, or possess antimicrobial activity against only a specific Gram-negative bacteria, *Pseudomonas aeruginosa*.

Accordingly, it is one object of this invention to provide new 2- azetidinone compounds which have antimicrobial activity against Gram-positive and Gram-negative bacteria.

Another object of this invention is to provide processes for preparing new azetidinone compounds.

The object compound of this invention, 2-azetidinone compounds, is represented by the following formula:

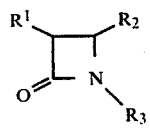

wherein
$R^1$ is amino, substituted amino, substituted hydroxy, azido, halogen,
$R^2$ is hydrogen, hydroxymethyl, aralkoxyiminomethyl, aryl, aralkenyl, formyl, carboxy or a residue of nucleophile, and
$R^3$ is a group of the formula:

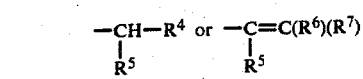

in which $R^4$ is aryl, aralkyl, arylthioalkyl or a heterocyclic group,
$R^5$ is carboxy or its derivative,
$R^6$ is alkyl, haloalkyl, arylthio or heterocyclic-thioalkyl and
$R^7$ is hydrogen, haloalkyl or heterocyclic-thioalkyl.
provided that,
when $R^1$ is amino or acylamino whose acyl moiety is derived from an organic carboxylic or an organic sulfonic acid, and $R^2$ is hydrogen,
$R^3$ is a group represented by the formula:

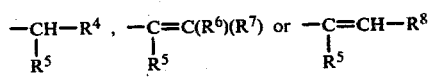

in which
$R^4$ is phenyl bearing N-substituted or unsubstituted alkanesulfonamido, or aroylalkoxy, naphthyl, aralkyl, arylthioalkyl or a heterocyclic group,
$R^6$ is alkyl, haloalkyl or heterocyclic-thioalkyl,
$R^7$ is haloalkyl or heterocyclic-thioalkyl,
$R^8$ is arylthio and
$R^5$ is as defined above, and
when
$R^1$ is amino, substituted amino or azido and $R^2$ is aryl or a residue of nucleophile selected from halogen or a residue of S-nucleophile, $R^3$ is a group represented by the formula:

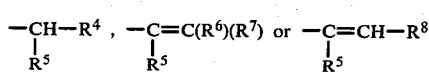

in which
- $R^4$ is aryl, aralkyl, arylthioalkyl or a heterocyclic group,
- $R^6$ is alkyl or heterocyclic-thioalkyl,
- $R^7$ is heterocyclic-thioalkyl,
- $R^8$ is arylthio and
- $R^5$ is as defined above, and in the definitions of the above groups, the alkane, arene and heterocycle moieties may have possible substituent.

With regard to the object compound of the above formula (I), it is to be understood that there may be one or more stereoisomeric pair(s) such as optical and/or geometric isomers being due to the presence of asymmetric carbon atom(s) and/or double bond(s) in that molecule, and these isomers are also included within the scope of the object compound (I).

The reaction schemes of the Processes for the preparation of the object compound of this invention According to this invention, the object compound (I) can be prepared by processes, which are illustrated by the following schemes for a convenience sake, and among these processes, it is to be understood that the Processes 1 to 10 are each fundamental ones and the remainings are modified or alternative ones.

(1) Process 1:

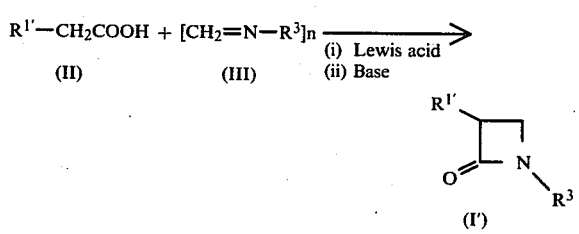

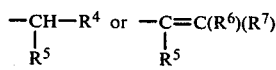

wherein
n is one, two or three,
$R^{1'}$ is substituted amino, substituted hydroxy, azido or halogen,
$R^3$ is a group of the formula:

$$-\underset{R^5}{\overset{|}{C}}H-R^4 \quad \text{or} \quad -\underset{R^5}{\overset{|}{C}}=C(R^6)(R^7)$$

in which
- $R^4$ is aryl, aralkyl, arylthioalkyl or a heterocyclic group,
- $R^5$ is carboxy or its derivative,
- $R^6$ is alkyl, haloalkyl, heterocyclic-thioalkyl or arylthio and
- $R^7$ is hydrogen, haloalkyl or heterecyclic-thioalkyl, provided that,
when $R^{1'}$ is acylamino whose acyl moiety is derived from an organic carboxylic or organic sulfonic acid, and $R^2$ is hydrogen,
$R^3$ is a group of the formula:

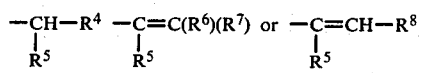

in which
- $R^4$ is phenyl bearing N-substituted or unsubstituted alkanesulfonamido, or aroylalkoxy, naphthyl, aralkyl, arylthioalkyl, heterocyclic group,
- $R^6$ is alkyl, haloalkyl or heterocyclic-thioalkyl,
- $R^7$ is haloalkyl or heterocyclic-thioalkyl,
- $R^8$ is arylthio and
- $R^5$ is as defined above, and when $R^{1'}$ is substituted amino or azido and $R^2$ is aryl or a residue of nucleophile selected from halogen and a residue of s-nucleophile,
$R^3$ is a group of the formula:

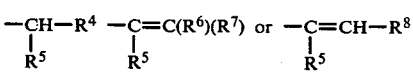

in which
- $R^4$ is aryl, aralkyl, arylthioalkyl or a heterocyclic group,
- $R^6$ is alkyl or heterocyclic-thioalkyl,
- $R^7$ is heterocyclic-thioalkyl,
- $R^8$ is arylthio and
- $R^5$ is as defined above.

(2) Process 2:

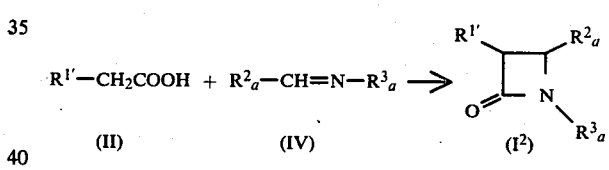

wherein
$R^{1'}$ is protected amino, substituted hydroxy, azido or halogen,
$R_a^2$ is aryl, aralkenyl or a residue of nucleophile and
$R_a^3$ is a group of the formula:

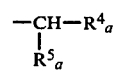

in which
- $R_a^4$ is aryl and
- $R_a^5$ is carboxy or its derivative.

(3) Process 3:

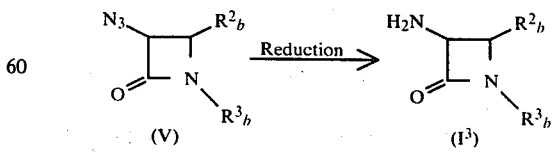

wherein
$R_b^2$ is hydrogen, hydroxymethyl, aryl, aralkenyl, or a residue of nucleophile, and
$R_b^3$ is a group of the formula:

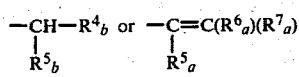

in which
R$_b^4$ is aryl, aralkyl, arylthioalkyl or a heterocyclic group,
R$_b^5$ is carboxy or its derivative, or alkyl having carboxy or its derivative,
R$_a^6$ is alkyl, haloalkyl, arylthio or heterocyclic-thioalkyl,
R$_a^7$ is hydrogen, haloalkyl or heterocyclic-thioalkyl and
R$_a^5$ is as defined above.

(4) Process 4:

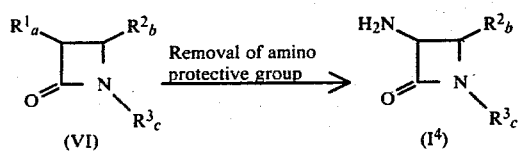

wherein
R$_a^1$ is protected amino,
R$_c^3$ is a group of the formula:

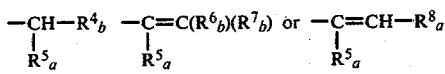

in which
R$_b^6$ is alkyl haloalkyl or heterocyclic-thioalkyl,
R$_b^7$ is haloalkyl or heterocyclic-thioalkyl,
R$_a^8$ is arylthio and
R$_b^4$ and R$_a^5$ are each as defined before, and
R$_b^2$ is as defined before,
provided that, when R$_b^2$ is hydrogen,
R$_c^3$ is a group of the formula:

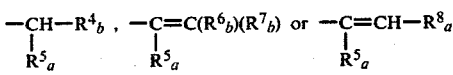

wherein
R$_b^4$ is phenyl bearing N-substituted or unsubstituted alkanesulfonamido, or aroylalkoxy, naphthyl, aralkyl, arylthioalkyl or a heterocyclic group, and
R$_a^5$, R$_b^6$, R$_b^7$ and R$_a^8$ are each as defined before.

(5) Process 5:

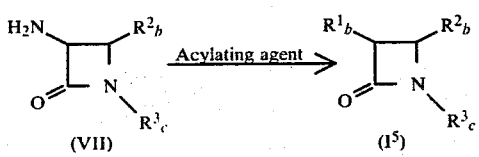

wherein
R$_b^1$ is acylamino, and
R$_b^2$ and R$_c^3$ are each as defined before,
provided that, when R$_b^2$ is hydrogen,
R$_c^3$ is a group of the formula:

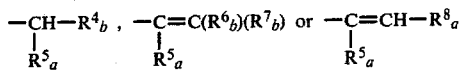

in which
R$_b^4$ is phenyl bearing N-substituted or unsubstituted alkanesulfonamido, or aroylalkoxy, naphthyl, aralkyl, arylthioalkyl or a heterocyclic group, and
R$_a^5$, R$_b^6$, R$_b^7$ and R$_a^8$ are each as defined before.

(6) Process 6:

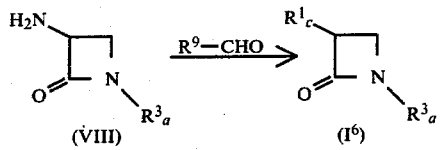

wherein
R$_c^1$ is dialkylamino-methyleneamino or aralkylidene amino,
R$^9$ is dialkylamino or aryl and
R$_a^3$ is as defined before.

(7) Process 7:

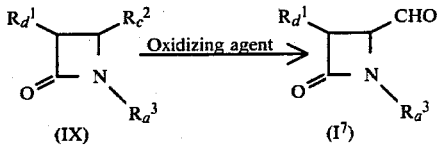

wherein
R$_d^1$ is acylamino or azido,
R$_c^2$ is a group of the formula:

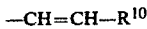

$$-CH=CH-R^{10}$$

in which R$^{10}$ is aryl and
R$_a^3$ is as defined before.

(8) Process 8:

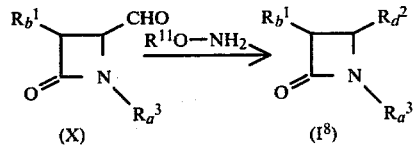

wherein
R$^{11}$ is aralkyl,
R$_d^2$ is a group of the formula:

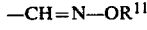

$$-CH=N-OR^{11}$$

in which R$^{11}$ is as defined above, and
R$_b^1$ and R$_a^3$ are each as defined before.

(9) Process 9:

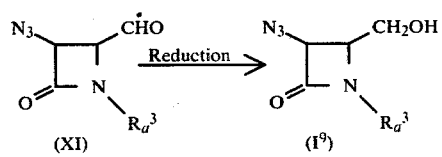

wherein R$_a^3$ is as defined before.

(10) Process 10:

[Structure XII] → (Oxidizing agent) → [Structure I^10]

wherein $R_b^1$ and $R_a^3$ are each as defined before.

(11) Process 11:

[Structure XIII] → (Cyclization) → [Structure I^11]

wherein
$R_e^1$ is aralkylamino, azido or halogen and
$R_c^3$ is as defined above.

(12) Process 12:

[Structure XIV] → (Removal of amino, hydroxy and/or carboxy protective group) → [Structure I^12]

wherein
$R_f^1$ is acylamino having at least one functional group selected from protected amino, protected hydroxy and protected carboxy,
$R_g^1$ is acylamino having at least one functional group selected from amino, hydroxy and carboxy, and
$R_d^3$ is a group of the formula:

$$-\underset{R_a^5}{\underset{|}{CH}}-R_c^4, \quad -\underset{R_a^5}{\underset{|}{C}}=C(R_b^6)(R_b^7) \text{ or } -\underset{R_a^5}{\underset{|}{C}}=CH-R_a^8$$

in which
$R_c^4$ is phenyl bearing N-substituted or unsubstituted alkanesulfonamido, or aroylalkoxy, naphthyl, aralkyl, arylthioalkyl or a heterocyclic group, and
$R_a^5$, $R_b^6$, $R_b^7$ and $R_a^8$ are each as defined above.

(13) Process 13:

[Structure XV] → (Removal of carboxy protective group) → [Structure I^13]

wherein
$R_e^3$ is a group of the formula:

$$-\underset{R_c^5}{\underset{|}{CH}}-R_b^4, \quad -\underset{R_c^5}{\underset{|}{C}}=C(R_b^6)(R_b^7) \text{ or } -\underset{R_c^5}{\underset{|}{C}}=CH-R_a^8,$$

in which
$R_c^5$ is esterified carboxy, and
$R_b^4$, $R_b^6$, $R_b^7$ and $R_a^8$ are each as defined before,
$R_f^3$ is a group of the formula:

$$-\underset{COOM}{\underset{|}{CH}}-R_b^4, \quad -\underset{COOM}{\underset{|}{C}}=C(R_b^6)(R_b^7) \text{ or } -\underset{COOM}{\underset{|}{C}}=CH-R_a^8$$

in which M is hydrogen, or organic or inorganic cation, and
$R^1$, $R_b^2$, $R_b^4$, $R_b^6$, $R_b^7$ and $R_a^8$ are each as defined before, provided that, when $R_b^2$ is hydrogen,
$R_e^3$ is a group of the formula:

$$-\underset{R_c^5}{\underset{|}{CH}}-R_b^4, \quad -\underset{R_c^5}{\underset{|}{C}}=C(R_b^6)(R_b^7) \text{ or } -\underset{R_c^5}{\underset{|}{C}}=CH-R_a^8$$

in which
$R_b^4$ is phenyl bearing N-substituted or unsubstituted alkanesulfonamido or aroylalkoxy, and
$R_c^5$, $R_b^6$, $R_b^7$ and $R_a^8$ are each as defined before, and
$R_f^3$ is a group of the formula:

$$-\underset{COOM}{\underset{|}{CH}}-R_b^4, \quad -\underset{COOM}{\underset{|}{C}}=C(R_b^6)(R_b^7) \text{ or } -\underset{COOM}{\underset{|}{C}}=CH-R_a^8$$

in which
$R_b^4$ is phenyl bearing N-substituted or unsubstituted alkanesulfonamido or aroylalkoxy, and
$R_b^6$, $R_b^7$, $R_a^8$ and M are each as defined before.

(14) Process 14:

[Structure XVI] → (Removal of amino, hydroxy and/or carboxy protective group) → [Structure I^14]

wherein $R_g^3$ is a group of the formula:

$$-\underset{R_a^5}{\underset{|}{CH}}-R_d^4$$

in which
$R_d^4$ is aralkyl having at least one functional group selected from protected amino, protected hydroxy and protected carboxy and
$R_a^5$ is as defined before,
$R_h^3$ is a group of the formula:

$$-\underset{R_a^5}{\underset{|}{CH}}-R_e^4.$$

in which
R$_e$⁴ is aralkyl having at least one functional group selected from amino, hydroxy and carboxy, and
R$_a$⁵ is as defined before, and
R¹ is as defined before.

(15) Process 15:

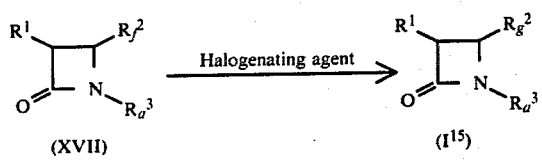

wherein
R$_f$² is a residue of nucleophile selected from alkylthio, aralkylthio, arylthio and heterocyclic-thio,
R$_g$² is halogen, and
R¹ and R$_a$³ are each as defined before.

(16) Process 16:

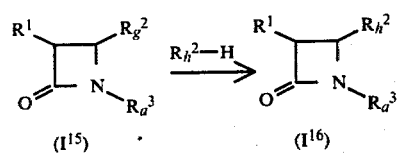

wherein
R$_h$² is a residue of nucleophile except halogen, and
R¹, R$_g$² and R$_a$³ are each as defined before.

(17) Process 17:

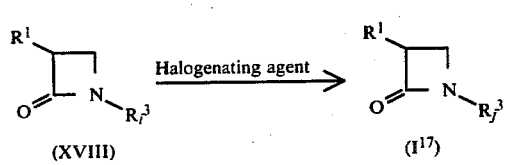

wherein
R$_i$³ is a group of the formula:

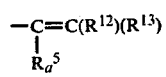

in which
R¹² and R¹³ are each alkyl and
R$_a$⁵ is as defined before,
R$_j$³ is a group of the formula:

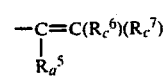

in which
R$_c$⁶ is alkyl or haloalkyl,
R$_c$⁷ is haloalkyl and
R$_a$⁵ is as defined before, and
R¹ is as defined before.

(18) Process 18:

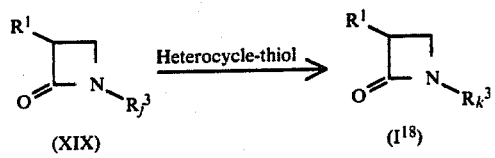

wherein
R$_k$³ is a group of the formula:

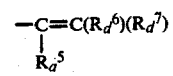

in which
R$_d$⁶ is alkyl or heterocyclic-thioalkyl,
R$_d$⁷ is heterocyclic-thioalkyl and
R$_a$⁵ is as defined before, and
R¹ and R$_j$³ are each as defined before.

(19) Process 19:

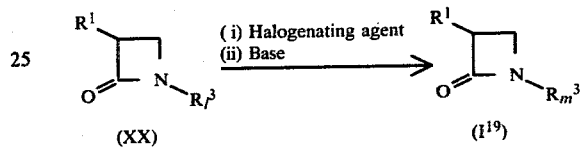

wherein
R$_l$³ is a group of the formula:

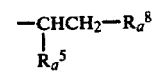

in which R$_a$⁵ and R$_a$⁸ are each as defined before,
R$_m$³ is a group of the formula:

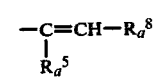

in which R$_a$⁵ and R$_a$⁸ are each as defined before and
R¹ is as defined before.

(20) Process 20:

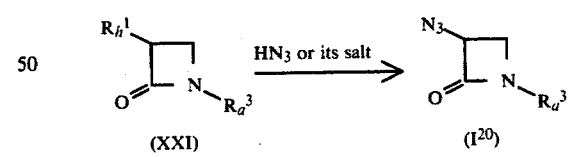

wherein
R$_h$¹ is halogen and
R$_a$³ is as defined before.

(21) Process 21:

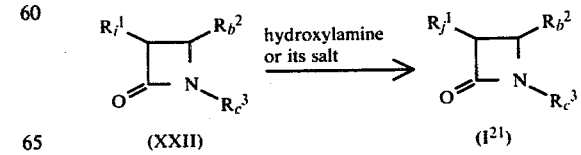

wherein
R$_j$¹ is a group of the formula:

$R^{14}$—COCONH— in which $R^{14}$ is aryl which may have possible substituent, $R_j{}^1$ is a group of the formula:

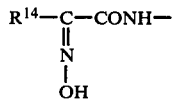

in which $R^{14}$ is as defined above, and
$R_b{}^2$ and $R_c{}^3$ are each as defined before, provided that, when $R_b{}^2$ is hydrogen,
$R_c{}^3$ is a group of the formula:

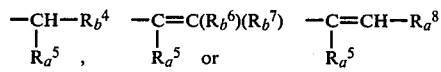

in which $R_b{}^4$ is phenyl bearing N-substituted or unsubstituted alkanesulfonamido, or aroylamino, naphthyl, aralkyl, arylthioalkyl or a heterocyclic group, and $R_a{}^5$, $R_b{}^6$, $R_b{}^7$ and $R_a{}^8$ are each as defined before.

With regards to the above Processes (1)–(21), the following points are to be noted.

1. In the above formulae, it is to be noted that each group of $R_a{}^6$ and $R_a{}^7$, $R_b{}^6$ and $R_b{}^7$, $R_c{}^6$ and $R_c{}^7$, $R_d{}^6$ and $R_d{}^7$, and $R^{12}$ and $R^{13}$ is bonded to the same carbon atom.

2. In the definitions of the groups for the formulae in the above-mentioned processes, the alkane, arene and heterocycle moieties may have at least one suitable substituent, the detail of which will be apparent in the following descriptions.

3. It is to be noted that the object compound (I) which can be prepared by the Processes illustrated above may include its derivative or pharmaceutically acceptable salt at the carboxy and amino functions.

Examples of the derivative of the carboxy group include acid amides, esters, nitrile and the like, the suitable examples of which are illustrated as follows.

(a) Acid amides include acid amide, N-alkyl acid amide (e.g. N-methyl acid amide, N-ethyl acid amide, etc.), N,N-dialkyl acid amide (e.g. N,N-dimethyl acid amide, N,N-diethyl acid amide, N-ethyl-N-methyl acid amide, etc.), N-phenyl acid amide, acid amide with pyrazole, imidazole or 4-alkylimidazole, and the like.

(b) Ester include; silyl esters, aliphatic esters, esters containing an aromatic or a heterocyclic group and esters with a N-hydroxy compound. The suitable silyl esters include trialkylsilyl (e.g. trimethylsilyl, triethylsilyl, etc.) esters, and the like.

Suitable examples of the aliphatic esters include:
saturated or unsaturated, acyclic or cyclic aliphatic esters, in which acyclic aliphatic esters may be branched such as alkyl (e.g. methyl, ethyl, propyl, isopropyl, butyl, tertbutyl, octyl, nonyl, undecyl, etc.) esters; alkenyl (e.g. vinyl, 1-propenyl, allyl, 3-butenyl, etc.) esters; alkynyl (e.g. 3-butynyl, 4-pentynyl, etc.) esters; cycloalkyl (e.g. cyclopentyl, cyclohexyl, cycloheptyl, etc.) esters; and the like.

Suitable examples of the esters containing an aromatic ring include, for example, aryl (e.g. phenyl, tolyl, xylyl, naphthyl, indanyl, dihydroanthryl, etc.) esters; aralkyl (e.g. benzyl, phenethyl, etc.) esters; aryloxyalkyl (e.g. phenoxymethyl, phenoxyethyl, phenoxypropyl, etc.) esters; arylthioalkyl (e.g. phenylthiomethyl, phenylthioethyl, phenylthiopropyl, etc.) esters; arenesulfinylalkyl (e.g. benzenesulfinylmethyl, benzenesulfinylethyl, etc.) esters; aroylalkyl (e.g. phenacyl, toluoylethyl, etc.) esters; and the like.

Suitable examples of the esters containing an heterocyclic ring include:
heterocyclic esters, heterocyclic-alkyl esters, etc.; in which the suitable heterocyclic ester include saturated or unsaturated, monocyclic or fused, 3 to 10-membered heterocyclic group containing 1 to 4 hetero-atom(s) such as an oxygen, sulfur and nitrogen atom, (e.g. pyridyl, piperidinyl, 2-pyridon-1-yl, tetrahydropyranyl, quinolyl, pyrazolyl, etc.) esters; and the like, and the suitable heterocyclic-alkyl esters include, for example, aforementioned heterocyclic group-substituted-alkyl (e.g. methyl, ethyl, propyl, etc.) esters; and the like.

Suitable examples of the esters with a N-hydroxy compound include esters with N,N-dialkylhydroxylamine (e.g. N,N-dimethylhydroxylamine, N,N-diethylhydroxylamine, N,N-dipropylhydroxylamine, etc.), esters with aldoxime or ketoxime (e.g. propanol oxime, butanal oxime, acetoxime, etc.), esters with N-hydroxyimide (e.g. N-hydroxyphthalimide, N-hydroxysuccinimide, etc.) and the like.

In the silyl esters, the aliphatic esters, the esters containing an aromatic or heterocyclic ring and the esters with a N-hydroxy compound as mentioned above, the moiety of these esters may optionally have one or more appropriate substituent(s) such as alkyl (e.g. methyl, ethyl, propyl, isopropyl, butyl, tert-butyl, etc.), cycloalkyl (e.g. cyclopropyl, cyclohexyl, etc.), alkoxy (e.g. methoxy, ethoxy, propoxy, isopropoxy, butoxy, tert-butoxy, etc.), alkanoyloxy (e.g. acetoxy, propionyloxy, pivaloyloxy, etc.), alkylthio (e.g. methylthio, ethylthio, propylthio, etc.), alkanesulfinyl (e.g. methanesulfinyl, ethanesulfinyl, propanesulfinyl, etc.), alkanesulfonyl (e.g. mesyl, ethanesulfonyl, etc.), phenylazo, halogen (e.g. chlorine, bromine, fluorine, etc.), cyano, nitro, etc..

Examples of which are illustrated more concretely as mono(di or tri)haloalkyl (e.g. chloromethyl, bromoethyl, dichloromethyl, 2,2,2-trichloroethyl, 2,2,2-tribromoethyl, 2,2,2-trifluoroethyl, etc.) esters, cyanoalkyl (e.g. cyanomethyl, cyancethyl, etc.) esters, mono(di, tri, tetra or penta)halophenyl (e.g. 4-chlorophenyl, 3,5-dibromophenyl, 2,4,5-trichlorophenyl, 2,4,6-trichlorophenyl, pentachlorophenyl, etc.) esters, cycloalkyl-substituted-alkyl (e.g. 1-cyclopropylethyl, etc.) ester, and the like.

Examples of pharmaceutically acceptable salts at the carboxy and amino functions of the object compounds are exemplified as follows.

Example of pharmaceutically acceptable salt at the carboxy is a salt with a base such as an inorganic base, that is, an alkali metal salt (e.g. sodium salt, potassium salt, etc.), an alkaline earth metal salt (e.g. calcium salt, magnesium salt, etc.), ammonium salt, an organic base (e.g. methylamine, trimethylamine, triethylamine, dicyclohexylamine, pyridine, ethanolamine, diethanolamine, N,N-dimethylaniline, etc.) salt, an amino acid (e.g. glycin, alanine, serine, aspartic acid, arginine, lysine, etc.) and the like.

Example of pharmaceutically acceptable salts at the amino is a salt with an acid such as an organic acid (e.g. hydrochloric acid, hydrobromic acid, sulfuric acid, etc.), an organic acid (e.g. formic acid, acetic acid, maleic acid, fumaric acid, lactic acid, tartaric acid, methanesulfonic acid, p-toluenesulfonic acid, etc.) and the like.

DETAILED EXPLANATION OF VARIOUS SUBSTITUENT

Various groups as defined hereinabove and the suitable examples thereof will be explained in details and be clear in the following descriptions.

1. Re. substituted amino [$R^1$]

Substituted amino includes acylamino, aralkylamino dialkylaminomethyleneamino, aralkylideneamino and the like, and is illustrated in more concrete in the following.

Acylamino includes acylamino such as an aliphatic acylamino, an aromatic acylamino, an araliphatic acylamino, a heterocyclic acylamino and a heterocyclic aliphatic acylamino, and acylamino represented by the formula:

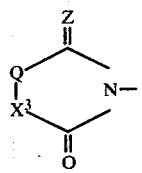

wherein Q is oxy or aryl-substituted-methylene, $X^3$ is carbonyl or imino, and Z is oxo or substituted methylene, the substituent being aryl or heterocyclic group or

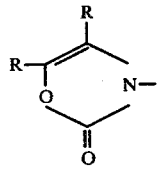

wherein R is aryl (e.g. phenyl, tolyl, xylyl, naphthyl, etc.)

(a) re. acyl moiety of acylamino

In the above acylamino, it is to be understood that the acyl moiety is derived from an organic carboxylic, organic sulfonic and organic phosphoric acids and in more detail, said acyl moiety may be aliphatic, aromatic, araliphatic, heterocyclic or heterocyclic-aliphatic acyl group, whose examples are illustrated below. Aliphatic acyl such as:

alkanoyl (e.g. formyl, acetyl, propionyl, butyryl, isobutyryl, valeryl, isovaleryl, pivaloyl, lauroyl, palmitoyl, etc.); alkanoyl (e.g. acryloyl, methacryloyl, crotonoyl, isocrotonoyl, etc.);

alkyloxalyl (e.g. methyloxalyl, ethyloxalyl, propyloxalyl, isopropyloxalyl, etc.);

alkanesulfonyl (e.g. mesyl, ethanesulfonyl, propanesulfonyl, butanesulfonyl, etc.);

alkenesulfonyl (e.g. ethylenesulfonyl, propenesulfonyl, etc.);

alkoxycarbonyl (e.g. methoxycarbonyl, ethoxycabonyl, propoxycarbonyl, isopropoxycarbonyl, butoxycarbonyl, tert-butoxycarbonyl, pentyloxycarbonyl, etc.);

dialkylphosphoryl (e.g. dimethylphosphoryl, diethylphosphoryl, diisopropylphosphoryl, etc.); and the like;

Aromatic acyl such as:

aroyl (e.g. benzoyl, toluoyl, xyoyl, naphthoyl, phthaloyl, etc.);

aryloxalyl (e.g. phenyloxalyl, tolyloxalyl, naphthyloxalyl, etc.);

arenesulfonyl (e.g. benzenesulfonyl, toluenesulfonyl, xylenesulfonyl, naphthalenesulfonyl, etc.);

diarylphosphoryl (e.g. diphenylphosphoryl, etc.); and the like;

Araliphatic acyl such as:

aralkanoyl (e.g. phenylacetyl, tolylacetyl, xylylacetyl, naphthylacetyl, biphenylylacetyl, phenylpropionyl, tolylpropionyl, naphthylpropionyl, 2-methyl-3-phenylpropionyl, 2-methyl-2-phenylpropionyl, 2-methyl-3-naphthylpropionyl, phenylbutyryl, naphthylbutyryl, phenylvaleryl, tolylvaleryl, naphthylvaleryl, diphenylacetyl, diphenylpropionyl, etc.);

aralkyloxalyl (e.g. benzyloxalyl, phenethyloxalyl, phenylpropyloxalyl, etc.);

aralkanesulfonyl (e.g. phenylmesyl, tolymesyl, naphthylmesyl, phenylethanesulfonyl, naphthylethanesulfonyl, phenylpropanesulfonyl, phenylbutanesulfonyl, etc.);

aralkenesulfonyl (e.g. phenylethylenesulfonyl, tolylethylenesulfonyl, naphthylethylenesulfonyl, phenylpropenesulfonyl, naphthylpropenesulfonyl, phenylbutenesulfonyl, etc.);

aralkoxycarbonyl (e.g. benzyloxycarbonyl, phenethyloxycarbonyl, phenylpropoxycarbonyl, diphenylmethoxycarbonyl, etc.);

diaralkylphosphoryl (e.g. dibenzylphosphoryl, etc); and the like.

Heterocyclic acyl such as:

heterocyclic-carbonyl containing 3 to 10 membered, monocyclic or fused heterocyclic group having heteroatom(s) selected from nitrogen, oxygen and sufur (e.g. aziridinecarbonyl, azetidinecarbonyl, pyrrolecarbonyl, 2H-pyrrolecarbonyl, imidazolecarbonyl pyrazolecarbonyl, pyridinecarbonyl, pyrazinecarbonyl, piperidinecarbonyl, piperazinecarbonyl pyrimidinecarbynyl, pyridazinecarbonyl, triazolecarbonyl, thiazolinecarbonyl, triazinecarbonyl, pyrrolidinecarbonyl, imidazolidinecarbonyl, oxiranecarbonyl, furoyl, pyrancarbonyl, thenoyl, morpholinecarbonyl, furazancarbonyl, oxazolecarbonyl, isoxazolecarbonyl thiazolecarbonyl, thiadiazolecarbonyl, oxadiazolecarbonyl, indolecarbonyl, 3H-indolecarbonyl, isoindolecarbonyl, indolizinecarbonyl, 1H-indazolecarbonyl, purinecarbonyl, benzimidazolecarbonyl, benzotriazolecarbonyl, quinolinecarbonyl, isoquinolinecarbonyl, naphthridinecarbonyl, quinoxalinecarbonyl, quinazolinecarbonyl, benzofurancarbonyl, chromenecarbonyl, isobenzofurancarbonyl, benzothiophenecarbonyl, xanthenecarbonyl, benzoxazolecarbonyl, benzisoxazolecarbonyl, benzothiazolecarbonyl, etc.);

Heterocyclic-oxalyl (e.g. thienyloxalyl, furyloxalyl, pyridyloxalyl, purinyloxalyl, tetrazolyloxalyl, etc.); and the like.

Heterocyclic-aliphatic acyl such as:

heterocyclic-alkanoyl (e.g. thienylacetyl, furylacetyl, pyridylacetyl, (pyridyl-1-oxide)acetyl, pyrrolylacetyl, imidazolylacetyl, pyrazolylacetyl, triazolylacetyl, tetrazolylacetyl, oxazolylacetyl, oxadiazolylacetyl, thiazolylacetyl, thiazolinylacetyl, thiadiazolylacetyl, morpholinylacetyl, pyranylacetyl, pyrrolidinylacetyl, pyrrolinylacetyl, thienylpropionyl, furylpropionyl, pyridylpropionyl, imidazolylpropionyl, oxazalypropionyl, oxadiazolylpropionyl, thiazolylpropionyl, thiadiazolylpropionyl; benzothienylacetyl, benzoxadiazolylacetyl, benzothiazolylacetyl, benzoxazolylacetyl, benzisoxazolylacetyl, benzotriazolylacetyl, indolylacetyl, purinylacetyl, purinylpropionyl, indolylpropionyl, etc.); heterocyclic-alkyloxalyl (e.g. thenyloxalyl, furfuryloxalyl, pyridylmethyloxalyl, tetrazolymethyloxalyl, thiadiazolylmethyloxalyl, etc.).

In the acyl moiety as exemplified above the aliphatic hydrocarbon moiety, aromatic hydrocarbon moiety and heterocyclic moiety in the acyl as exemplified above may have one or more suitable substituent(s) such as alkyl (e.g. methyl, ethyl, propyl, isopropyl, butyl, isobutyl, tert-butyl, pentyl, isopentyl, neopentyl, tert-pentyl, etc.), alkenyl (e.g. vinyl, 1-propenyl, allyl, isopropenyl, butenyl, etc.), aryl (e.g. phenyl, tolyl, xylyl, mesityl, naphthyl, methylnaphthyl, etc.), mono- or dialkylamino (e.g. methylamino, ethylamino, isopropylamino, butylamino, dimethylamino, diethylamino, etc.), arylamino (e.g. anilino, toluidino, xylidino, naphthylamino, etc.), aralkylamino (e.g. benzylamino, phenethylmethylamino, diphenylmethylamino, etc.), alkoxy (e.g. methoxy, ethoxy, propoxy, isopropoxy, butoxy, pentyloxy, isopentyloxy, neopentyloxy, etc.), aryloxy (e.g. phenoxy, tolyloxy, xylyloxy, naphthoxy, etc.), aralkoxy (e.g. benzyloxy, phenethyloxy, phenylpropoxy, phenylbutoxy, diphenylmethoxy, etc.), alkylthio (e.g. methylthio, ethylthio, propylthio, isopropylthio, butylthio, isobutylthio, pentylthio, isopentylthio, neopentylthio, etc.), arylthio (e.g. phenylthio, tolylthio, xylylthio, naphthylthio, etc.), aralkylthio (e.g. benzylthio, phenethylthio, phenylpropylthio, phenylbutylthio, diphenylmethylthio, etc.), alkanesulfonamido (e.g. mesylamino, ethanesulfonamido, propanesulfonamido, etc.), alkanoylamino (e.g. formylamino, acetylamino, propionylamino, butyrylamino, isobutyrylamino, etc.), carbomoyl, N-alkylcarbomoyl (e.g. N-methylcarbamoyl, N-ethylcarbamoyl, N-propylcarbamoyl, N-isopropylcarbamoyl, N-butylcarbamoyl, N-isobutylcabamoyl, etc.), carbazoyl, N-alkylcarbazoyl (e.g. N-methylcarbazoyl, N-ethylcarbazoyl, N-propylcarbazoyl, N-isopropylcarbazoyl, etc.), alkoxyimino (e.g. methoxyimino, ethoxyimino, propoxyimino, etc.), hydroxy, hydroxyimino, carboxy, nitro, halogen, sulfo, cyano, mercapto, amino, imino and combination thereof.

And the alkane and arene moieties of the above-mentioned substituents may further have one or more suitable functional group(s) such as amino, mono- or dialkylamino (e.g. methylamino, ethylamino, propylamino, isopropylamino, dimethylamino, diethylamino, etc.), hydroxy, carboxy, nitro, halogen sulfo, cyano and the like. Amino, imino, hydroxy, hydroxyimino, mercapto and carboxy group in these substituents as mentioned above may be protected by conventional protective groups.

Suitable examples of such amino and imino protective groups may be substituted or unsubstituted alkoxycarbonyl (e.g. methoxycarbonyl, ethoxycarbonyl, propoxycarbonyl, butoxycarbonyl, tert-butoxycarbonyl, chloromethoxycarbonyl, bromoethoxycarbonyl, tribromoethoxycarbonyl, trichloroethoxycarbonyl, etc.), substituted or unsubstituted aralkoxycarbonyl (e.g. benzyloxycarbonyl, phenethyloxycarbonyl, diphenylmethoxycarbonyl, nitrobenzyloxycarbonyl, bromobenzyloxycarbonyl, methoxybenzyloxycarbonyl, dinitrobenzyloxycarbonyl, etc.), halogenated alkanoyl (e.g,. trifluoroacetyl, etc.), substituted or unsabstituted aralkyl (e.g. benzyl, diphenylmethyl, trityl, bromobenzyl, nitrobenzyl, etc.), substituted or unsubstituted arylthio (e.g. phenylthio, nitrophenylthio, dinitrophenylthio, etc.), substituted or unsubstituted alkylidene (e.g. ethylene, isopropylidene, 2-carboxyisopropylidene, etc.) or its tautomeric 1-alkenyl, (e.g. 2-methoxycarbonyl-1-methylvinyl, etc.), aralkylidene (e.g. benzylidene, salicylidene, etc.) and the like.

Suitable examples of the hydroxy, hydroxyimino and mercapto protective groups may be the same as those for the amino and imino protective groups as mentioned above the additionally may be substituted or unsubstituted alkanoyl (e.g. acetyl, propionyl, butyryl, isobutyryl, valeryl, bromoacetyl, dichloroacetyl, trifluoroacetyl, etc.), substituted or unsubstituted aroyl (e.g. benzoyl, toluoyl, xyloyl, nitrobenzoyl, bromobenzoyl, salicyloyl, etc.), aroylmethyl (e.g. phenacyl, etc.) and the like. Suitable examples of the carboxy protective group may be an ester such as silyl ester, aliphatic ester, esters containing an aromatic or a heterocyclic group, esters with N-hydroxy compound, and concrete examples of which are the same as those given in the explanation of the ester of the compound (I), etc., mentioned hereinabove.

A preferred concrete example of the acyl moiety thus explained above may be bromoacetyl, dichloroacetyl, glycoloyl, glycyl, phenylglycoloyl, phenylglycyl, 2-hydroxyimino-2-phenylacetyl, 2-hydroxyimino-2-(4-hydroxyphenyl)acetyl, 4-hydroxyphenylglycyl, N-(2,2,2-trichloroethoxycarbonyl)phenylglycyl, N-benzyloxycarbonylpyranylglycyl, 3,5-dinitrobenzoyl, azidoacetyl, 3-amino-3-phenylpropionyl, 2-bromo-2-phenylacetyl, methoxyacetyl, 2-(2-amino-2-carboxyethoxy)acetyl, methylthioacetyl, 2-(2-amino-2-carboxyethylthio)acetyl, phenoxyacetyl, naphthoxyacetyl, phenylthioacetyl, methoxybenzoyl, 4-methoxyphenyloxalyl, 4-hydroxyphenyloxalyl, 5-methylisoxazolecarbonyl, 2-hydroxyimino-2-(4-hydroxyphenyl)acetyl, 2-hydroxyimino-2-(4-methoxyphenyl)acetyl, 2-(3-mesylaminophenyl)glycyl, cyanoacetyl, 2-(2-amino-4-thiazolyl)acetyl, 2-(2-imino-4-thiazoling-4-yl)acetyl, 2-hydroxyimino-2-[4-(3-tert-butoxycarbonylamino-3-methoxy-carbonylpropoxy)phenyl]acetyl, 2-hydroxyimino-2-[4-(3-phthalimido-3-methoxycarbonylpropoxy)phenyl]acetyl, 4-(3-tert-butoxycarbonylamino-3-methoxycarbonylpropoxy)phenylglyoxyloyl, 4-(3-phthalimido-3-methoxycarbonylpropoxy)phenylglyoxyloyl, 2-benzoyloxyimino-2-[4-(3-tert-butoxycarbonylamino-3-methoxycarbonylpropoxy)phenyl]acetyl, 4-[3-(4-methoxy benzyloxycarbonyl)-3-tert-butoxycarbonylamino]phenylglyoxyloyl, 2-[3-(3-amino-3-carboxypropoxy)phenyl]-2-hydroxyiminoacetyl, 3-(3-amino-3-carboxypropoxy)phenylglyoxyloyl, and the like.

More particularly, suitable examples of the abovementioned acyl may be phthalimido or a group of the formula:

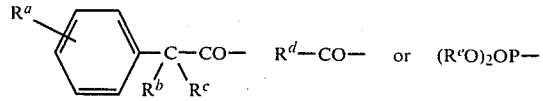

wherein
$R^a$ is hydrogen or alkoxy, which may be substituted by at least one substituent selected from amino and carboxy,
$R^b$ is hydrogen or amino and $R^c$ is hydrogen, or
$R^b$ and $R^c$ are linked together to form oxo or hydroxyimino, $R^d$ is aryloxyalkyl, heterocyclic-alkyl, or aralkoxy in which the arene moiety may be substituted by at least one substituent, and $R^e$ is alkyl, in the definitions of the above groups, the amino, hydroxyimino and carboxy may be protected by suitable protective group(s), and examples of which are the same as those given above.

As to the groups for $R^a$, $R^d$ and $R^e$ in the above formula suitable examples are illustrated as follows.

Suitable examples of alkoxy for $R^a$, there may be exemplified methoxy, ethoxy, propoxy, isopropoxy, butoxy, isobutoxy, secbutoxy, pentyloxy, isopentyloxy, etc.

Suitable examples of aryloxyalkyl for $R^d$ may be exemplified by phenoxymethyl, phenoxyethyl, tolyloxymethyl, xylyloxymethyl, naphthoxymethyl, etc.

Suitable examples of heterocyclic moiety of heterocyclic-alkyl for $R^d$, may be the same as those described in heterocyclic moiety of heterocyclic acyl in acylamino mentioned above and suitable examples of alkyl moiety may be exemplified by methyl, ethyl, propyl, isopropyl, butyl, pentyl, hexyl, etc. Suitable examples of alkyl for $R^e$ are the same as those given in alkyl moiety for $R^d$.

In the definitions of the above groups, the alkane, arene and heterocycle moieties may have at least one suitable substituent, suitable examples of which may be the same as those given in the explanation of the substituents of acylamino mentioned in the item 1. (a).

(b) re. aralkyl moiety of aralkylamino

In the aralkylamino, suitable examples of the aralkyl moiety may be exemplified by benzyl, diphenylmethyl, trityl, phenethyl, phenylpropyl, phenylbutyl, 4-methylbenzyl, 3, 4-dimethylbenzyl, 4-methylphenethyl, naphtylmethyl and the like, which may optionally have at least one suitable substituent. And as suitable examples of the substituent, there may be exemplified the same as those given in the explanation of the substituents of acylamino mentioned in the item 1. (a).

(c). re. dialkylamino-methyleneamino

In the dialkylamino-methyleneamino, suitable examples of dialkylamino moiety may be exemplified by N,N-dialkylamino (e.g. dimethylamino, diethylamino, dipropylamino, di-isopropylamino, dibutylamino, dihexylamino, N-methyl-N-ethylamino, N-propyl-N-pentylamino, N-ethyl-N-hexylamino, etc.), polymethyleneamino (e.g. ethyleneamino, trimethyleneamino, tetramethyleneamino, pentamethyleneamino, hexamethyleneamino, heptamethyleneamino, octamethyleneamino, etc.), and the like.

(d) re. aralkylideneamino

In the aralkylideneamino, suitable examples of aralkylidene moiety may be exemplified by benzylidene, tolylmethylene, xylylmethylene, naphthylmethylene, etc.), which may optionally have at least one suitable substituent, suitable examples of which may be the same as those given in the explanation of the substituents of acylamino mentioned in the item 1. (a).

2. Re. acyl moiety of acylamino [$R^1$, $R^1b$, $R^1d$, $R^1f$ and $R^1g$]

In the acylamino group, it is to be understood that suitable examples of said acyl moiety may be the same as those given in the explanation of acyl moiety of acylamino in the item 1. (a).

3. Re. substituted hydroxy [$R^1$, $R^{1'}$]

Substituted hydroxy includes alkoxy, aralkoxy, aryloxy, acyloxy and the like, and is illustrated in more concrete in the following.

(a) re. alkoxy

In the above alkoxy, it is to be understood that the alkyl moiety of the alkoxy may be exemplified by methyl, ethyl, propyl, isopropyl, butyl, sec-butyl, isobutyl, tert-butyl, pentyl, isopentyl, neopentyl, hexyl and the like.

(b) re. aralkoxy

In the above aralkoxy, it is to be understood that the aralkyl moiety of the aralkoxy may be the same as those given in the aralkylamino mentioned in the item 1. (b).

(c) re. aryloxy

In the above aryloxy, it is to be understood that the aryl moiety of the aryloxy may be exemplified by phenyl, tolyl, xylyl, naphthyl, etc. and the arene ring may be substituted by at least one suitable substituent, suitable examples of which may be the same as those given in the substituent of acylamino mentioned in the item 1. (a).

(d) re. acyloxy

In the above acyloxy, it is to be understood that the acyl moiety of the acyloxy may be the same as those given in the acyl moiety of acylamino mentioned in the item 1. (a).

4. Re. halogen [$R^1$, $R^{1'}$, $R^1e$, $R^1h$ and $R^2g$]

Suitable halogen may be exemplified by fluorine, chlorine, bromine, iodine and the like.

5. Re. protected amino [$R^{1'}$ and $R^1a$]

In the above protected amino, suitable examples of said protective group may be exemplified by acyl such as alkoxycarbonyl, dialkylphosphoryl, aralkoxycarbonyl, diaralkylphosphoryl, aralkylamino and the like, concrete examples of which are the same as those given in the explanation of acylamino mentioned in the item 1. (a), and as additional examples of said protected amino, there are also exemplified specific groups represented by formula:

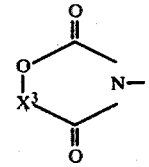

wherein $X^3$ is carbonyl or imino (i.e., 2,4,5-trioxo-oxazolidin-3-yl and 3,5-dioxo-1, 2,4-oxadiazolidin-4-yl), or

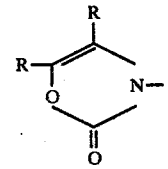

wherein R are each aryl, suitable examples of which are the same as those given in the explanation of the definition of the aryl mentioned in the item 1. (a).

6. Re. dialkylamino-methyleneamino [$R^1c$]

It is to be understood that suitable examples of dialkylamino moiety of the above group may be the same as those given in dialkylamino moiety mentioned in the item 1. (c).

7. Re. aralkylideneamino [$R^1c$]

It is to be understood that suitable examples of aralkylidene moiety of the above group may be the same as those given in the aralkylidene moiety mentioned in item 1. (d).

8. Re. aralkyl moiety of aralkylamino [$R^1e$], aralkoxyimino methyl [$R^1$] and aralkylthio [$R^2f$], and aralkyl [$R^4$, $R^4b$, $R^4c$, $R^4d$, $R^4e$, $R^4g$ and $R^{11}$]

It is to be understood that suitable examples of aralkyl or aralkyl moiety of the above groups may be the same as those given in aralkyl moiety of aralkylamino mentioned in the item 1. (b).

9. Re. protected amino, protected hydroxy and protected carboxy [$R^1f$ and $R^4d$]

It is to be noted that suitable examples of each of said protective groups may be the same as those given in the explanation of amino, hydroxy and carboxy protective groups in acylamino mentioned in the item 1. (a), respectively.

10. Re. aryl [$R^2$, $R^2a$, $R^2b$, $R^4$, $R^4a$, $R^4b$, $R^4g$, $R^{10}$ and $R^{14}$], and aryl moiety of arylthio [$R^2f$, $R^6$, $R^6a$ and $R^8a$] and arylthioalkyl [$R^4$, $R^4b$, $R^4c$ and $R^4g$]

Suitable examples of the aryl and said aryl moiety may be exemplified by phenyl, tolyl, xylyl, mesityl, naphthyl, and the like, which may have at least one suitable substituent. Suitable substituents may be the same as those exemplified in the explanation of the substituents of acylamino mentioned in the item 1. (a), and additionally N-substituted or unsubstituted alkanesulfonamido such as alkanesulfonamido (e.g. mesylamino, ethanesulfonamido, propanesulfonamido, etc.), N-arylglyoxyloylalkanesulfonamido (e.g. N-phenylglyoxyloylmesylamino, N-phenylglyoxyloylethanesulfonamido, N-tolylglyoxyloylpropanesulfonamido, N-naphthylglyoxyloylmesylamino, etc.), N-aroylaminoalkanoylalkanesulfonamido (e.g. N-(benzamidoacetyl)mesylamino, N-(phthalimidoacetyl)mesylamino, N-(benzamidoacetyl)ethanesulfonamido, N-(phthalimidoacetyl)propanesulfonamido, N-(phthalimidopropionyl)mesylamino, etc.), aroylalkoxy (e.g. phenacyloxy benzoylethoxy, benzoylpropoxy, toluoylmethoxy, toluoylethoxy, xylyolylmethoxy, naphthoylmeroxy, etc.) and the like.

11. Re. aralkenyl [$R^2$, $R^2a$ and $R^2b$]

Suitable examples of said aralkenyl may be exemplified by styryl, cinnamyl, tolylvinyl, xylylvinyl, naphthylvinyl, and the like, in which the aryl moiety may be substituted by at least one suitable substituent.

Suitable substituents may be the same as those given in the explanation of substituents of acylamino mentioned in the item 1. (a).

12. Re. a residue of nucleophile [$R^2$, $R^2a$, $R^2b$ and $R^2h$]

A residue of a nucleophile for $R^2$, $R^2a$, $R^2b$, and $R^2h$ may include halogen, a residue of N-nucleophile such as disubstituted amino, azido, a residue of O-nucleophile such as alkoxy, aryloxy, aralkoxy, a residue of S-nucleophile such as alkylthio, arylthio, aralkylthio, heterocyclic-thio and the like, in which the aryl and heterocyclic moiety may be substituted by at lease one suitable substituent.

Suitable examples of said disubstituted amino may be N,N-dialkylamino (e.g. N,N-dimethylamino, N-ethyl-N-methylamino, N-methyl-N-propylamino, N,N-diethylamino, N-ethyl-N-propylamino, N,N-dipropylamino, N,N-diisopropylamino, etc.); N-alkyl-N-arylamino (e.g. N-methylanilino, N-ethylanilino, N-propylanilino, N-isopropylanilino, N-methyltoluidino, N-ethyltoluidino, N-propyltoluidino, N-methylxylidino, N-ethylxylidino, N-methyl-N-naphthylamino, N-ethyl-N-naphthylamino, N-propyl-N-naphthylamino, etc.); N-alkyl-N-aralkylamino (e.g. N-benzyl-N-methylamino, N-benzyl-N-ethylamino, N-benzyl-N-propylamino, N-benzhydryl-N-methylamino, N-benzhydryl-N-ethylamino, etc.), and the like.

Suitable halogen may be the same as those given in the explanation of halogen mentioned in the item 4.

Suitable examples of the alkyl moiety of alkoxy and alkylthio may be the same as those given in the explanation of alkyl moiety of alkoxy mentioned in the item 3. (a).

Suitable examples of aralkyl moiety of aralkoxy and aralkylthio may be the same as those given in the explanation of aralkyl moiety of aralkylamino mentioned in the item 1. (b).

Suitable examples of aryl moiety of aryloxy and arylthio may be the same as those given in the explanation of aryl moiety of aryloxy mentioned in the item 3. (c).

Suitable examples of heterocyclic moiety of heterocyclic-thio may be the same as those given in the explanation of heterocyclic moiety of heterocyclic-acyl in acylamino mentioned in the item 1. (a).

13. Re. heterocyclic group [$R^4$, $R^4b$, $R^4c$ and $R^4g$], and hetrocyclic moiety of heterocyclic-thio [$R^2f$] and hetrocyclic-thioalkyl [$R^6$, $R^6a$, $R^6b$, $R^6c$, $R^7$, $R^7a$, $R^7b$ and $R^7d$]

It is to be understood that suitable examples of the heterocyclic group, and heterocyclic moiety, there may be the corresponing heterocyclic group as those given in the explanation of examples of heterocyclic acyl of acylamino mentioned in the item 1. (a).

14. Re. alkyl [$R^5b$, $R^6$, $R^6a$, $R^6b$, $R^6c$, $R^{12}$ and $R^{13}$], and alkyl moiety of alkylthio [$R^2f$], arylthioalkyl [$R^4$, $R^4b$, $R^4c$ and $R^4g$] and heterocyclic-thioalkyl [$R^6$, $R^6a$, $R^6b$, $R^6c$, $R^7$, $R^7a$. $R^7b$ and $R^7d$]

Suitable examples of said alkyl and said alkyl moiety may be exemplified by methyl, ethyl, propyl, isopropyl, butyl, isobutyl, sec-butyl, pentyl, isopentyl, neopentyl, hexyl and the like, which may have at least one suitable substituent.

Suitable substituent may be the same as those given in the explanation of substituents of acylamino mentioned in the item 1. (a).

15. Re. an organic residue bearing a carboxy group [$R^3$]

The "organic residue bearing the carboxy group" is to be understood to include:
aromatic hydrocarbon radical bearing always the carboxy group;
aliphatic hydrocarbon radical bearing always the carboxy group;
aromatic aliphatic hydrocarbon radical, in which the aliphatic hydrocarbon residue bears always the carboxy group;
in each group of which the aliphatic hydrocarbon moiety may be substituted with at least one other suitable substituent than the carboxy group and an optional carbon atom of said aliphatic hydrocarbon moiety may be replaced by a hetero-atom, and the aromatic moiety may be substituted with at least one suitable substituent.

Suitable examples of the radicals as stated above will be explained in more concrete and detail in the following.

(a) Regarding the aromatic hydrocarbon radical bearing always the carboxy group, the aromatic hydrocarbon residue therein include aryl group, whose examples are phenyl, tolyl, xylyl, mesityl, naphthyl and the like, and the said aromatic hydrocarbon residue may be substituted by at least one suitable substituent as shown hereinbelow.

(b) Regarding the aliphatic hydrocarbon radical bearing always the carboxy group, in which an optional carbon atom may be replaced by a heteroatom such as oxygen sulfur and nitrogen the examples of the aliphatic hydrocarbon residue therein include alkyl (e.g. methyl, ethyl, propyl, isopropyl, butyl, isobutyl, sec-butyl, tert-butyl, pentyl, isopentyl, neopentyl, etc.);
alkenyl (e.g. vinyl, 1-propenyl, allyl, isopropenyl, butenyl, 1- or 2-methylpropenyl, pentenyl, etc.);
alkynyl (e.g. ethynyl, propynyl, butynyl, 1- or 2-methyl propynyl, pentynyl, etc.);
alkoxyalkyl (e.g. methoxymethyl, ethoxymethyl, methoxyethyl, etc.);
alkoxyalkenyl (e.g. methoxyvinyl, methoxypropenyl, etc.);
alkoxyalkynyl (e.g. methoxyethynyl, ethoxypropynyl, etc.);
alkylthioalkyl (e.g. methylthiomethyl, ethylthiomethyl, ethylthioethyl, etc.);
alkylthioalkenyl (e.g. methylthiovinyl, methylthiopropynyl, ethylthiopropynyl, etc.); and
alkylthioalkynyl (e.g. methylthioethynyl, methylthiopropynyl, etc.).

The said aliphatic hydrocarbon residue including such as alkyl, alkenyl and alkynyl may be substituted by at least one suitable substituent as shown hereinbelow, and it is to be understood that number of carbons of said aliphatic hydrocarbon residue are up to 6 preferably 1-4 and, more preferably 1-3.

(c) Regarding the aromatic-aliphatic hydrocarbon radical in which the aliphatic hydrocarbon residue bears always the carboxy group, the aromatic-aliphatic hydrocarbon residue therein includes aromatic carbocyclic substituted-aliphatic hydrocarbon residue and aromatic heterocyclic substituted aliphatic hydrocarbon residue, and examples of the aliphatic hydrocarbon moiety are the same as those illustrated hereinabove (i.e. alkyl, alkenyl and alkynyl) in which an optional carbon atom may be replaced by a hetero-atom such as oxygen, sulfur and nitrogen, the particulars of these groups are explained in more concrete and detail be as follows.

(i) re. The aromatic carbocyclic substituted-aliphatic hydrocarbon radical, in which the aliphatic hydrocarbon residue bears always the carboxy;

In this radical, the aromatic carbocyclic substituted-hydrocarbon residue includes aryl-aliphatic hydrocarbon residue, in which the examples of the aryl moiety and aliphatic hydrocarbon moiety are illustrated hereinabove.

And suitable examples of them are illustrated as follows.

aralkyl (e.g. benzyl, phenethyl, 1-phenylethyl, phenylpropyl, phenylbutyl, phenylpentyl, tolylmethyl, tolylethyl, tolylpropyl, xylylmethyl, xylylethyl, xylylpropyl, mesitylmethyl, mesitylethyl, mesitylpropyl, naphthylmethyl, naphthylethyl, naphthylpropyl, naphthylbutyl, diphenylmethyl, diphenylethyl, diphenylpropyl, etc.);
aralkenyl (e.g. styryl, cinnamyl, phenylbutenyl, phenylpentenyl, tolylvinyl, tolylpropenyl, tolylbutenyl, xylylvinyl, xylylpropenyl, mesitylvinyl, naphthylvinyl, naphthylpropenyl, etc.); and the like.

And, in the above examples of the aromatic-aliphatic hydrocarbon residue, an optional carbon atom of the aliphatic hydrocarbon moiety may be replaced by a hetero-atom such as oxygen, sulfur, etc., the examples of which are as follows:

aryloxyalkyl (e.g. phenoxymethyl, phenoxyethyl, tolyloxymethyl, naphthoxyethyl, etc.);
aryl-substituted-alkoxyalkyl (e.g. α-methoxybenzyl, α- or β-methoxyphenethyl, α- or, β-ethoxyphenethyl, α- or β-propoxyphenethyl, α-, β- or γ-methoxyphenylpropyl, α-, β- or γ-ethoxyphenylpropyl, etc.);
aryloxyalkenyl (e.g. phenoxyvinyl, phenoxypropenyl, naphthoxypropenyl, etc.);
aryl-substituted-alkoxyalkenyl (e.g. α- or β-methoxystyryl, α-, β- or γ-methoxycinnamyl, α-, β- or γ-ethoxycinnamyl, etc.);
arylthioalkyl (e.g. phenylthiomethyl, phenylthioethyl, phenylthiopropyl, phenylthiobutyl, tolylthiomethyl, tolylthioethyl, xylylthioethyl, xylylthiopropyl, mesitylthiobutyl, naphthylthiomethyl, naphthylthioethyl, naphthylthiopropyl, etc.);
arylthioalkenyl (e.g. phenylthiovinyl, phenylthiopropenyl, phenylthiobutenyl, tolylthiovinyl, xylylthiopropenyl, naphthylthiovinyl, naphthylthiopropenyl, etc.); and the like.

(ii) re. The aromatic heterocyclic substituted-aliphatic hydrocarbon radical, in which the aliphatic by hydrocarbon residue bears always the carboxy;

In this radical, the aromatic heterocyclic substituted-aliphatic residue, heterocyclic substituted-aliphatic hydrocarbon residue, more particularly including monocyclic (preferably 5 to 6 membered) heterocyclic substituted-aliphatic residue and fused polycyclic (preferably 9-10 membered) heterocyclic substituted-aliphatic hydrocarbon residue, the said heterocycle containing at least one hetero-atom selected from nitrogen, oxygen and sulfur, and suitable examples of them are illustrated as follows:

heterocyclic-alkyl such as thienylalkyl (e.g. thienylmethyl, thienylethyl, thienylpropyl, thienylbutyl, dithienylpropyl, etc.), furylalkyl (e.g. furylmethyl, furylethyl, furylpropyl, difurylbutyl, etc.), pyridylalkyl (e.g. pyridylmethyl pyridylethyl, pyridylpropyl, etc.), pyrolylalkyl (e.g. pyrrolylmethyl, pyrrolylethyl, etc.), pyrazinylalkyl (e.g. pyrazanylmethyl, pyrazanylethyl, etc.), imidazolylalkyl (e.g. imidazolylmethyl, imidazolylethyl, etc.), pyrimidinylalkyl (e.g. pyrimidinylmethyl, pyrimidinylethyl, etc.), thiazolyalkyl (thiazolylmethyl, thiazolylethyl, etc.), oxazolylalkyl (e.g. oxazolylmethyl, oxazolylethyl, etc.), thiadiazolylalkyl (e.g. thiadiazolylmethyl, thiadiazolylethyl, etc.), oxadiazolylalkyl (e.g. oxadiazolylmethyl, oxadiazolylethyl, etc.), isoxazolylalkyl (e.g. isoxazolylmethyl, isoxazolylethyl, etc.), isothiazolylalkyl (e.g. isothiazolylmethyl, isothiazolylethyl, etc.), triazolylalkyl (e.g. triazolylmethyl, triazolylethyl, etc.), tetrazolylalkyl (e.g. tetrazolylmethyl, tetrazolylethyl, etc.), indolylalkyl (e.g. indolylmethyl, indolylethyl, etc.), purinylalkyl (e.g. purinylmethyl, purinylethyl, etc.), benzimidazolylalkyl (e.g. benzimidazolylmethyl, benzimidazolylethyl, etc.), benzotriazolylalkyl (e.g. benzotriazolylmethyl, benzotriazolylethyl, etc.), quinolylalkyl (e.g. quinolylmethyl, quinolylethyl, etc.), benzofurylalkyl (e.g. benzofurylmethyl, benzofurylethyl, etc.), benzothienylalkyl (e.g. benzothienylmethyl, benzothienylethyl, etc.), benzoxazolylalkyl (e.g. benzoxazolylmethyl, benzoxazolylethyl, etc.);
heterocyclic-alkenyl such as thienylalkenyl (e.g. thienylvinyl, thienylpropenyl, thienylbutenyl, etc.), furylalkenyl (e.g. furylvinyl, furylpropenyl, etc.), pyridylalkenyl (e.g. pyridylvinyl, pyridylpropenyl, etc.), isoxazolylalkenyl (e.g. isoxazolylvinyl, isoxazolylpropenyl, etc.), isothiazolylalkenyl (e.g. isothiazolylvinyl, isothiazolylpropenyl, etc.), oxazolylalkenyl (e.g. oxazolylvinyl, oxazolylpropenyl, etc.), oxadiazolylalkenyl (e.g. oxadiazolylvinyl, oxadiazolylpropenyl, etc.), thiazolylalkenyl (e.g. thiazolylvinyl, thiazolylbutenyl, etc.), thiadiazolylalkenyl (e.g. thiadiazolylpropenyl, thiadiazolylbutenyl, etc.); and the like.

In the above aromatic(including aromatic carbocyclic and aromatic heterocyclic)-aliphatic hydrocarbon residue as explained above, each of the aromatic moiety and aliphatic hydrocarbon moiety may be substituted by at least one suitable substituent as shown below.

And further, it is to be noted that number of carbons of the aliphatic hydrocarbon moiety are up to 6, preferably 1 to 4, more preferably 1 to 3 and most preferably one, and in case of number of carbon of the said aliphatic hydrocarbon moiety being one (most preferably), the aromatic-aliphatic hydrocarbon radical, in which the aliphatic hydrocarbon residue bears always the carboxy, can be shown by the following formula for a conventent sake:

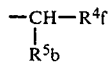

in which
$R^{4f}$ is aromatic (including aromatic carbcyclic and aromatic heterocyclic) radical,
$R^{5b}$ is carboxy or its derivative, or alkyl having caboxy or its derivative
wherein the meaning of the aromatic moiety is to be referred to the above explanation, and in more preferable, the organic residue bearing carboxy by the following formula:

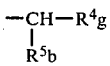

wherein
$R^{4g}$ is hydrogen, aryl, aralkyl, arylthioalkyl or heterocyclic group, and
$R^{5b}$ is as defined above.

Suitable aryl, aralky, arylthioalkyl is each as defined before.

As the suitable substituent as stated in the explanation of the radicals in the above (a), (b) and (c), there may be exemplified the same as those given in the explanation of the substituents of acylamino mentioned in the item 1. (a). Particularly, as to the radical in the above (c), preferable substituents are as follows.

As substituent for the aliphatic hydrocarbon moiety (e.g. alkyl, etc.), there may be exemplified by alkoxy, alkylthio and the like.

As substituent for aromatic carbocyclic moiety (e.g. aryl, etc.) aromatic heterocylic moiety, there may be exemplified by hydroxy, mercapto, nitro, amino, halogen, alkyl, alkoxy, alkylthio, aralkoxy, aralkylthio, N-substituted or unsubstituted alkanesulfonamido, aroylalkoxy and the like. Suitable examples of N-substituted or unsubstituted alkanesulfonamido may be the same as those given in the substituent of aryl in the item 10.

16. Re. N-substituted or unsubstituted alkanesulfonamido moiety of phenyl bearing N-substituted or unsubstituted alkanesulfonamido [$R^4$, $R^{4b}$ and $R^{4c}$]

It is to be noted that suitable N-substituted or unsubstituted alkanesulfonamido may be the same as those given in the substituent of aryl mentioned in the item 10.

17. Re. aroylalkoxy moiety of phenyl bearing aroylalkoxy [$R^4$, $R^{4b}$ and $R^{4c}$]

It is to be noted that suitable aroylalkoxy may be the same as those given in the substituent of aryl mentioned in the item 10.

18. Re. the ester moiety of esterified carboxy [$R^{5c}$]

It is to be noted that suitable esterified carboxy may be the same as those given in the explanation of esters in the compound (I).

19. Re. derivative of carboxy [$R^5$, $R^{5a}$ and $R^{5b}$]

It is to be noted that suitable derivative of carboxy may be the same as those given in the explanation of the derivative of carboxy in the compound (I) mentioned before.

20. Re. haloalkyl [$R^6$, $R^{6a}$, $R^{6b}$, $R^{6c}$, $R^7$, $R^{7a}$, $R^{7b}$ and $R^{7c}$]

In the above group, suitable examples of said haloalkyl may be preferably mono-haloalkyl (e.g. chloromethyl, bromomethyl, iodomethyl, 1-bromoethyl, 1-bromopropyl, 1-chlorobutyl, 1-iodoethyl, 1-bromohexyl, etc.).

21. Re. inorganic or organic cation for M in the group $R^{3f}$

Suitable examples of the inorganic or organic cation include a metal cation such as alkali metal cation (e.g. sodium cation, potassium cation, etc.), alkaline earth metal cation (e.g. calcium cation, magnesium cation, etc.); ammonium ion; an organic base ion [e.g. methylammonium ion, trimethylammonium ion, triethylammonium ion, dicyclohexylammonium ion, dicyclohexylammonium ion, pyridinium ion, 2-hydroxyethylammonium ion, bis(2-hydroxyethyl)ammonium ion, N,N-dimethyl-N-phenylammonium ion, etc.].

22. Re. dialkylamino [$R^9$]

It is to be noted that suitable dialkylamino may be the same as those given in the explanation of dialkylamino moiety in dialkylamino-methyleneamino mentioned in the item 6.

23. Re. aryl [$R^9$]

It is to be noted that suitable aryl may be the same as those given in the explanation of aryl moiety in aralkylideneamino mentioned in the item 7.

24. Re. s-nucleophile [$R^2$]

It is to be noted that suitable s-nucleophile may be the same as those given in the s-nucleophile in a residue of nucleophile mentioned in the item 12.

Starting Compounds

The starting compound of this invention includes known and new compounds, and they were prepared as follows.

(a) Preparation of the starting compound (III)

The starting material (III) can be prepared by condensing an amino acid of the formula: $R^3$—$NH_2$ with formaldehyde as shown in the following scheme.

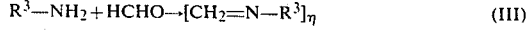

wherein $R^3$ and $\eta$ are each as defined above.

In this preparation, some of the amino acids of the formula: $R^3$—$NH_2$; wherein $R^3$ is as defined above, are new and they can be each prepared by the conventional methods of well known amino acid syntheses.

In this preparation, the amino acids of the formula: $R^3—NH_2$ can be employed in a form of salt with an acid such as an inorganic acid salt (e.g. hydrochloride, hydrobromide, etc.); an organic acid salt (e.g. formate, acetate, p-toluenesulfonate, etc.); and the like:, or with a base such as an inorganic base salt (e.g. sodium salt, potassium salt, calcium salt, magnesium salt, etc.); an organic base salt (e.g. trimethylamine salt, dicyclohexylamine salt, pyridine salt, picoline salt, lutidine salt, ethanolamine salt, morpholine salt, etc.); and the like.

The present reaction is usually carried out in a solvent such as water, methanol, ethanol, diethyl ether or in any solvent which does not have an adverse influence on the reaction.

The reaction temperature is not limited, but the reaction is usually carried out under the conditions from cooling to heating.

(b) Preparation of the starting compound ($IV_A$)

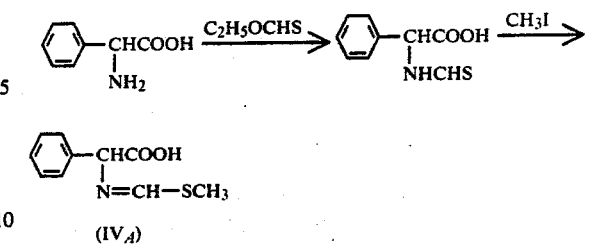

(c) Preparation of the starting compounds ($XIII_A$) and ($XIII_B$)

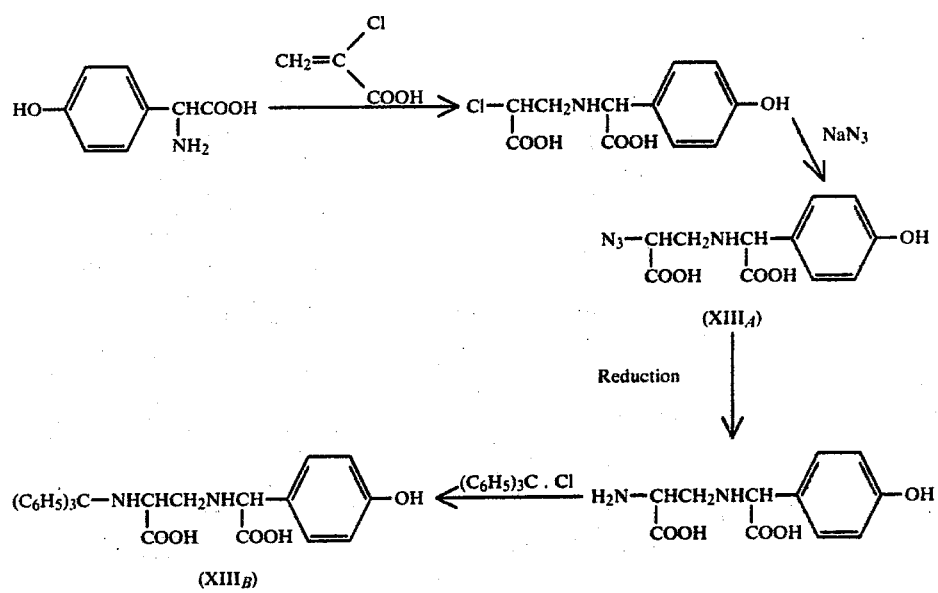

(d) Preparation of the starting compound ($XVIII_A$)

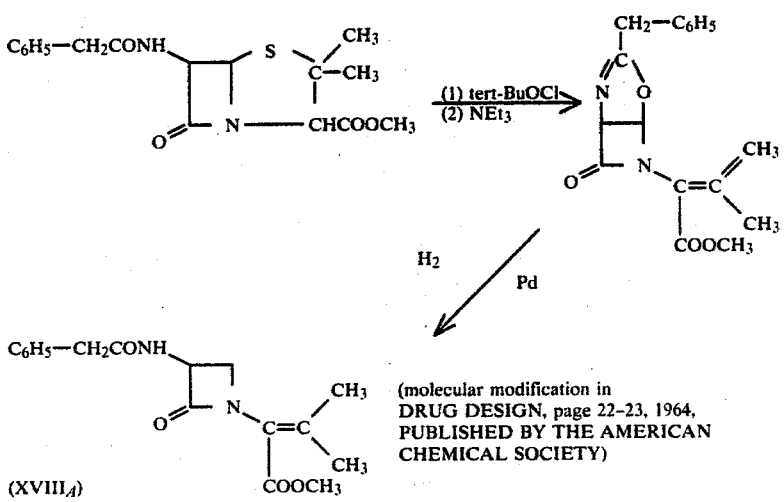

(molecular modification in DRUG DESIGN, page 22-23, 1964, PUBLISHED BY THE AMERICAN CHEMICAL SOCIETY)

DETAILED EXPLANATION OF PROCESSES FOR PREPARATION OF 2-AZETIDINONE COMPOUNDS (1) Process 1

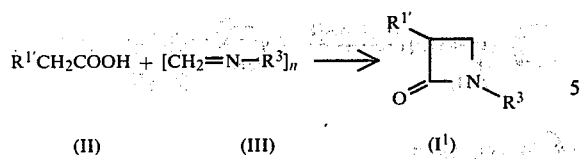

This process relates to a method for preparing 3-protected amino-2-azetidinone compound (I¹) by reacting a compound (III) with 2-substituted acetic acid (II) in the presence of Lewis acid and base.

Typical reactive derivative of substituted acetic acid (II) includes its acid anhydride, ester, acid halide, amide, azide and the like. (i) The acid anhydride may be a mixed anhydride with an acid such as dialkylphosphoric acid, aryl- or diaryl-phosphoric acid, diaralkylphosphoric acid, halophosphoric acid, dialkylphosphorous acid, sulfuric acid, alkyl-carbonic acid, aliphatic carboxylic acid, aromatic carboxylic acid or the symmetrical acid anhydride, and preferably, with an acid such as diethylphosphoric acid, diphenylphosphoric acid, dibenzylphosphoric acid, ethyl carbonic acid, tert-butyl carbonic acid, trichloroethyl carbonic acid, pivalic acid, trichloroacetic acid, trifluoroacetic acid, benzoic acid and the like. (ii) The suitable ester may be a conventional activated ester such as substituted alkyl ester (e.g. cyanomethyl ester, methoxymethyl ester, etc.), olefinic ester (e.g. allyl ester, propargyl ester, etc.), substituted aryl ester (e.g. 4-nitrophenyl ester, 2,4-dinitrophenyl ester, pentachlorophenyl ester, etc.), an silyl ester (e.g. trimethylsilyl ester, dimethyl methoxy silyl ester, etc.), an ester with N-hydroxy compound such as acetoxime, N-hydroxysuccinimide, N-hydroxyphthalimide, 1-hydroxy-6-chlorobenzotriazole, etc., and the like. (iii) The acid amide may be an activated amide such as pyrazolide, imidazolide, 4-methylimidazolide, and the like. (iv) Suitable acid halide may be the acid chloride, acid bromide, and the like.

Examples of Lewis acid include halogenated metal or non-metal compound, particularly preferred examples of with are boron trihalide (e.g. boron trifluoride, boron trichloride, boron tribromide, etc.); complex of boron trihalide with solvent such as ether (e.g. diethyl ether, etc.), alcohol (methanol, etc.), carboxylic acid (e.g. acetic acid, etc.), etc., alminium halide (e.g. alminium chloride, alminium bromide, etc.), zinc halide (e.g. zinc chloride, etc.), stannic halide (e.g. stannic chloride, etc.), ferric halide (e.g. ferric chloride, etc.), titanium halide (e.g. titanium chloride, etc.), silicon tetrahalide (e.g. silicon tetrachloride, etc.), antimony halide (e.g. antimony chloride, etc.) and the like. In the examples of Lewis acid as mentioned above, boron trifluoride diethyl etherate is preferably employed in the present invention.

Suitable examples of the base include an organic base such as
trialkylamine (e.g. trimethylamine, triethylamine, tributylamine, etc.);
N,N-dialkylaniline (e.g. N,N-dimethylaniline, N,N-diethylaniline, etc.);
N,N-dialkylbenzylamine (e.g. N,N-dimethylbenzylamine, etc.);
N-substituted or unsubstituted heterocyclic compound (e.g. N-methylmorpholine, N-methylpiperidine, pyridine, dimethylaminopyridine, picoline, lutidine, quinoline, 1,5-diazabicyclo-[4,3,0]-5-nonene, 1,4-diazabicyclo [2,2,2]octane, 1,8-diazabicyclo-[5,4,0]-8-undecene, etc.) and the like.

The present reaction can be conducted preferably from under cooling to at ambient temperature and usually in a conventional solvent such ad dichloromethane, chloroform, carbon tetrachloride, diethyl ether, dioxane, pyridine, N,N-dimethylformamide or an optional mixture thereof, or in any other solvent which does not have an adverse influence on the reaction. And when a Lewis acid and/or a base are in liquid, they may be also used as a solvent.

With regard to the reaction of the present invention, there may occasionally occur the following side reaction in the course of the reaction or the post-treatment, that is:

the carboxy group of the compound (I¹) or (III) may be transformed into the corresponding functional derivatives or adversely the functional derivatives at the carboxy of the compound (I¹) or (III) may be transformed into the free carboxy;

in the above mentioned substituent(s) in the organic residue bearing the caboxy for R³ of the compound (III) amino, mono-substituted amino (e.g. alkanesulfonamido, etc.), mercapto and/or hydroxy group(s) may be acylated with the compound (II) into corresponding acylamino N-mono-substituted-N-acylamino, acylthio and (or) acyloxy group; or such amino group may be transformed into its salt with an acid such as an inorganic acid (e.g. hydrochloric acid, hydrobromic acid, sulfuric acid, etc.) or organic acid (e.g. formic acid, acetic acid, fumaric acid, maleic acid, p-toluenesulfonic acid, etc.); and the aforementioned protective group(s) for the substituent(s) such as amino, mono-substituted amino, mercapto, hydroxy or carboxy in the explanation of the organic residue bearing the carboxy group for R³, and the aforementioned protective group(s) for the substituent(s) such as amino, mono-substituted amino, mercapto, hydroxy, hydroxyimino or carboxy in the substituted amino, substituted hydroxy for R¹' may be removed to form the corresponding amino, mono-substituted amino, mercapto, hydroxy, hydroxyimino or carboxy in the compound (I¹).

It is to be understood that the side reaction as mentioned above are also included within the scope of the present invention.

The object compound (I¹), prepared by the present process 1 may be given as a mixture of two stereoisomers due to the asymmetric carbon atom of the third position of the azetidine ring, and these mixture may be optionally resolved, if necessary, into the corresponding stereoisomer according to conventional resolution methods.

(2) Process 2

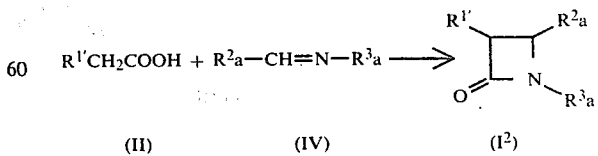

This process relates to a method for preparing 3-protected amino-4-substituted-2-azetidinone compound (I²) by reacting a compound (IV) with a acetic acid derivative (II).

The acetic acid derivative (II) can be used in a form of its reactive derivative at the carboxy, and suitable examples of which are the same as those given in the explanation of the 2-substituted acetic acid (II) in the Process 1.

The reaction may be conducted in a conventional manner, for example, preferably under cooling to at ambient temperature and usually in a solvent which does not have an adverse influence on the reaction, for instance, ethyl acetate, dichloromethane, chloroform, carbon tetrachloride, benzene, N,N-dimethylformamide, water, etc., and hydrophilic solvent among the above can be used in a mixture with water.

The reaction can be preferably conducted in the presence of a base, suitable examples of which may be the same as those given in the explanation of the Process 1, and additionally an inorganic base (e.g. sodium carbonate, potassium carbonate, magnesium carbonate, calcium carbonate, sodium bicarbonate, potassium bicarbonate, magnesium bicarbonate, calcium bicarbonate, sodium hydroxide, potassium hydroxide, calcium hydroxide, etc.).

Further, the reaction can be occasionally conducted in the presence of Lewis acid, suitable examples of which are the same as those given in the explanation of Process 1.

(3) Process 3

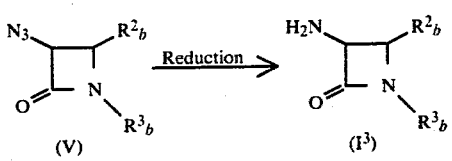

This process relates to a method for preparing a compound ($I^3$) by reducing an azido group of a compound (V).

The reduction is conducted in a conventional manner such as a chemical reduction and catalytic reduction.

Suitable reducing agents to be used in chemical reduction are a metal (e.g. tin, zinc, iron, etc.), or a combination of metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide or platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually carried out in a solvent. A suitable solvent to be used may be, e.g. water, methanol, ethanol, propanol, and other conventional organic solvent or a mixture thereof. Additionally, in case that the abovementioned acids to be used in chemical reduction are in liquid, they can be also used as a solvent. Further, a suitable solvent to be used in catalytic reduction may be, e.g., the abovementioned solvent, and other conventional solvent, such as diethyl ether, dioxane, tetrahydrofuran, etc. or a mixture thereof.

The reaction is preferably carried out under somewhat milder conditions such as cooling or warming.

Process 4

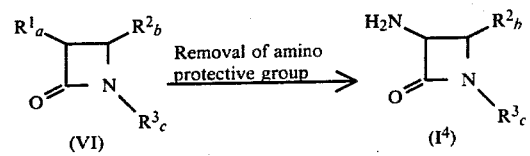

This process relates to a method for preparing a compound ($I^4$) by removing a protective group of the protected amino of compound (VI).

The reaction of this process is conducted by removing the substituted group on the amino group in a conventional manner.

Suitable method for this removal reaction includes hydrolysis reduction, a combined method comprising iminohalogenation and iminoetherification followed hydrolysis, and the like.

In the above methods, suitable reagents to be used are exemplified as follows.

(i) For hydrolysis which refers to the same meaning as solvolysis including, for example, acidolysis, alcoholysis, aminolysis, hydrozinolysis, etc.

Hydrolysis is preferably carried out in the presence of an acid or base.

Suitable acid is an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion-exchange resin and the like.

Suitable base is an inorganic base such as alkali or alkaline earth metal hydroxide, carbonate or bicarbonate (e.g. sodium hydroxide, potassium carbonate sodium bicarbonate, calcium hydroxide, magnesium hydroxide, etc.), ammonium hydroxide and the like; an organic base such as an alkoxide or phenoxide of the above metal, (e.g. sodium ethoxide, sodium methoxide, lithium phenoxide, an amine such as mono-, di- or trialkylamine (e.g. methylamine, ethylamine, propylamine, isopropylamine, butylamine, N,N-dimethyl-1, 3-propanediamine, trimethylamine, triethylamine, etc.), unsubstituted, mono- or disubstituted arylamine (e.g. aniline, N-methylaniline N,N-dimethylaniline, etc.) or a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.), a basic ion exchange resin and the like.

The hydrolysis is preferably conducted under somewhat milder conditions such as cooling or warming and usually in any solvent which does not have an adverse influence on the reaction, e.g., water, a hydrophilic solvent such as methanol, ethanol, propanol, N,N-dimethylformamide, tetrahydrofuran, dioxane, dimethylsulfoxide, etc. or a mixture thereof. In case that the abovementioned acids and bases are in liquid, they can be also used as a solvent.

(ii) For reduction

Reduction is carried out in a conventional manner. including chemical reduction and catalytic reduction. The said chemical and catalytic reductions are conducted in the substantially same as those exemplified for the foregoing Process 3, respectively. Therefore, suitable reagents and the reaction conditions (e.g. solvent, temperature, etc. are to be referred to the descriptions of Process 3.

(iii) For combined method

In this process, when the protected amino group for R¹a is an organic carboxamide, the carboxamide bond can be more preferably cleaved by the following modified hydrolysis. That is, the compound (VI) is first subjected to iminohalogenation, iminoetherification, and then hydrolysis.

The first and second steps of this method are preferably carried out in an anhydrous solvent at rather lower temperature. Suitable solvent for the first step (i.e. iminohalogenation) is an aprotic solvent such as dichloromethane, chloroform, diethyl ether, dioxane, etc., and for the second step (i.e. iminoetherification) is usually the same as those in the above first step. Those two steps and the last step (i.e. hydrolysis step) are most preferably conducted in one-batch system.

Suitable iminohalogenation agents includes a halogenating agent such as phosphorus compound (e.g. phosphorus trichloride, phosphorus pentachloride, phosphorus tribromide, phosphorus pentabromide, phosphorus oxychloride etc.), thionyl chloride, phosgen, and the like.

Suitable iminoetherifying agent may be an alcohol such as an alkanol (e.g. methanol, ethanol, propanol, isopropanol, butanol, tert-butanol, etc.) or the corresponding alkanol having alkoxy (e.g. methoxyethanol, ethoxyethanol, etc.), a thiol such as alkane thiol (e.g. methane thiol, ethane thiol, etc.) and alkoxide or thiolate of metal such as alkali metal, alkaline earth metal (e.g. sodium methoxide, potassium ethoxide, magnesium ethoxide, lithium methoxide, potassium methanethiolate, etc.), and the like. Thus obtained reaction product is, if necessary, hydrolyzed in a conventional manner. The hydrysis is preferably carried out at ambient temperature or under cooling, and proceeds simply pouring the reaction mixture into water or a hydrophilic solvent such as alcohol (e.g. methanol, ethanol, etc.) moistened or admixed with water, and if necessary, with addition of an acid or base as exemplified above.

In the present process, in some occasion when the protected amino group for R¹a of the compound (VI) is a type of phthalimido group, the removal reaction partially proceeds to produce an intermediary phthalamic acid or phthalamide type compound, which is to be understood to be included within the scope of the compound (VI), but these types of intermediary compound can further be converted to the 3-amino -2- azetidinone compound (I⁴) by the removal reaction of this process. And further, in the course of the present process, some kinds of the substituent(s) (e.g. N-substituted or unsubstituted alkanesulfonamido, carbamoyl, protected hydroxy, protected carboxy, etc.) in the group for $R^3c$ (particularly $R^4b$) of the compound (VI) may also occasionally be transformed into the corresponding alkanesulfonamido, amino, hydroxy or carboxy group, etc. It is to be understood that all the cases of the reaction are included within the scope of the present process.

(5) Process 5

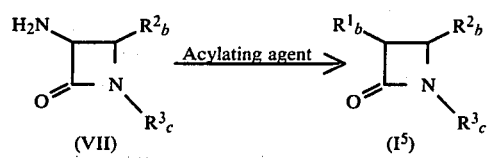

This process relates to a method for preparing a compound (I⁵) by reacting 3-amino-2-azetidinone compound (VII) with an acylating agent.

In this reaction, the starting 3-amino -2- azetidinone compound (VII) can be used in the activated form, that is as an activated derivative of the amino function attached to the third position of the compound (VII). Such activated functional derivative includes the isocyanate or isothiocyanate, the Shiff's base, the salt with an acid (e.g. hydrochloric acid, hydrobromic acid, etc.) and such other conventional reactive derivatives as formed by the reaction with a silyl compound (e.g. trimethylsilyl chloride, etc.), a phosphorus compound (e.g., phosphorus oxychloride, phosphorus trichloride, etc.) and the like.

An acylating agent includes an organic acid such as an organic carboxylic acid, an organic carbonic acid, an organic carbamic acid, an organic sulfonic acid, an organic phosphoric acid and the like, which corresponds to those comprising the acyl moiety of the acylamino mentioned in the item 1.(a), and a salt or reactive derivative thereof. More particularly, the said organic acid is an acid comprising aliphatic, aromatic araliphatic, heterocyclic and heterocyclic-aliphatic acyl groups.

Suitable reactive derivative of the above-mentioned organic acid are each refered to the same as those given in the explanation of the 2-substituted acetic acid (II) in the Process 1.

The reaction may be preferably conducted especially in case of using a corresponding free acid as the acylating agent, in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)-carbodiimide, N,N'-diethylcarbodiimide, N,N'-diisopropylcarbodiimide, N-ethyl-N'-(3-dimethylaminopropyl) carbodiimide, N,N'-carbonyl-bis(2-methylimidazole), pentamethyleneketene-N-cyclohexylimine, diphenylketene-N-cyclohexylimine, alkoxyacetylene, 1-alkoxy-1-chloroethylene, 6-chloro-1-(4-chlorobenzenesulfonyloxy)-1H-benzotriazole, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)-isoxazolium hydroxide, (chloromethylene)dimethylammonium chloride, 2,2,4,4,6,6-hexachloro-1,3,5,2,4,6-triazatriphosphorine, or a mixed condensing agent such as triphenylphosphine and carbon tetrahalide (e.g. carbon tetrachloride, carbon tetrabromide, etc.) or halogen (e.g. chlorine, bromine, etc.) and the like.

In case of using a reactive derivative as the acylating agent, the reaction may be conducted in the presence of base such as those given in Process 1.

The reaction is usually carried out in a conventional solvent which does not have an adverse influence on the reaction, e.g. water, acetone, dichloromethane, chloroform, N,N-dimethylformamide and the like, and a liquid condensing agent or base can be also used as the solvent.

The type of acylating agents to be used, such as free acid, salt or reactive derivative are usually elected according to the kinds of the acid and solvent used for the specific reaction.

In this process including the reaction and past-treatment steps, there may give occasionally by products due to, for example, side reaction between amino monosubstituted amino, hydroxy and/or mercapto function of the starting compound (VII) and the acylating agent to obtain the 3-acylamino-2-azetidinone compound ($I^5$) bearing the corresponding acylated substituent. These cases of reactions are to be noted to be included within the scope of the present process.

(6) Process 6

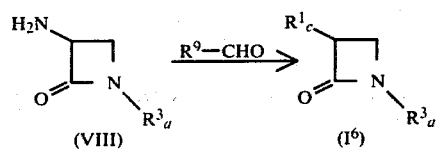

This process relates to the preparation of compound ($I^6$) by reacting a compound (VIII) with a formyl compound of the formula: $R^9$—CHO, wherein $R^9$ is as defined herein above, or its reactive derivative.

The reactive derivative of the formyl compound includes a derivative of its formyl function (—CHO) such as an acetal

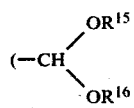

wherein $R^{15}$ and $R^{16}$ are each alkyl) (e.g. dimethyl acetal, diethyl acetal, dipropyl acetal, etc.), a dihalide

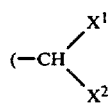

wherein $X^1$ and $X^2$ are each halogen) (e.g. dichloride, dibromide, etc.) and the like.

The reaction may be preferably conducted in a conventional manner, for example in the presence of a condensing agent such as those exemplified in Process 5 as well as Lewis acid such as phosphorus oxychloride, thionyl chloride, phosphorus tribromide, phosgene, etc. and the like.

(7) Process 7

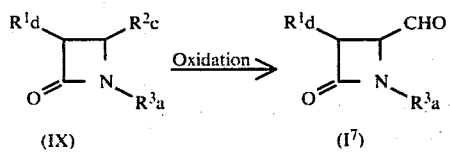

This process relates to the preparation of a compound having a formyl group ($I^7$) by subjecting a compound having an aralkenyl group (IX) to oxidative cleavage of its carbon-carbon double bond of aralkenyl group attached to the fourth position of the nucleus.

The oxidation is conducted in a conventional manner, for example, in the presence of an oxidizing agent such as permanganate (e.g. potassium permanganate, etc.), metal oxide (e.g. chromium trioxide, osmium tetroxide, etc), nitrous oxide, hydrogen peroxide, ozone and the like. (8) Process 8

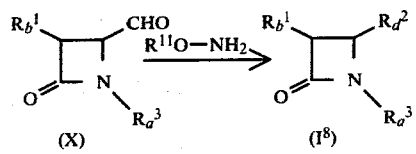

This process relates to a method for preparing a compound having an iminomethyl group ($I^8$) by reacting the compound (X) with an amino compound of the formula: $R^{11}O$—$NH_2$, wherein $R^{11}$ is as defined hereinabove, in a conventional manner.

The amino compound ($R^{11}O$—$NH_2$) may be used in the form of its salt with an acid such as an inorganic acid (e.g. hydrochloric acid, sulfuric acid, etc.) and an organic acid (e.g. formic acid, acetic acid, p-toluenesulfonic acid, etc.), in which the reaction may be preferably carried out under alkaline condition, for example, in the presence of alkali metal compound (e.g. sodium hydroxide, potassium hydroxide, sodium carbonate, potassium carbonate, sodium bicarbonate, potassium phosphate, etc.), alkaline earth metal compound (e.g. calcium hydroxide, calcium carbonate, etc.) and the like.

The reaction is conducted in a conventional manner.

(9) Process 9

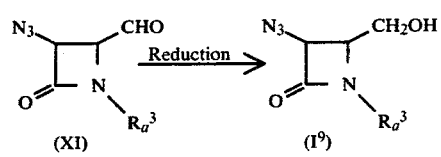

This process relates to a method for preparing a compound having a hydroxymethyl group ($I^9$) by subjecting the compound having a formyl group (XI) to reduction of the formyl group in a conventional manner.

Suitable reduction applied for the present reaction may be, for example, reduction using an alkali metal borohydride (e.g. sodium borohydride, lithium borohydride, etc.) and the like. The reaction is conducted in a conventional manner.

(10) Process 10

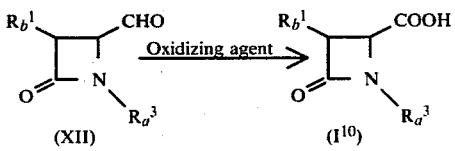

This process relates to a method for preparing a compound having a carboxy group ($I^{10}$) by subjecting a compound having a formyl group (XII) to oxidation of the formyl group at the fourth position of the nucleus.

Suitable oxidizing agents are permanganate (e.g. potassium permanganate, etc.), chromium trioxide, nitric acid, hydrogen peroxide, organic peracid or its salt (e.g. perbenzoic acid, m-chloroperbenzoic acid, peracetic acid, etc., or the sodium or potassium salt thereof, etc.), metal oxide (e.g. silver oxide, etc.) and the like. The reaction is conducted in a conventional manner.

(11) Process 11

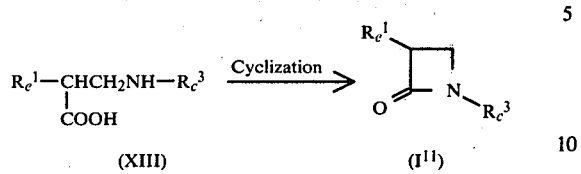

(XIII)        (I¹¹)

The reaction is conducted by subjecting a compound (XIII) or its reactive derivatice at the carboxy group to intramolecular cyclization reaction.

The reaction may be preferably conducted by activating the carboxy group of the starting compound (XIII), i.e. by transforming the carboxy group into the corresponding reactive derivative.

Suitable reactive derivative at the carboxy group is the correspondingly same as those illustrated as for 2-substituted acetic acid (II) in Process 1.

This reaction may be usually conducted in a conventional manner, for example in a solvent, in the presence of a condensing agent and/or a base.

Suitable examples of the bases are the same as those exemplified in the explanation of the base in Processes 1 and 2, and those of the condensing agent may be the same as those given in Process 5 and additionally acetic anhydride, a Gringnard reagent (e.g., ethylmagnesium bromide, phenylmagnesium bromide, etc.), a trialkylmetal (e.g., triisobutylalminum, etc.) and the like.

(12) Process 12

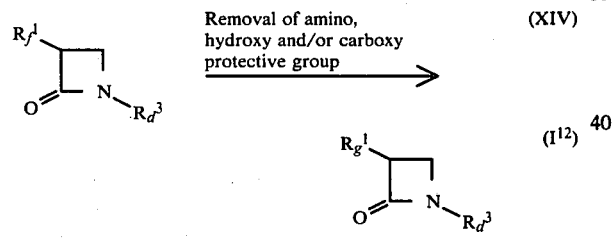

This process relates to a method for preparing a compound ($I^{12}$) by subjecting a compound (XIV) to removal reaction of a protective group therein.

The removal reaction of the protective group in the compound (XIV) is conducted by a conventional method such as hydrolysis, and other conventional method, e.g., reduction, a method of using a metal salt such as methyl halide, metal mercaptide, metal cyanide, metal thiocyanate and the like. By this reaction a protective group of the protected amino, protected hydroxy and/or protected carboxy function(s) in the acylamino ($R^1f$) of the compound (XIV) is removed to provide the corresponding amino, hydroxy and/or carboxy function(s), respectively.

With regard to the removal reaction, the reaction procedure is substantially the same as that in Processes 3 and 4, and accordingly a mode of the procedure (e.g. hydrolysis, reduction, etc.) and examples of the reagents, solvents and other reaction conditions (e.g. temperature, etc.) are substantially the same as those exemplified in Processes 3 and 4.

(13) Process 13

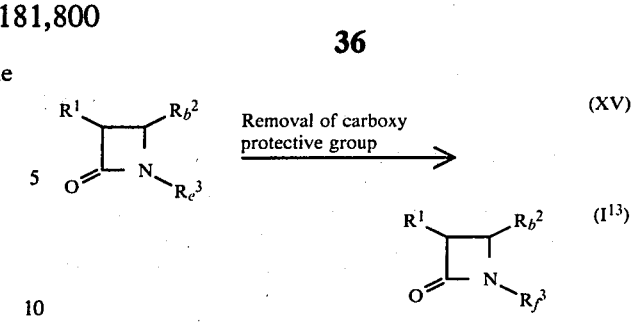

This process relates to a method for preparing a carboxy compound ($I^{13}$) by subjecting a compound (XV) to removal of a carboxy protective group therein.

Methods to be employed for this reaction include hydrolysis, reduction and other conventional methods, for example, using a metal salt such as metal halide, metal mercaptide, metal cyanide, metal thiocyanate and the like.

The hydrolysis and reduction are conducted in conventional manners, respectively.

Suitable reagents, solvents and other reaction conditions (e.g. temperature, etc.), etc. to be used in the hydrolysis and in the reduction are substantially the same as those given in the explanations for the Process 4 and for the process 3, respectively, and accordingly the details of them are to be referred to said corresponding explanations.

(14) Process 14

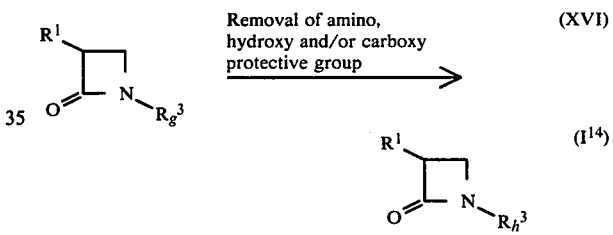

This process relates to a method for preparing a compound ($I^{14}$) by subjecting a compound (XVI) to removal reaction of a protective group therein.

The removal reaction of the amino, hydroxy and/or carboxy protective group(s) in the group $R^3g$ of the compound (XVI) is conducted in a conventional manner such as hydrolysis, reduction and the like, each of which is the substantially same as those in Processes 3, 4 and 12, whereby the protective group(s) of protected amino, protected hydroxy and/or protected carboxy function(s) in the aralkyl group ($R^4d$) of the compound (XVI) is removed to provide the corresponding amino, hydroxy and/or carboxy function(s), respectively.

The mode of the reaction procedure and examples of the reagents, solvents and other reaction condition (e.g. temperature, etc.) are substantially the same as those given in Process 12, the details of which are to be referred to the explanations in Process 12 and also in Processes 3 and 4, correspondingly.

(15) Process 15

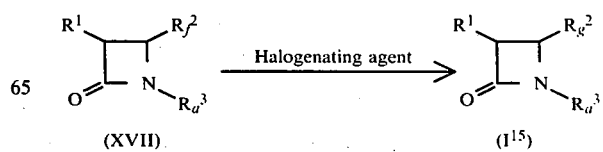

(XVII)        ($I^{15}$)

This process relates to a method for preparing a compound having halogen ($I^{15}$) by reacting a compound (XVII) with a halogenating agent in a conventional manner.

Suitable halogenating agent may include halogen such as chlorine, bromine, iodine, an inorganic halogeno compound such as phosphorus pentachloride, thionyl chloride, curprous chloride, etc., an organic halogen compound such as N-haloamide (e.g. N-bromoacetamide, N-iodoacetamide, etc.), N-haloimide (e.g. N-chlorosuccinimide, N-bromosuccinimide, N-chlorophthalimide, etc.), pyridinium bromide.perbromide, dioxane.bromide, hypohalogenous acid or its alkyl ester (e.g. hypochlorous acid, tert-butyl hypochlorite, etc.), a sulfenyl halide (e.g. benzenesulfenyl chloride, quinoline-2-sulfenyl chloride, etc.), and the like.

The reaction is usually conducted in a conventional manner as used in the halogenation reaction.

(16) Process 16

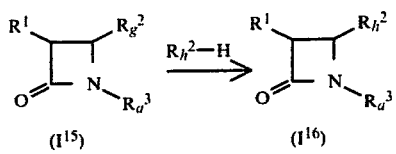

This process relates to a method for preparing a compound having a heterocyclic-thio group ($I^{16}$) by reacting a compound ($I^{15}$) with a nucleophile of the formula: $R^{2}h$—H, wherein $R^{2}h$ is as defined hereinabove, in a conventional manner.

The nucleophiles of the formula $R^{2}h$—H may include N-nucleophiles such as hydrazoic acid, an amine; O-nucleophiles such as an aliphatic, araliphatic or aromatic hydroxy compound (e.g. an alkanol, an aralkanol, phenol, etc.); and S-nucleophiles such as an aliphatic, araliphatic, aromatic or heterocyclic thiol compound (e.g. an alkanethiol, an arenethiol, an aralkanethiol, heterocycle-thiol, etc.), and the examples for the definitions of $R^{2}h$ are already explained in detail in the above explanation of the group.

Among these nucleophiles, S-nucleophiles and O-nucleophiles may be employed in a form of a salt such as an alkali metal salt (e.g. sodium salt, potassium salt, etc.), and alkaline earth metal salt (e.g. magnesium salt, calcium salt, etc.), or the like. And the hydrazoic acid is conveniently used in a form of its alkali metal salt, i.e. sodium azide.

(17) Process 17

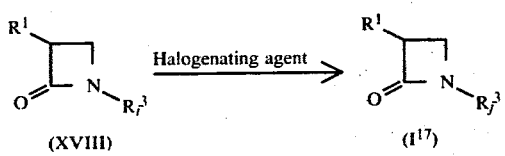

This process relates to a method for preparing a compound ($I^{17}$) by halogenating a compound (XVIII) in a conventional manner.

Suitable halogenating agent includes halogen (e.g. chlorine, bromine, iodine); N-haloamide such as N-haloacetamide (e.g. N-bromoacetamide), N-halolactam (e.g. N-bromocaprolactam), N-haloimide (e.g. N-chlorosuccinimide, N-bromosuccinimide, N-bromophthalimide, etc.), N-halohydantoin (e.g. N-chlorohydantoin, N-bromohydantoin, etc.), and the like.

The halogenation is conducted in a conventional manner, preferably under exposure to light or in the presence of a catalytic amount of other conventional radical initiator such as peroxide (e.g. benzyl peroxide, m-chloroperbenzoic acid, tert-butyl hydroperoxide, etc.), an azo compound (e.g. azo bis(isobutyronitrile), methyl $\alpha,\alpha'$-azoisobutyrate, etc.), etc. or in the coexistence of said peroxide (e.g. tert-butyl hydroperoxide) and a cobalt or copper salt of organic carboxylic acid (e.g. lauric acid, etc.) thereof.

(18) Process 18

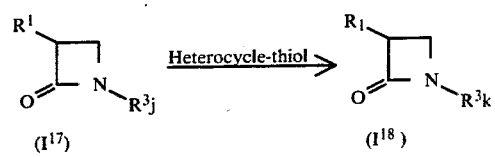

This process relates to a method for preparing a compound ($I^{18}$) by reacting a halogenated compound ($I^{17}$) with a heterocycle-thiol compound.

Heterocycle-thiol compound is a thiolic nucleophile and can be represented by the formula: $R^{17}$—SH (wherein $R^{17}$ is heterocyclic group). Suitable examples of said heterocyclic group for $R^{17}$ are the same as those exemplified hereinabove in the explanation of heterocyclic moiety in the heterocyclic acyl in the acylamino mentioned in the item 1. (a) and are to be referred to them. In this reaction, haloalkyl group for $R^{6}c$ and/or $R^{7}c$ of the compound ($I^{17}$) reacts with the heterocycle thiol compound ($R^{17}$—SH) to produce the compound ($I^{18}$) wherein $R^{6}d$ and/or $R^{7}d$ are heterocyclic ($R^{17}$)-thioalkyl.

The reaction is carried out in a conventional manner, for example, in the presence of a base such as substantially the same ones as exemplified in the Process 2.

(19) Process 19

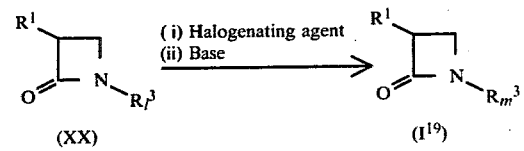

This process relates to a method for preparing an olefinic compound ($I^{19}$) by halogenating a compound (XX) and continuously dehydrohalogenating the resultant product in a conventional manner.

In this process, the compound (XX) is first halogenated by reacting with a halogenating agent to provide a haloganated compound of the formula:

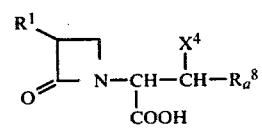

wherein $X^4$ is halogen such as chlorine, bromine, etc. and $R^1$ and $R^8a$ are each defined above.

Suitable halogenating agents include halogen (e.g., chlorine, bromine, etc.), sulfuryl halide (e.g., sulfuryl chloride etc.), N-haloamide (e.g., N-bromoacetamide, etc.), N-haloimide (e.g., N-bromosuccinimide, N-bromophthalimide, etc.), N-haloheterocyclic compound (e.g., N-chloro-1H-benzotriazole, 1,3,5-trichloro-2,4,6-trioxoperhydrotriazine, etc.), a complex of halogen and halo-compound (e.g., phenyl iodochloride, pyridinium iodobromide, etc.), metal halide (e.g., cupric chloride, etc.), and any other halogenating agent used conventionally for the halogenation on the carbon atom adjacent to a sulfur atom.

The resultant halogenated compound is then dehydrohalogenated to provide the compound ($I^{19}$). The said dehydrohalogenation is usually conducted in the presence of a base such as those exemplified for the hydrolysis in Process 4.

The both of halogenation and dehydrohalogenation steps are usually conducted in a conventional solvent.

(20) Process 20

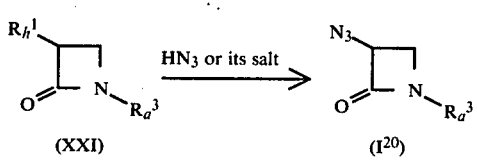

(XXI)　　　　　　($I^{20}$)

This process relates to a method for preparing a 3-azido-2-azatidinone compound ($I^{20}$) by reacting a 3-halo-2-azetidinone compound (XXI) with hydrazoic acid or its salt in a conventional manner.

Suitable salt of hydrazoic acid includes an alkali metal salt (e.g. sodium azide, potassium azide, etc.), an alkaline earth metal salt (e.g. calcium azide, magnesium azide, etc.) and the like. The reaction is conducted by a conventional method.

(21) Process 21

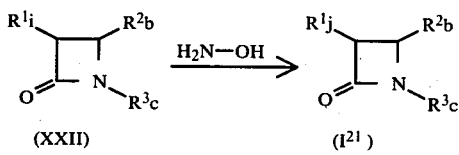

(XXII)　　　　　　($I^{21}$)

This process relates to a method for preparing a compound having an imino group ($I^{21}$) by reacting a compound (XXII) with hydroxylamine or its salt.

Suitable salt of hydroxylamine may be an inorganic acid (e.g. hydrochloric acid, sulfuric acid, etc.) salt, or an organic acid (e.g. formic acid, acetic acid, 2,2,2-trifluoroacetic acid, p-toluenesulfonic acid, etc.) salt. In such case, the reaction may be preferably conducted in the presence of a base. Suitable base may be an inorganic base (e.g. sodium hydroxide, potassium hydroxide, calcium hydroxide, sodium bicarbonate, etc.) or an organic base (e.g. triethylamine, pyridine, lutidine, etc.).

The reaction is usually conducted in conventional manner. For example, the reaction is conducted preferably at ambient temperature or somewhat elevated temperature, and in conventional solvent which does not have an adverse influence on the reaction such as water, methanol, ethanol, propanol, N,N-dimethylformamide or a mixture thereof.

Each of the reaction products in the abovementioned processes can be isolated and purified in a conventional manner to the skilled in the arts and it may also be used as a starting compound of the next processes without isolation and purification.

The object compound (I) of this invention includes a useful antibiotic for the treatment of microbial infections in animals and human being and a useful intermediate for preparing the useful antibiotics. That is, the 3-acylamino-2-azetidinone compounds (I) have antimicrobial activities against various pathogenic microorganisms as illustrated bellow and is useful as antibiotics for the treatment of microbial infections in animals and human being; and, for example, 3-phthalimido, 3-azido- or 3-amino-2-azetidinone compound (I) is the important intermediates for preparing the abovementioned 3-acylamino-2-azetidinone compound as illustrated in informentioned processes.

Antimicrobial activities of some representative object compounds of this invention, i.e., 3-acylamino-2-azetidinone compound, against pathogenic microorganisms are given in the following M.I.C. (minimum inhibitory concentration) values which are determined by conventional method.

| Example No. of the object compound | Microorganism | M.I.C.($\mu$g/ml) |
|---|---|---|
| 91 | Escherichia coli | 0.25 |
|  | Pseudomonas aeruginosa | 4 |
| 108 | Escherichia coli | 0.5 |
|  | Staphylococcus aureus | 3.75 |
|  | Pseudomonas aeruginosa | 15 |
| 112 | Escherichia coli | 15 |
|  | Baccillus subtilis | 15 |
| 115 | Staphylococcus aureus | 60 |

The object compounds (I) of the present invention may be formulated for administration in any convenient way by analogy with other antibiotic.

Thus, the composition of present invention can be used in the form of pharmaceutical preparation, for examples, in solid, semisolid or liquid form, which contains the active object compound (I) of the present invention in admixture with a pharmaceutical organic or inorganic carrier, or excipient suitable for external or parenteral applications. The active ingredient may be compounded, for example, with usual carriers into tablets, peletts, capsules, suppositories, solutions, emulsions, aqueous suspensions, and other form suitable for therapeutical administration. The carriers which can be used are glucose, lactose, gum acacia, gelatin, mannitol, starth paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes. The compositions of the present invention can also contain preserving or bacteriostatic agents thereby keeping the active ingredient in the desired preparations stable in activity. The active objecting compound (I) of the present invention in included in the composition of the present invention in an amount sufficient to produce the desired therapeutic effect upon the bacterially infected process or condition. While the dosage or therapeutically effective quantity of the compound (I) of the present invention varies from and also depends upon the age and condition of each individual patient to be treated, a daily dose of about 0.5–5 g, preferably 1–2 g/day of the active ingredient is generally given.

The following examples are given for the purpose of illustration of the present invention.

Preparation of the new starting materials:

(A) For the Process 1;

EXAMPLE A-1

Preparation of 1,3,5-tris[D-1-methoxycarbonyl-1-(2-thienyl)methyl]-perhydro-1,3,5-triazine D-2-(2-Thienyl)glycine methyl ester hydrochloride (25.0 g.) was dissolved in water (130 ml.) and to the aqueous solution was dropwise added benzene (250 ml.). 1 N Aqueous sodium hydroxide (120 ml.) was added dropwise to the mixture under ice-cooling, and further, 37% aqueous formaldehyde solution (9.9 ml) was added to the mixture, whereafter the mixture was stirred at the same temperature for 2 hours. The benzene layer was separated from the reaction mixture and the remaining aqueous solution was extracted with ethyl acetate. This extract and the separated benzene layer were combined, washed with water, and then dried over magnesium sulfate. The solvent was distilled off from the solution under reduced pressure to give a residue which was crystallized from diisopropyl ether to give 1,3,5-tris[D-1-methoxycarbonyl-1-(2-thienyl)-methyl]-perhydro-1,3,5-triazine (16.5 g.).

Infrared absorption spectrum (hereinafter merely referred to as IR)—$\nu cm^{-1}$ (Nujol): 1739.

N M R absorption spectrum (hereinafter merely referred to as NMR)—(internal standard: tetramethylsilane, hereinafter merely referred to as TMS)—$\delta$ppm (CDCl$_3$): 3.69 (9H, s), 3.78 (6H, s), 4.89 (3H, s), 6.80 to 7.43 (9H, m).

The following compounds (Examples A-2 to A-18) were prepared by reacting the corresponding amine derivative with formaldehyde in substantially the same manner as one described in Example A-1.

EXAMPLE A-2

1,3,5-Tris(D-$\alpha$-methoxycarbonyl-3-mesylaminobenzyl)-perhydro-1,3,5-triazine.

IR—$\nu cm^{-1}$ (film): 3550 (broad), 3240, 1730.

NMR (TMS)—$\delta$ppm (CDCl$_3$): 3.08 (3H, s), 3.61 (5H, broad s), 4.53 (1H, s), 7.0 to 7.6 (4H, m), 7.71 (1H, broad s).

EXAMPLE A-3

1,3,5-Tris[dl-1-methoxycarbonyl-1-(1-naphthyl)methyl]-perhydro-1,3,5-triazine, mp 148° to 151° C.

EXAMPLE A-4

1,3,5-Tris(dl-1-methoxycarbonyl-2-phenylthioethyl)-perhydro-1,3,5-triazine.

N M R (TMS)—$\delta$ppm (CDCl$_3$): 3.10 to 3.90 (15H, m), 3.68 (9H, s), 7.1 to 7.5 (15H, m).

EXAMPLE A-5

1,3,5-Tris(4-benzyloxy-$\alpha$-methoxycarbonylphenethyl)-perhydro-1,3,5-triazine, mp 106° to 109° C.

EXAMPLE A-6

1,3,5-Tris(dl-erythro-$\alpha$-methoxycarbonyl-$\beta$-methoxyphenethyl)-perhydro-1,3,5-triazine.

EXAMPLE A-7

1,3,5-Tris[dl-1-(2-furyl)-1-methoxycarbonylmethyl]-perhydro-1,3,5-triazine.

N M R (TMS)—$\delta$ppm (CDCl$_3$): 3.5 to 3.8 (12H, m), 4.74 (3H, s), 6.28 (6H, m), 7.32 (3H, m).

EXAMPLE A-8

1,3,5-Tris(methoxycarbonylmethyl)-perhydro-1,3,5-triazine.

I R—$\nu cm^{-1}$ (film): 1740 to 1755.

N M R (TMS)—$\delta$ppm (CDCl$_3$): 3.48 (6H, s), 3.73 (15H, s).

EXAMPLE A-9

1,3,5-Tris(ethoxycarbonylmethyl)-perhydro-1,3,5-triazine.

I R—$\nu cm^{-1}$ (film): 1730 to 1750.

N M R (TMS)—$\delta$ppm (CDCl$_3$): 1.25 (9H, t, J=6 Hz), 3.45 (6H, s), 3.73 (6H, s), 4.17 (6H, q, J=6 Hz).

EXAMPLE A-10

1,3,5-Tris(benzyloxycarbonylmethyl)-perhydro-1,3,5-triazine.

I R—$\nu cm^{-1}$ (film): 1740.

N M R (TMS)—$\delta$ppm (CDCl$_3$): 3.44 (6H, s), 3.69 (6H, s), 5.10 (6H, s), 7.40 (15H, s).

EXAMPLE A-11

1,3,5-Tris(D-$\alpha$-methoxycarbonylbenzyl)-perhydro-1,3,5-triazine, mp 148° to 155° C.

I R—$\nu cm^{-1}$ (Nujol): 1730.

N M R (TMS)—$\delta$ppm (CDCl$_3$): 3.49 (9H, s), 3.51 (6H, s), 4.50 (1H, s), 7.42 to 6.90 (15H, m).

EXAMPLE A-12

1,3,5-Tris(D-4-benzyloxy-$\alpha$-methoxycarbonylbenzyl)-perhydro-1,3,5-triazine, mp 141° to 145° C.

I R—$\nu cm^{-1}$ (Nujol): 1725.

N M R (TMS)—$\delta$ppm (CDCl$_3$): 3.58 (15H, s), 4.50 (3H, s), 5.04 (6H, s), 6.80 (6H, d, J=9 Hz), 7.29 (6H, d, J=9 Hz), 7.40 (15H, s).

EXAMPLE A-13

1,3,5-Tris(D-4-benzyloxycarbonyloxy)-$\alpha$-methoxycarbonylbenzyl)-perhydro-1,3,5-triazine.

I R—$\nu cm^{-1}$ (film): 1740, 1710.

N M R (TMS)—$\delta$ppm (CDCl$_3$): 3.50 (15H, s), 4.42 (3H, s), 5.23 (6H, s), 6.99 (6H, d, J=9 Hz), 7.23 (6H, d, J=9 Hz), 7.27 (15H, s).

EXAMPLE A-14

1,3,5-Tris(dl-2-methoxycarbonyl-1-phenylethyl)-perhydro-1,3,5-triazine, mp 92° to 96° C.

I R—$\nu cm^{-1}$ (Nujol): 1735.

EXAMPLE A-15

1,3,5-Tris(4-methoxycarbonylphenyl)-perhydro-1,3,5-triazine, mp 208° to 209.5° C. (dec.).

I R—$\nu cm^{-1}$ (Nujol): 1710.

EXAMPLE A-16

1,3,5-Tris(D-$\alpha$-benzyloxycarbonylbenzyl)-perhydro-1,3,5-triazine, mp 118° to 119° C.

I R—$\nu cm^{-1}$ (Nujol): 1730, 1740 (shoulder).

N M R (TMS)—$\delta$ppm (CDCl$_3$): 3.57 (6H, s), 4.52 (3H, s), 4.95 (6H, s), 6.95 to 7.45 (30H, m).

EXAMPLE A-17

1,3,5-Tris(D-$\alpha$-methoxycarbonyl-3-nitrobenzyl)-perhydro-1,3,5-triazine.

I R—$\nu cm^{-1}$ (liquid film): 1740.

N M R (TMS)—$\delta$ppm (CDCl$_3$): 3.65 (15H, broad s), 4.65 (3H, s), 7.45 to 8.2 (12H, m).

EXAMPLE A-18

1,3,5-Tris(D-$\alpha$-benzyloxycarbonyl-4-benzyloxybenzyl)-perhydro-1,3,5-triazine, mp 108° to 110° C.

I R—νcm⁻¹ (Nujol): 1745, 1735, 1720.

N M R (TMS)—δppm (CDCl₃): 3.55 (6H, s), 4.47 (3H, s), 4.92 (12H, s), 6.76 (6L H, d, J=8 Hz), 7.00 to 7.44 (36H, m).

EXAMPLE A-19

Preparation of 1,3,5-tris(4-phenacyloxy-α-phenacyloxycarbonylbenzyl)-perhydro-1,3,5-triazine A N,N-dimethylformamide (100 ml) solution containing N-tert-butoxycarbonyl-2-(4-hydroxyphenyl)glycine (9.18 g.), phenacyl bromide (6.86 g.) and sodium hydroxide (1.37 g.) was stirred at ambient temperature for 4 hours. The reaction mixture was poured into water (500 ml.) and extracted with three 50 ml portions of ethyl acetate. The combined extract was washed with water and then dried over magnesium sulfate. The solution was evaporated to dryness under reduced pressure to give an oily N-tert-butoxycarbonyl-2-(4-hydroxyphenyl) glycine phenacyl ester (13.19 g.).

I R—νcm⁻¹ (film): 3400 (broad), 1750, 1710, 1690.

A dried acetone (71 ml) solution containing the above-prepared compound (3.56 g), phenacyl bromide (1.84 g) and potassium carbonate (1.28 g) was heated under reflux for 7 hours. The insoluble substances were filtered off from the reaction mixture and the filtrate was evaporated to dryness under reduced pressure to give a residue, which was dissolved in chloroform. The solution was washed with water and dried over magnesium sulfate. The chloroform was distilled off from the solution under reduced pressure to give a residue. The residue was crystallized with diisopropyl ether to give N-tert-butoxycarbonyl-2-(4-phenacyloxyphenyl)glycine phenacyl ester (4.12 g), which was recrystallized from ethanol to give the pure material, mp 125° to 126.5° C.

To an ethyl acetate (10 ml) solution containing the above-obtained compound (1.0 g.), there was added a mixture of hydrobromic acid and acetic acid (volume ratio, 4:1) (2 ml), whereafter the mixture was stirred at ambient temperature for half an hour. The precipitating crystals were collected by filtration and washed with ethyl acetate to give 2-(4-phenacyloxyphenyl)glycine phenacyl ester hydrobromide (830 mg.), which was recrystallized from a mixture of ethanol, methanol and diethyl ether to obtain the pure material (0.55 g.), mp 176° to 177° C.

Thus obtained compound (9.5 g.) was reacted with 37% formaldehyde aqueous solution (6 ml) in substantially the same manner as one described in Example A-1 to give 1,3,5-tris(4-phenacyloxy-α-phenacyloxycarbonylbenzyl)-perhydro-1,3,5-triazine (7.25 g.), mp 80° to 90° C.

N M R (TMS)—δppm (CDCl₃): 3.70 (6H, s), 4.65 (3H, s), 5.19 (6H, s), 5.23 (6H, s), 6.86 to 8.04 (42H, m).

(B) For the Process 2

EXAMPLE B-1

Preparation of D-2-(4-benzyloxyphenyl)-N-methylthiomethylene-glycine benzyl ester A solution of triethylamine (3.9 g.) in anhydrous chloroform (10 ml.) was added dropwise to a solution of p-toluene sulfonate of D-2-(4-benzyloxyphenyl)glycine benzyl ester (20 g.) in anhydrous chloroform (400 ml.) with stirring under ice-cooling. To this mixture was added dropwise a solution of O-ethyl thioformate (5.21 g.) in anhydrous chloroform (10 ml.) at the same temperature, and then the mixture was kept stirring at an ambient temperature over night. The reaction mixture was poured into ice-water (400 ml) and the insoluble materials were filtered off. The organic layer was washed with 1% aqueous phosphoric acid and with water, respectively, dried over magnesium sulfate and then evaporated to dryness under reduced pressure. The residue (13.1 g.) was chromatographed on silica gel (100 g.) and eluted with benzene. The fractionated eluate containing the desired product was combined and evaporated under reduce pressure to give crystalline D-2-(4-benzyloxyphenyl)-N-thioformylglycine benzyl ester (3.66 g.), which was recrystallized from a mixture of benzene and n-hexane to give the pure material, m.p. 124°-126° C.

A mixture of D-2-(4-benzyloxyphenyl)-N-thioformylglycine benzyl ester (3.56 g.), potassium carbonate (0.63 g.) and methyl iodide (3.89 g.) in anhydrous acetone (35 ml.) was stirred at ambient temperature for 23 hours. The solid substances were filtered off and the filtrate was evaporated to dryness under reduced pressure. The residue was dissolved in chloroform, washed with water, dried over magnesium sulfate and then evaporated to dryness under reduced pressure to give crystalline mass, which was triturated with diisopropyl ether and collected by filtration to yield D-2-(4-benzyloxyphenyl)-N-methylthiomethyleneglycine benzyl ester (3.08 g.). Recrystallized from ethanol to give the pure material, m.p. 78°-80° C.

I R—νcm⁻¹ (Nujol): 1730, 1610.

N M R (TMS)—δppm (CDCl₃): 2.36 (3H, s), 5.00 (2H, s), 5.08 (1H, s), 5.10 (2H, s), 6.78 to 7.56 (14H, m), 8.25 (1H, s).

The following compounds (Examples B-2 and B-3) were prepared in substantially the same manner as one described in Example B-1.

EXAMPLE B-2

D-2-(4-Benzyloxyphenyl)-N-methylthiomethyleneglycine methyl ester.

N M R (TMS)—δppm (CDCl₃): 2.40 (3H, s), 3.65 (3H, s), 5.01 (1H, s), 5.06 (1H, s), 6.83 to 7.53 (9H, m), 8.28 (1H, s).

EXAMPLE B-3

D-N-Methylthiomethylene-2-phenylglycine methyl ester.

N M R (TMS)—δppm (CDCl₃): 2.36 (3H, s), 3.60 (3H, s), 5.03 (1H, s), 7.25 (5H, s), 8.20 (1H, s).

EXAMPLE B-4

Preparation of D-N-benzylidene-2-(4-hydroxyphenyl)glycine methyl ester:

A methanol (250 ml.) solution containing D-2-(4-hydroxyphenyl)glycine methyl ester (16.8 g.) and benzaldehyde (9.86 g.) was heated under reflux for an hour. The methanol was removed by distillation under reduced pressure to give a residue, which was dissolved in benzene (200 ml.) The precipitating crystals were collected by filtration and recrystallized from benzene to give D-N-benzylidene-2-(4-hydroxyphenyl)glycine methyl ester (21.0 g.), mp 128° C.

The following compounds (Examples B-5 and B-6) were prepared in substantially the same manner as one described in Example B-4.

EXAMPLE B-5

D-N-Benzylidene-2-phenylglycine methyl ester.

I R—νcm⁻¹ (Nujol): 1740, 1635.

EXAMPLE 37

2-(3-Amino-2-oxo-1-azetidinyl)-2-(2-furyl)acetic acid.
I R—$\nu$cm$^{-1}$ (Nujol): 1725, 1640.

EXAMPLE 38

Methyl 2-(3-amino-2-oxo-1-azetidinyl)-2-(1-naphthyl)acetate.
I R—$\nu$cm$^{-1}$ (film): 3380, 3000 (shoulder), 1740 (broad).

EXAMPLE 39

Methyl 2-(3-amino-2-oxo-1-azetidinyl)-2-(3-mesylaminophenyl)acetate.
I R—$\nu$cm$^{-1}$ (film): 3350 (shoulder), 3150 (broad), 1730 (broad).

EXAMPLE 40

Methyl erythro-2-(3-amino-2-oxo-1-azetidinyl)-3-methoxy-3-phenylpropionate.
I R—$\nu$cm$^{-1}$ (film): 3380, 1750.

EXAMPLE 41

Methyl 2-(3-amino-2-oxo-1-azetidinyl)-3-phenylthiopropionate.
I R—$\nu$cm$^{-1}$ (film): 3380, 3300 (shoulder), 1740 (broad).

EXAMPLE 42

Methyl 2-(3-amino-2-oxo-1-azetidinyl)-3-(phenylthio)acrylate.
I R—$\nu$cm$^{-1}$ (film): 3380, 3320 (shoulder), 1760, 1740, 1720.

EXAMPLE 43

Methyl 2-(3-amino-2-oxo-1-azetidinyl)-3-(4-hydroxyphenyl)propionate.
I R—$\nu$cm$^{-1}$ (film): 3200, 1750, 1720.

EXAMPLE 44

Methyl 2-(3-amino-2-oxo-1-azetidinyl)-3-(4-benzyloxyphenyl)propionate.
I R—$\nu$cm$^{-1}$ (Nujol): 3300, 1750, 1740, 1720.

EXAMPLE 45

Methyl 2-(3-amino-4-trans-styryl-2-oxo-1-azetidinyl)-2-phenylacetate (mixture of two cis isomers at the third and fourth positions of the azetidine ring).
I R—$\nu$cm$^{-1}$ (film): 3350, 1770, 1740, 1660.

EXAMPLE 46

N,N-Dimethyl-1,3-propanediamine (1.32 g.) was added to a mixture of methanol (30 ml.) and chloroform (18 ml.) containing 2-(2-oxo-3-phthalimido-1-azetidinyl)-2-(2-thienyl)acetate (2.22 g.), whereafter the mixture was stirred at ambient temperature overnight. After the reaction, the reaction mixture was evaporated to dryness under reduced pressure to give a residue, which was dissolved in ethyl acetate. The solution was extracted with three portions of an aqueous solution consisting of 1 N hydrochloric acid (6.4 ml.) and water (10 ml.). The combined aqueous extracts were adjusted to pH8 with sodium bicarbonate and then saturated with sodium chloride. The solution was extracted with ethyl acetate and the extract was washed with a saturated aqueous sodium chloride and then dried over magnesium sulfate. The solution was evaporated to dryness under reduced pressure to give a residue (1.57 g.), which was subjected to column chromatography on silica gel (25 g.). Elution was carried out with chloroform and the fractions containing a desired compound were collected. The solvent was removed by distillation from the solution under reduced pressure to give methyl 2-(3-amino-2-oxo-1-azetidinyl)-2-(2-thienyl)acetate (0.96 g.).
I R—$\nu$cm$^{-1}$ (film): 3390, 1765, 1740.
N M R (TMS)—$\delta$ppm (CDCl$_3$): 2.00 and 2.09 (2H, each s), 2.98 and 3.35 (1H, each d,d, J=2.5, 6Hz), 3.53 and 3.86 (1H, each t, J=6Hz), 3.73 (3H, s) 4.05 and 5.12 (1H, each d,d, J=2.5, 6Hz), 5.83 (1H, s), 6.75 to 7.55 (3H, m).

The following compounds (Examples 47 to 63) were obtained by reacting the corresponding compound having phthalimido group with N,N-dimethyl-1,3-propanediamine in substantially the same manner as one described in Example 46.

EXAMPLE 47

2-(3-Amino-2-oxo-1-azetidinyl)-2-(2-thienyl)acetic acid.
I R—$\nu$cm$^{-1}$ (Nujol): 2750 to 2250, 1760 (shoulder), 1745, 1620.
N M R—[internal standard: sodium 2,2,3,3-tetradeutero-3-(trimethylsilyl)propionate, hereinafter merely referred to as TMSP]—$\delta$ppm (D$_2$O): 3.13 and 3.45 (1H, each q, J=2Hz, 5Hz), 3.54 and 3.82 (1H, each t, J=5Hz), 4.21 and 4.31 (1H, each q, J=2Hz, 5Hz), 5.54 and 5.56 (1H, each s), 7.10 (2H, m), 7.46 (1H, m).

EXAMPLE 48

2-(3-Amino-2-oxo-1-azetidinyl)-2-(2-furyl)acetic acid
I R—$\nu$cm$^{-1}$ (Nujol): 1725, 1640.
N M R (TMSP)—$\delta$ppm (D$_2$O): 3.36 (1H, d,d, J=2Hz, 6Hz), 3.90 (1H, d,d, J=6Hz, 5Hz), 5.41 (1H, s), 6.49 (2H, m), 7.37 (1H, m).

EXAMPLE 49

Methyl 2-(3-amino-2-oxo-1-azetidinyl)-2-(1-naphthyl)acetate.
I R—$\nu$cm$^{-1}$ (film): 3380, 3000 (shoulder), 1740 (broad).
N M R (TMS)—$\delta$ppm (CDCl$_3$): 1.70 (2H, s), 2.48 and 3.37 (1H, each d,d, J=3Hz, 6Hz), 3.02 and 3.84 (1H, each d,d, J=3Hz, 6Hz), 3.91 and 4.21 (1H, each d,d, J=3Hz, 6Hz), 3.74 and 3.75 (3H, each s), 6.43 and 6.44 (1H, each s), 7.2 to 8.2 (7H, m).

EXAMPLE 50

Methyl 2-(3-amino-2-oxo-1-azetidinyl)-2-(3-mesylaminophenyl)acetate.
I R—$\nu$cm$^{-1}$ (film): 3350 (shoulder), 3150 (broad), 1730 (broad).

EXAMPLE 51

Methyl erythro-2-(3-amino-2-oxo-1-azetidinyl)-3-methoxy-3-phenylpropionate.
I R—$\nu$cm$^{-1}$ (film): 3380, 1750.
N M R (TMS)—$\delta$ppm (CDCl$_3$): 1.57 (2H, s), 3.23 and 3.32 (3H, each s), 3.71 and 3.78 (3H, each s), 4.65 (1H, d, J=5Hz), 4.85 (1H, d, J=5Hz), 7.36 (5H, s).

EXAMPLE 52

Methyl 2-(3-amino-2-oxo-1-azetidinyl)-3-phenylthiopropionate.
I R—$\nu$cm$^{-1}$ (film): 3380, 3300 (shoulder), 1740 (broad).

N M R (TMS)—δppm (CDCl₃): 2.98 to 3.76 (4H, m), 3.68 (3H, s), 4.04 and 4.15 (1H, each d,d, J=6Hz, 3Hz), 4.54 (1H, d,d, J=10Hz, 5Hz), 7.2 to 7.5 (5H, m).

EXAMPLE 53

Methyl 2-(3-amino-2-oxo-1-azetidinyl)-3-phenylthioacrylate.

I R—νcm⁻¹ (film): 3380, 3320 (shoulder), 1760, 1740, 1720.

N M R (TMS)—δppm (CDCl₃): 1.94 (2H, s), 3.55 (1H, d,d, J=6Hz, 3Hz), 3.76 (3H, s), 3.95 (1H, t, J=6Hz), 4.33 (1H, d,d, J=6Hz, 3Hz), 7.2 to 7.6 (6H, m).

EXAMPLE 54

Methyl 2-(3-amino-2-oxo-1-azetidinyl)-3-methyl-3-(5-methyl-1,3,4-thiadiazol-2-ylthiomethyl)acrylate (mixture of cis* and trans** isomers).

*Trans form:
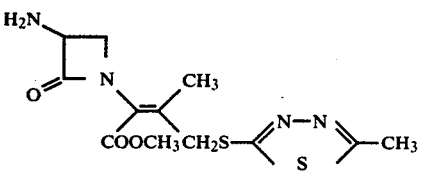

**Cis form:
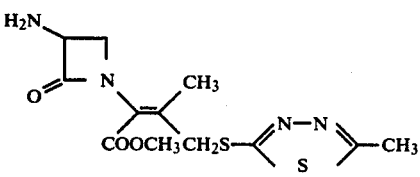

I R—νcm⁻¹ (film): 1780, 1760, 1720.

As shown in the above chemical structure, trans isomer is the one in which the methyl group on the third position and the azetidinone ring on the second position of the acrylate are the opposite sides of the double bond, and cis isomer is the one in which they are the same side of the double bond.

The above relationship of trans and cis isomers of such compounds is the same one in the following examples.

EXAMPLE 55

Methyl 2-(3-amino-2-oxo-1-azetidinyl)-3,3-bis(5-methyl-1,3,4-thiadiazol-2-ylthiomethyl)acrylate.

I R—νcm⁻¹ (film): 3400, 1780, 1760, 1720.

EXAMPLE 56

Methyl 2-(3-amino-2-oxo-1-azetidinyl)-3-(4-hydroxyphenyl)propionate.

I R—νcm⁻¹ (film): 3200, 1750, 1720.

EXAMPLE 57

Methyl 2-(3-amino-2-oxo-1-azetidinyl)-3-(4-benzyloxyphenyl)propionate.

I R—νcm⁻¹ (Nujol): 3300, 1750, 1740, 1720.

EXAMPLE 58

Methyl 2-(3-amino-4-methylthio-2-oxo-1-azetidinyl)-2-(4-benzyloxyphenyl)acetate (mixture of two trans isomers at the third and fourth positions of the azetidine ring).

I R—νcm⁻¹ (film): 3400, 1770, 1740.

EXAMPLE 59

Methyl 2-(3-amino-4-methylthio-2-oxo-1-azetidinyl)-2-phenylacetate (mixture of two trans isomers at the third and fourth positions of the azetidine ring).

I R—νcm⁻¹ (film): 3380, 1770, 1740.

EXAMPLE 60

Methyl 2-[3-amino-4-(5-methyl-1,3,4-thiadiazol-2-ylthio)-2-oxo-1-azetidinyl]-2-phenylacetate (mixture of two trans isomers at the third and fourth positions of the azetidine ring).

I R—νcm⁻¹ (film): 3280, 1770, 1640.

EXAMPLE 61

Methyl 2-[3-amino-4-(5-methyl-1,3,4-thiadiazol-2-ylthio)-2-oxo-1-azetidinyl]-2-phenylacetate (mixture of two cis isomers at the third and fourth positions of the azetidine ring).

I R—νcm⁻¹ (film): 3350, 1765, 1740.

EXAMPLE 62

Benzyl 2-(3-amino-4-methylthio-2-oxo-1-azetidinyl)-2-phenylacetate (mixture of two trans isomers at the third and fourth positions of the azetidine ring).

I R—νcm⁻¹ (film): 3400 to 3300, 1770, 1740, 1680.

EXAMPLE 63

Methyl 2-(3-amino-2-oxo-1-azetidinyl)-3-(2-benzothiazolylthiomethyl)-3-methylacrylate (mixture of cis and trans isomers).

I R—νcm⁻¹ (film): 1790, 1770, 1730, 1710.

EXAMPLE 64

Methyl 2-(3-amino-4-trans-styryl-2-oxo-1-azetidinyl)-2-phenylacetate was obtained by reacting methyl 2-(4-trans-styryl-2-oxo-3-phtholimido-1-azetidinyl)-2-phenylacetate with hydrozide (one hydrate) as amines in substantially the same manner as one described in Example 46.

I R—νcm⁻¹ (film): 3350, 1770, 1740, 1660.

N M R (TMS)—Γppm (CDCl₃): 1.78 (2H, broad s), 3.68 and 3.74 (3H, each s), 4.13 and 4.78 (1H, m and q, J=5Hz, 6Hz), 4.33 and 4.46 (1H, each d, J=5Hz), 5.52 and 5.60 (1H, each s), 6.24 to 6.54 (2H, m), 7.02 to 7.56 (10H, m).

EXAMPLE 65

A mixture of cis and trans isomers of methyl 3-methyl-3-(5-methyl-1,3,4-thiadiazol-2-ylthiomethyl)-2-(2-oxo-3-phthalimido-1-azetidinyl)acrylate (0.300 g.) was dissolved in ethanol (15 ml.) and to the solution, there was added an ethanol (0.1 ml.) solution containing methylamine (30 mg.). The reaction mixture was stirred at ambient temperature for 15 minutes. The reaction mixture was evaporated to dryness under reduced pressure to give a residue, which was dissolved in ethyl acetate. The solution was washed with water and then dried over magnesium sulfate. The solution was evaporated to dryness under reduced pressure to give an oily residue, which was subjected to column chromatography on silica gel (5 g.). Elution was carried out with chloroform, and trans isomer of methyl 2-[3-{2-(N-methylcarbamoyl)benzamido}-2-oxo-1-azetidinyl]-3-methyl-3-(5-methyl-1,3,4-thiadiazol-2-ylthiomethyl)acrylate was eluted first and cis isomer of the above desired compound (70 mg.) was eluted secondly. The yield of the thyleneglycine benzyl ester (2.67 g.) in methylene chloride (27 ml.) in 10 minutes with stirring under cooling at 0° to 5° C. After stirring for further 15 minutes at the same temperature, a solution of triethylamine (0.67 g.) in methylene chloride (10 ml.) was added dropwise to the mixture at ambient temperature and stirred for additional 40 minutes. The reaction mixture was washed with water, diluted hydrochloric acid, an aqueous sodium bicarbonate, water, dried over magnesium sulfate and evaporated to dryness under reduced pressure. The residue (3.69 g.) was chromatographed on silica gel (110 g.) and eluted with chloroform. The fractionated eluates were combined and evaporated to dryness to give oily benzyl D-2-(4-benzyloxyphenyl)-2-(4-methylthio-2-oxo-3-phthalimido-1-azetidinyl)acetate (3.15 g.), which was identified as an about 1:1.7 mixture of two 3,4-trans isomers (a) and (b).

I R—$\nu$ cm$^{-1}$ (film): 1780, 1770, 1740, 1720.

| NMR (TMS) $\delta$ppm (CDCl$_3$): Isomer (a); | Isomer (b) |
|---|---|
| 2.10 (3H, s) | |
| 4.69 (1H, d, J=2.5Hz) | 1.83 (3H, s) |
| 5.01 (2H, s) | 5.02 (2H, s) |
| 5.30 (1H, d, J=2.5Hz) | 5.29 (2H, s) |
| 5.57 (1H, s) | 5.40 (1H, s) |
| 6.69 to 7.52 (14H, m) | 6.69 to 7.52 (14H, m) |
| 7.56 to 7.94 (4H, m) | 7.56 to 7.94 (4H, m) |

The following compounds (Examples 18 to 29) were obtained by reacting the corresponding glycine derivatives with 2-substituted acetyl chloride in substantially the same manner as one described in Example 17.

EXAMPLE 18

Methyl D-2-(4-benzyloxyphenyl)-2-(4-methylthio-2-oxo-3-phthalimido-1-azetidinyl)acetate [mixture of two trans isomers (a) and (b) at the third and fourth positions of the azetidine ring, (about 2:1)].

I R—$\nu$ cm$^{-1}$ (film): 1780, 1770, 1740, 1720.

| NMR (TMS) $\delta$ppm (CDCl$_3$): Isomer (a); | Isomer (b); |
|---|---|
| 2.14 (3H, s) | 1.87 (3H, s) |
| 3.79 (3H, s) | 3.81 (3H, s) |
| 4.71 (1H, d, J=2.5Hz) | 5.05 (2H, s) |
| 5.04 (2H, s) | 5.30 (2H, s) |
| 5.33 (1H, d, J=2.5Hz) | 6.86 to 7.54 (9H, m) |
| 5.54 (1H, s) | 7.58 to 7.96 (4H, m) |
| 6.86 to 7.54 (9H, m) | |
| 7.58 to 7.96 (4H, m) | |

EXAMPLE 19

Methyl 2-(3-azido-4-methylthio-2-oxo-1-azetidinyl)-2-phenylacetate [mixture of two trans isomers (a) and (b) at the third and fourth positions of the azetidine ring].

I R—$\nu$ cm$^{-1}$ (film): 2120, 1778, 1750.

| NMR (TMS) $\delta$ppm (CDCl$_3$): Isomer (a); | Isomer (b); |
|---|---|
| 1.73 (3H, s) | 1.98 (3H, s) |
| 3.74 (3H, s) | 3.74 (3H, s) |
| 4.54 (1H, d, J=2Hz) | 4.38 (1H, d, J=2Hz) |
| 4.82 (1H, d, J=2Hz) | 4.54 (1H, d, J=2Hz) |
| 5.40 (1H, s) | 5.28 (1H, s) |
| 7.40 (5H, s) | 7.38 (5H, s) |

EXAMPLE 20

Benzyl 2-(3-azido-4-methylthio-2-oxo-1-azetidinyl)-2-phenylacetate [mixture of two trans isomers (a) and (b) at the third and fourth positions of the azetidine ring].

I R—$\nu$ cm$^{-1}$ (film): 2110, 1780, 1740.

| NMR (TMS) $\delta$ppm (CDCl$_3$): Isomer (a); | Isomer (b); |
|---|---|
| 1.67 (3H, s) | 1.93 (3H, s) |
| 4.45 (1H, d, J=2Hz) | 4.33 (1H, d, J=2Hz) |
| 4.80 (1H, d, J=2Hz) | 4.48 (1H, d, J=2Hz) |
| 5.26 (2H, s) | 5.26 (2H, s) |
| 5.43 (1H, s) | 5.30 (1H, s) |
| 7.30 (5H, s) | 7.27 (5H, s) |
| 7.35 (5H, s) | 7.32 (5H, s) |

EXAMPLE 21

Methyl 2-(3-azido-4-methylthio-2-oxo-1-azetidinyl)-2-(4-benzyloxyphenyl)acetate [mixture of two isomers (a) and (b) at the third and fourth positions of the azetidine ring].

I R—$\nu$ cm$^{-1}$ (film): 2120, 1775, 1745.

| NMR (TMS) $\delta$ppm (CDCl$_3$) Isomer (a); | Isomer (b); |
|---|---|
| 1.74 (3H, s) | 2.00 (3H, s) |
| 3.76 (3H, s) | 3.76 (3H, s) |
| 4.49 (1H, d, J=2Hz) | 4.36 (1H, d, J=2Hz) |
| 4.80 (1H, d, J=2Hz) | 4.49 (1H, d, J=2Hz) |
| 5.04 (2H, s) | 5.04 (2H, s) |
| 5.24 (1H, s) | 5.24 (1H, s) |
| 6.92 to 7.56 (9H, m) | 6.92 to 7.56 (9H, m) |

EXAMPLE 22

Methyl 2-(3-azido-2-oxo-4-phenyl-1-azetidinyl)-2-phenylacetate (mixture of stereoisomers).

I R—$\nu$ cm$^{-1}$ (film): 2100, 1770, 1740.

EXAMPLE 23

Methyl 2-(3-benzyloxycarbonylamino-2-oxo-4-phenyl-1-azetidinyl)-2-phenylacetate (mixture of stereoisomers).

I R—$\nu$ cm$^{-1}$ (film): 3320, 1770, 1740, 1720.

N M R (TMS)—$\delta$ ppm (CDCl$_3$): 3.56, 3.70 (3H, each s), 4.86 (2H, s), 5.08 to 5.52 (2H, m), 5.52 (1H, s), 6.68 to 7.50 (15H, m).

EXAMPLE 24

Methyl 2-(2-oxo-3-phenoxy-4-phenyl-1-azetidinyl)-2-phenylacetate (mixture of stereoisomers).

I R—$\nu$ cm$^{-1}$ (film): 1770, 1740.

EXAMPLE 25

Methyl D-2-(3-azido-2-oxo-4-azetidinyl)-2-(4-hydroxyphenyl)acetate [mixture of two cis isomers (a)

and (b) at the third and fourth positions of the azetidine ring].

Isomer (a); mp 138° to 142° C.
I R—ν cm$^{-1}$ (CHCl$_3$): 3300, 2120, 1765, 1745.
N M R (TMS)—δ ppm (CDCl$_3$): 3.67 (3H, s), 4.94 (1H, d, J=5 Hz), 5.06 (1H, d, J=5 Hz), 5.38 (1H, s), 6.56 (2H, d, J=8 Hz), 6.90 (2H, d, J=8 Hz), 7.12 (5H, m).

Isomer (b); mp 67° to 71° C.
I R—ν cm$^{-1}$ (CHCl$_3$): 3300, 2120, 1765, 1750.
N M R (TMS)—δ ppm (CDCl$_3$): 3.60 (3H, s), 4.82 (1H, d, J=5 Hz), 4.90 (1H, d, J=5 Hz), 5.12 (1H, s), 6.72 (2H, d, J=8 Hz), 7.08 (2H, d, J=8 Hz), 7.36 (5H, s).

EXAMPLE 26

Methyl D-2-[4-trans-styryl-2-oxo-3-phthalimido-1-azetidinyl]-2-phenylacetate (mixture of two cis isomers at the third and fourth positions of the azetidine ring), mp 144° to 145° C.
I R—ν cm$^{-1}$ (Nujol): 1770, 1740 (shoulder), 1720.

EXAMPLE 27

Methyl D-2-[3-azido-4-trans-styryl-2-oxo-1-azetidinyl]-2-phenylacetate (mixture of two cis isomers at the third and fourth positions of the azetidine ring).
I R—ν cm$^{-1}$ (film): 2120, 1780, 1770, 1750.
N M R (TMS)—δ ppm (CDCl$_3$): 3.68, 3.75 (3H, each s), 4.12 to 4.94 (2H, m), 5.48, 5.60 (1H, each s), 6.28 to 6.52 (2H, m), 7.36 (5H, s).

EXAMPLE 28

Methyl 2-(3-azido-2-oxo-4-phenyl-1-azetidinyl)-2-phenylacetate (one of two trans isomers) was obtained in the presence of boron trifluoride diethyl etherate in substantially the same manner as one described in Example 17.
I R—νcm$^{-1}$ (film): 2120, 1770, 1740.
N M R (TMS)—ppm (CDCl$_3$): 3.59 (3H, s), 4.30 (1H, d, J=2.5 Hz), 4.35 (1H, d, J=2.5 Hz), 5.22 (1H, s), 6.84 to 7.55 (10H, m).

EXAMPLE 29

Methyl 2-[3-azido-4-(5-methyl-1,3,4-thiadiazol-2-ylthio)-2-oxo-1-azetidinyl]-2-phenylacetate (mixture of two trans isomers at the thid and fourth positions of the azetidine ring), mp 81° to 84° C.

EXAMPLE 30

Methyl D-2-(3-azido-2-oxo-1-azetidinyl)-2-(2-thienyl)acetate (3.4 g.) was dissolved in dioxane (34 ml.), and to the solution, there was added 10% palladium on carbon (1.7 g.) as a catalyst. The reaction mixtue was subjected to catalytic reduction at ordinary temperature for 3 hours using a medium-pressure apparatus in a stream of hydrogen gas. The catalyst was removed by filtration and the filtrate was evaporated to dryness under reduced pressure to give an oily residue (2.98 g.), which was subjected to column chromatography on silica gel (50 g.). Elution was carried out with chloroform and the fractions containing a desired compound were collected. The solvent was removed by distillation from the eluate under reduced pressure to give methyl D-2-(3-amino-2-oxo-1-azetidinyl)-2-(2-thienyl)acetate (mixture of two isomers at the third position of the azetidine ring, 2.60 g.).
I R—νcm$^{-1}$ (film): 3390, 1765, 1740.

The following compounds (Examples 31 to 45) were obtained by subjecting the corresponding compounds having azido group to reduction in substantially the same manner as one described in Example 30.

EXAMPLE 31

Methyl 2-(3-amino-4-methylthio-2-oxo-1-azetidinyl)-2-(4-benzyloxyphenyl)acetate [mixture of two trans isomers (a) and (b) at the third and fourth positions of the azetidine ring].
I R—νcm$^{-1}$ (film): 3400, 1770, 1740.

| NMR δppm (CDCl$_3$): Isomer (a); | Isomer (b); |
|---|---|
| 1.71 (2H, s) | 1.72 (3H, s) |
| 2.01 (3H, s) | 1.80 (2H, s) |
| 3.78 (3H, s) | 3.78 (3H, s) |
| 4.03 to 4.28 (2H, m) | 4.15 (1H, d, J=2Hz) |
| 5.07 (2H, s) | 4.63 (1H, d, J=2Hz) |
| 5.23 (1H, s) | 5.07 (2H, s) |
| 6.80 to 7.60 (9H, m) | 5.37 (1H, s) |
|  | 6.80 to 7.60 (9H, m) |

EXAMPLE 32

Methyl 2-(3-amino-4-methylthio-2-oxo-1-azetidinyl)-2-phenylacetate [mixture of two trans isomers (a) and (b) at the third and fourth positions of the azetidine ring].
I R—νcm$^{-1}$ (film): 3380, 1770, 1740.

| NMR (TMS) δppm (CDCl$_3$): Isomer (a); | Isomer (b); |
|---|---|
| 1.95 (2H, s) | 1.70 (3H, s) |
| 1.98 (3H, s) | 1.80 (2H, s) |
| 3.70 (3H, s) | 3.74 (3H, s) |
| 4.00 to 4.24 (2H, m) | 4.05 (1H, d, J=2Hz) |
| 5.18 (1H, s) | 4.56 (1H, d, J=2Hz) |
| 7.30 (5H, s) | 5.34 (1H, s) |
|  | 7.30 (5H, s) |

EXAMPLE 33

Methyl 2-[3-amino-4-(5-methyl-1,3,4-thiadiazol-2-ylthio)-2-oxo-1-azetidinyl]-2-phenylacetate (mixture of two trans isomers at the third and fourth positions of the azetidine ring).
I R—νcm$^{-1}$ (film): 3280, 1770, 1640.

EXAMPLE 34

Methyl 2-[3-amino-4-(5-methyl-1,3,4-thiadiazol-2-ylthio)-2-oxo-1-azetidinyl]-2-phenylacetate (mixture of two cis isomers at the third and fourth positions of the azetidine ring).
I R—νcm$^{-1}$ (film): 3350, 1765, 1740.

EXAMPLE 35

Benzyl 2-(3-amino-4-methylthio-2-oxo-1-azetidinyl)-2-phenylacetate (mixture of two trans isomers at the third and fourth positions of the azetidine ring).
I R—νcm$^{-1}$ (film): 3400 to 3300, 1770, 1740, 1680.

EXAMPLE 36

2-(3-Amino-2-oxo-1-azetidinyl)-2-(2-thienyl)acetic acid.
I R—νcm$^{-1}$ (Nujol): 2750 to 2250, 1760 (shoulder), 1745, 1620.

above trans isomer is 95 mg and that of the above cis isomer is 70 mg.

Trans isomers;

I R—νcm$^{-1}$ (film): 1780, 1760, 1730, 1660.

N M R (TMS)—δppm (CD$_3$OD): 2.29 (3H, s), 2.70 (3H, s), 2.88 (3H, s), 3.82 (3H, s), 3.84 to 4.00 (2H, m), 4.24, 4.50 (2H, AB-q, J=14Hz), 5.08, 5.12 (1H, d,d J=4Hz), 7.50 to 7.72 (4H, s).

Cis isomer;

I R—νcm$^{-1}$ (film): 1790, 1770, 1730, 1660.

N M R (TMS)—δppm (CD$_3$OD): 2.18 (3H, s), 2.74 (3H, s), 2.90 (3H, s), 3.82 (3H, s), 3.72 to 3.88 (2H, m), 4.52 (2H, s), 5.06, 5.10 (1H, d,d, J=5Hz), 7.60 (4H, s).

EXAMPLE 66

0.1 N Aqueous sodium hydroxide (10 ml.) was added to a methanol (10 ml.) solution containing a mixture of cis and trans isomers of methyl 3-methyl-3-(5-methyl-1,3,4-thiadiazol-2-ylthiomethyl)-2-(2-oxo-3-phthalimido-1-azetidinyl)acrylate (0.470 g.) at 0° to 5° C., and then the mixture was stirred at the same temperature for 10 minutes. After the reaction, the methanol was removed from the reaction mixture under reduced pressure to give an aqueous solution, which was adjusted to pH 2 to 3 with dilute hydrochloric acid. The aqueous solution was extracted with ethyl acetate. The extract was washed with water and then dried over magnesium sulfate. The solution was evaporated to dryness under reduced pressure to give a residue, which was subjected to column chromatography on silica gel (10 g.). Elution was carried out with a mixture of chloroform and methanol (volume ratio, 100:2) and a trans isomer of methyl 2-[3-(2-carboxylbenzamido)-2-oxo-1-azetidinyl]-3-methyl-3-(5-methyl-1,3,4-thiadiazol-2-ylthiomethyl)acrylate (105 mg.) was eluted first, and trans and cis isomers of the above desired compound (140 mg.) was successively eluted and then a cis isomer of the above compound (97 mg.) was eluted next.

Trans isomer;

I R—νcm$^{-1}$ (film): 1780, 1760, 1720, 1660.

N M R (TMS)—δppm (CD$_3$OD): 2.30 (3H, s), 2.72 (3H, s), 3.82 (3H, s), 3.84 to 4.00 (2H, m), 4.24 to 4.48 (2H, AB-q, J=12Hz), 5.07, 5.12 (1H, d,d, J=5Hz), 7.50 to 8.08 (4H, m).

Cis isomer;

I R—νcm$^{-1}$ (film): 1780, 1760, 1710, 1660.

N M R (TMS)—δppm (CD$_3$OD): 2.17 (3H, s), 2.71 (3H, s), 3.78 (3H, s), 3.88 (2H, d, J=4Hz), 4.48 (2H, s), 5.03 (1H, t), 7.46 to 8.06 (4H, m).

EXAMPLE 67

2-(3-Amino-2-oxo-1-azetidinyl)-2-(2-thienyl)acetic acid (380 mg.) was suspended in dichloromethane (15 ml.), and to the suspension, there were added bis(trimethylsilyl) acetamide (0.60 g.) and N,N-dimethylformamide (0.25 ml.). The mixture was stirred at ambient temperature for 6 hours and insoluble materials were filtered off from the mixture, and to the filtrate, there was added bis(trimethylsilyl) acetamide (0.20 g.), whereafter the mixture was stirred for half an hour to prepare a dichloromethane solution. In the other hand, 4-(3-tert-butoxycarbonylamino-3-methoxycarbonyl-propoxy)phenylglyoxylic acid (0.440 g.) was suspended in dichloromethane (10 ml.), and to the suspension, there were added triethylamine (0.120 g.) and N,N-dimethylbenzylamine (two drops). The mixture was stirred for a while to dissolve it, and a dichloromethane solution (5 ml.) containing ethyl chloroformate (0.125 g.) was added dropwise to the solution at −60° C. in the course of 3 minutes, whereafter the mixture was stirred at the same temperature for 5 minutes and then at −20° to −15° C. for 20 minutes to dissolve it. To this solution, there was dropwise added the dichloromethane solution, prepared above, at −60° C. in the course of 20 minutes, whereafter the mixture was stirred at the same temperature for half an hour, and then at −15° C. for half an hour. The stirring was continued at 0° C. for an hour and at 20° to 25° C. for additional 1.5 hours. The reaction mixture was evaporated to dryness under reduced pressure to give a residue, which was dissolved in an aqueous sodium bicarbonate. The resultant aqueous solution was washed with diethyl ether, adjusted to pH 5.5 with dilute hydrochloric acid and then washed with ethyl acetate. The aqueous solution was adjusted to pH 5.5 with dilute hydrochloric acid and extracted with ethyl acetate. The extract was evaporated to dryness under reduced pressure to give 2-[3{4-(3-tert-butyoxycarbonylamino-3-methoxycarbonylpropoxy)phenylglyoxyloylamino}-2-oxo-1-azetidinyl]-2-(2-thienyl)acetic acid (0.100 g.).

I R—νcm$^{-1}$ (film): 3450 to 3300, 1760, 1730, 1710, 1680 to 1660.

N M R (TMS)—δppm (CDCl$_3$): 1.41 (9H, s), 2.12 to 2.34 (2H, m), 3.30 to 4.18 (4H, m), 3.72 (3H, s), 4.36 to 4.51 (1H, m), 5.86 (1H, broad s), 7.92 (1H, d, J=8Hz), 6.80 to 8.28 (7H, m).

The following compounds (Examples 68 to 77) were obtained by reacting the corresponding compound having amino group with the corresponding acrylating agent in substantially the same manner as one described in Example 67.

EXAMPLE 68

Methyl 2-[3-[4-{3-tert-butoxycarbonylamino-3-(4-methoxybenzyloxycarbonyl)propoxy}phenylglyoxyloylamino]-2-oxo-1-azetidinyl]-2-(2-thienyl)acetate.

I R—νcm$^{-1}$ (film): 3450 to 3350, 1760, 1740 1710, 1690, 1660.

N M R (TMS)—δppm (CDCl$_3$): 1.40 (9H, s), 2.18 to 2.38 (2H, m), 3.34 to 4.20 (4H, m), 3.78 and 3.80 (3H, s), 4.40 to 4.60 (1H, m), 5.12 (2H, s), 5.36 to 5.43 (1H, m), 5.94 (1H, s), 7.91 and 8.03 (1H, d, J=8Hz), 6.78 to 8.40 (11H, m).

EXAMPLE 69

2-[L-3-(D-N-Benxyloxycarbonyl-2-phenyl-glycinamido)-2-oxo-1-azetidinyl]-2-(2-thienyl)acetic acid(mixture of L and D forms at the second position of the acetic acid).

This compound was subjected to column chromatography for isolation of said isomers to give each of L and D forms of the above compound.

L form;

I R—νcm$^{-1}$ (film): 3300, 2550, 1740, 1715, 1670.

N M R (TMS)—δppm (CD$_3$OD): 3.48 (2H, m), 4.92 (1H, d,d, J=2.5Hz, 5Hz), 5.04 (2H, s), 5.27 (1H, s), 5.81 (1H, s), 6.92 to 7.56 (13H, m).

D form;

mp 159° to 163° C.

I R—νcm$^{-1}$ (Nujol): 3320, 3250 2600, 1740, 1705, 1665.

N M R (TMS)—δppm (CD$_3$OD): 3.14 (1H, d,d J=2.5Hz, 5Hz), 3.75 (1H, t, J=5Hz), 4.90 (1H, d,d, J=2.5Hz, 5Hz), 5.02 (2H, s), 5.28 (1H, s) 5.80 (1H, s), 6.84 to 7.56 (13H, m).

EXAMPLE 70

Methyl 3,3-bis(5-methyl-1,3,4-thiadiazol-2-ylthiomethyl)-2-[2-oxo-3-(2-phenoxyacetamido)-1-azetidinyl]acrylate.

I R—$\nu$cm$^{-1}$ (film): 3350, 1770, 1720, 1670.

N M R (TMS)—$\delta$ppm (CDCl$_3$): 2.60 (3H, s), 2.70 (3H, s), 3.80 (3H, s). 3.64, 3.66 (1H, d,d, J=2Hz, 5Hz), 3.86 (1H, t, J=5Hz), 4.54 (2H, s), 4.30, 4.66 (2H, AB-q, J=8Hz), 5.24 to 5.42 (1H, m), 7.36 to 7.82 (5H, m), 7.96 (1H, d, J=8Hz).

EXAMPLE 71

Methyl 3,3-bis(5-methyl-1,3,4-thiadiazol-2-ylthiomethyl)-2-[2-oxo-3-{2-(2-thienyl)acetamido}-1-azetidinyl]acrylate.

I R—$\nu$cm$^{-1}$ (Nujol): 3400, 1760, 1720, 1680.

N M R (TMS)—$\delta$ppm (CDCl$_3$): 3.73 (6H, s), 3.85 (3H, s), 3.23 to 4.00 (2H, m), 4.62 (2H, s), 4.27, 4.73 (2H, AB-q, J=14Hz), 5.13 to 5.40 (1H, m), 6.93 to 7.33 (3H, m), 7.85 (1H, d, J=8Hz).

EXAMPLE 72

Methyl 2-[4-methylthio-2-oxo-3-(2-phenylacetamide)-1-azetidinyl]-2-(4-benzyloxyphenyl)acetate (mixture of two trans isomers at the third and fourth positions of the azetidine ring).

I R—$\nu$cm$^{-1}$ (film): 3300, 1770, 1750, 1670.

N M R (TMS)—$\delta$ppm (CDCl$_3$): 1.82 and 2.05 (3H, each s), 3.60 (2H, s), 3.78 (3H, s), 4.40 to 4.98 (2H, m), 5.12 (2H, s), 5.30 and 5.35 (1H, each s), 6.50 (1H, d, J=8Hz), 6.85 to 7.62 (14H, m).

EXAMPLE 73

Methyl 2-[4-methylthio-2-oxo-3-{2-(2-thienyl)acetamido}-1-azetidinyl]-2-phenylacetate[mixture of two trans isomers (a) and (b) at the third and fourth positions of the azetidine ring].

I R—$\nu$cm$^{-1}$ (Nujol): 3250, 1770, 1750, 1660.

NMR (TMS) $\delta$ppm (CDCL$_3$):

| Isomer (a); | Isomer (b); |
| --- | --- |
| 2.04 (3H, s) | 1.78 (3H, s) |
| 3.76 (5H, s) | 3.76 (5H, s) |
| 4.44 (1H, d, J=2Hz) | 4.53 to 4.84 (2H, m) |
| 4.87 (1H, d, J=2Hz, 7Hz) | 5.35 (1H, s) |
| 5.30 (1H, s) | 6.63 (1H, d, J=7Hz) |
| 6.63 (1H, d, J=7Hz) | 6.80 to 7.69 (8H, m) |
| 6.80 to 7.69 (8H, m) | |

EXAMPLE 74

Methyl 2-[4-(5-methyl-1,3,4-thiadiazol-2-ylthio)-2-oxo-3-{2-(2-thienyl)acetamido}-1-azetidinyl]-2-phenylacetate (mixture of two cis isomers at the third and fourth positions of the azetidine ring).

I R—$\nu$cm$^{-1}$ (film): 3300, 1780, 1745, 1680.

N M R (TMS)—$\delta$ppm (CDCl$_3$): 2.60 and 2.63 (3H, each s), 3.65 (2H, s), 3.72 (3H, s), 5.05 to 5.90 (3H, m), 6.40 to 7.75 (9H, m).

EXAMPLE 75

Methyl 2-[4-(5-methyl-1,3,4-thiadiazol-2-ylthio)-2-oxo-3-{2-(2-thienyl)acetamido}-1-azetidinyl]-2-phenylacetate (mixture of two trans isomers at the third and fourth positions of the azetidine ring).

I R—$\nu$cm$^{-1}$ (film): 1785, 1750, 1670.

N M R (TMS)—$\delta$ppm (CDCl$_3$): 2.65 (3H, s), 3.74 (3H, s), 3.78 (2H, s), 4.68 to 5.72 (2H, m), 5.34 and 5.54 (1H, each s), 6.64 to 7.40 (8H, m).

EXAMPLE 76

Methyl 2-[4-methylthio-2-oxo-3-(2-phenylacetamido)-1-azetidinyl]-2-phenylacetate [mixture of two trans isomers (a) and (b) at the third and fourth positions of the azetidine ring].

I R—$\nu$cm$^{-1}$ (Nujol): 3290, 1785, 1770 (shoulder), 1760, 1665.

NMR (TMS) $\delta$ppm (CDCl$_3$):

| Isomer (a); | Isomer (b); |
| --- | --- |
| 1.93 (3H, s) | 1.76 (3H, s) |
| 3.50 (2H, s) | 3.51 (2H, s) |
| 3.71 (3H, s) | 3.71 (3H, s) |
| 4.46 (1H, d, J=2Hz) | 4.73 to 4.88 (2H, m) |
| 4.90 (1H, q, J=2Hz, 6Hz) | 5.39 (1H, s) |
| 5.33 (1H, s) | 6.90 (1H, d, J=6Hz) |
| 6.90 (1H, d, J=6Hz) | 7.04 to 7.50 (10H, m) |
| 7.04 to 7.50 (10H, m) | |

EXAMPLE 77

Benzyl 2-[4-methylthio-2-oxo-3-(2-phenylacetamido)-1-azetidinyl]-2-phenylacetate [mixture of two trans isomers (a) and (b) at the third and fourth positions of the azetidine ring].

I R—$\nu$cm$^{-1}$ (film): 3300, 1770, 1740, 1670.

NMR (TMS) $\delta$ppm (CDCl$_3$)

| Isomer (a); | Isomer (b); |
| --- | --- |
| 1.72 (3H, s) | 1.93 (3H, s) |
| 3.53 (2H, s) | 3.50 (2H, s) |
| 4.42 (1H, d, J=2Hz) | 4.41 (1H, d, J=2Hz) |
| 4.82 (1H, d, J=2Hz) | 4.85 (1H, d, J=2Hz) |
| 5.16 (2H, s) | 5.18 (2H, s) |
| 5.33 (1H, s) | 5.23 (1H, s) |
| 7.23 to 7.33 (15H, m) | 7.23 to 7.33 (15H, m) |

EXAMPLE 78

Methyl 2-[3-(N-mesyl-N-phenylglyoxyloylamino)-phenyl]-2-(2-oxo-3-phenylglyoxyloylamino-1-azetidinyl)acetate was obtained by reacting methyl 2-(3-amino-2-oxo-1-azetidinyl)-2-(3-mesylaminophenyl)acetate with phenylglyoxyolyl chloride in substantially the same manner as one described in Example 67.

I R—$\nu$cm$^{-1}$ (film): 3380, 1750, 1670.

N M R (TMS)—$\delta$ppm (CDCl$_3$): 3.34 and 3.40 (3H, each s), 3.71 and 3.75 (3H, each s), 3.22 to 3.90 (3H,m), 5.07 (1H, m), 5.65 and 5.75 (1H, s), 7.3 to 8.3 (9H, m).

EXAMPLE 79

2-(2,2-Dichloroacetoxyimino)-2-phenylacetic acid (660 mg.) was suspended in dichloromethane (5 ml.), and to the suspension, there was added phosphorus pentachloride (950 mg.), whereafter the mixture was stirred at ambient temperature for 40 minutes. The reaction mixture was evaporated to dryness under reduced pressure to give a residue, and then benzene was added thereto. The benzene was removed by distillation from the solution under reduced pressure to give a residue of the above acid chloride, which was dissolved in dichloromethane (5 ml.). This solution was added dropwise to a dichloromethane (10 ml.) solution containing methyl 2-(3-amino-2-oxo-1-azetidinyl)-3-(phenylthio)propionate (450 mg.) and bis-(trimethylsilyl)acetamide (3.25 g.) at −27° to −20° C. in the course of 5 minutes with stirring. The stirring was continued at −38° to −25° C. for additional 50 minutes.

Water (20 ml.) was poured into the reaction mixture and the resulting mixture was adjusted to pH 8 with a saturated aqueous sodium bicarbonate. The dichloromethane layer was separated from the above mixture, washed with four portions of dilute hydrochloric acid, aqueous sodium bicarbonate and water in turn, and then dried over magnesium sulfate. The solvent was removed by distillation from the solution under reduced pressure to give a residue, which was subjected to column chromatography on silica gel (15 g.). Elution was carried out with chloroform, and a mixture of chloroform and methanol (volume ratio, 100:1), and the fractions containing a desired compound were collected. The solvent was removed by distillation from the eluate under reduced pressure to give methyl 2-[3-(2-hydroxyimino-2-phenylacetamido)-2-oxo-1-azetidinyl]-3-(phenylthio)propionate (230 g.), mp 163° to 169° C.

I R—$\nu$cm$^{-1}$ (Nujol): 3480, 1760, 1730, 1670.

N M R (TMS)—$\delta$ppm [(CD$_3$)$_2$CO]: 3.36 to 3.90 (4H, m), 3.66 (3H, s), 4.50 (1H, m), 5.12 (1H, m), 7.2 to 7.7 (10H, m).

The following compounds (Examples 80 to 89) were obtained by reacting the corresponding compound having amino group with 2-(2,2-dichloroacetoxyimino)-2-phenylacetyl chloride in substantially the same manner as one described in Example 79.

EXAMPLE 80

Methyl 2-[3-(2-hydroxyimino-2-phenylacetamido-2-oxo-1-azetidinyl]-3-(phenylthio)acrylate.

I R—$\nu$cm$^{-1}$ (Nujol): 1750, 1710, 1660.

N M R (TMS)—$\delta$ppm [(CD$_3$)$_2$ CO]: 3.76 (3H, s), 3.9 to 4.2 (2H, m), 5.40 (1H, m), 7.3 to 7.7 (10H, m), 8.49 (1H, d, J=8 Hz).

EXAMPLE 81

Methyl erythro-2-[3-(2-hydroxyimino-2-phenylacetamido)-2-oxo-1-azetidinyl]-3-methoxy-3-phenylpropionate, mp 173° to 176° C. (dec.).

I R—$\nu$cm$^{-1}$ (Nujol): 3300, 1725, 1665.

N M R (TMS)—$\delta$ppm [(CD$_3$)$_2$ CO]: 3.27 (3H, s), 3.73 (3H, s), 3.6 to 3.7 (1H, m), 4.09 (1H, t, J=6 Hz), 4.61 (1H, d, J=5 Hz), 4.89 (1H, d, J=5 Hz), 5.24 (1H, d,d,d, J=3 Hz, 6 Hz, 7 Hz), 7.2 to 7.7 (12H, m), 8.25 (1H, d, J=7 Hz), 10.73 (1H, s).

EXAMPLE 82

Methyl 2-[3-(2-hydroxyimino-2-phenylacetamido)-2-oxo-1-azetidinyl]-2-(2-thienyl)acetate, mp 174° to 178° C. (dec.).

I R—$\nu$cm$^{-1}$ (Nujol): 3300, 1755, 1730, 1665.

N M R (TMS)—$\delta$ppm [(CD$_3$)$_2$CO]: 3.48 (1H, d,d, J=2.5 Hz, 6 Hz), 3.98 (1H, t, J=6 Hz), 5.12 (1H, m), 5.88 (1H, s), 6.93 to 7.83 (8H, m).

EXAMPLE 83

Methyl 2-[3-(2-hydroxyimino-2-phenylacetamido)-2-oxo-1-azetidinyl]-2-(1-naphthyl)acetate.

I R—$\nu$cm$^{-1}$ (film): 3250, 1740, 1660.

Mass spectrum—m/e 431 (M$^+$).

EXAMPLE 84

Methyl 2-[3-(2-hydroxyimino-2-phenylacetamido)-2-oxo-1-azetidinyl]-3-methyl-3-(5-methyl-1,3,4-thiadiazol-2-ylthiomethylacrylate) (mixture of trans and cis isomers).

This compound was subjected to column chromatography for isolation of said isomers to give each of cis and trans isomers of the above compound.

Trans isomer;

I R—$\nu$cm$^{-1}$ (film): 3300, 1760, 1730, 1670.

N M R (TMS)—$\delta$ppm (CDCl$_3$): 2.22 (3H, s), 2.52 (3H, s), 3.70 (3H, s), 3.62 to 3.92 (2H, m), 4.08 to 4.40 (2H, m), 4.08 to 4.40 (2H, AB-q, J=14 Hz), 5.15 to 5.32 (1H, m), 7.04 to 7.56 (5H, m), 8.04 (1H, d, J=8 Hz).

Cis isomer;

I R—$\nu$cm$^{-1}$ (film): 3300, 1770, 1730, 1670.

N M R (TMS)—$\delta$ppm (CDCl$_3$): 2.08 (3H, s), 2.66 (3H, s), 3.70 (3H, s), 3.72 to 3.92 (2H, m), 4.36 (2H, s), 4.92 to 5.06 (1H, m), 7.24 to 7.52 (5H, m), 7.82 (1H, d, J=6 Hz).

EXAMPLE 85

Methyl 3-(2-benzothiazolylthiomethyl)-2-[3-(2-hydroxyimino-2-phenylacetamido)-2-oxo-1-azetidinyl]-3-methylacrylate (mixture of trans and cis isomers).

I R—$\nu$cm$^{-1}$ (film): 3250, 1760, 1720, 1670.

N M R (TMS)—$\delta$ppm (CDCl$_3$): 2.10 and 2.24 (3H, each s), 3.66 and 3.68 (3H, each s), 5.04 to 5.20 and 4.92 to 5.08 (1H, each m), 7.22 to 7.80 (9H, m).

EXAMPLE 86

2-[3-(2-Hydroxyimino-2-phenylacetamido)-2-oxo-1-azetidinyl]-2-(2-furyl)acetic acid.

I R—$\nu$cm$^{-1}$ (Nujol): 3300, 1755, 1735, 1710, 1660.

N M R (TMS)—$\delta$ppm [(CD$_3$)$_2$CO]: 3.41 (1H, d,d, J=3 Hz, 6 Hz), 3.99 (1H, t, J=5 Hz), 5.25 (1H, m), 5.71 (1H, s), 6.46 (1H, m), 6.58 (1H, d, J=3 Hz), 7.3 to 7.7 (6H, m), 8.20 (1H, m).

EXAMPLE 87

Methyl 2-[3-(2-hydroxyimino-2-phenylacetamido)-2-oxo-1-azetidinyl]-3-(4-hydroxyphenyl)propionate.

I R—$\nu$cm$^{-1}$ (Nujol): 3230, 1750, 1725, 1642.

EXAMPLE 88

Methyl D-2-[4-trans-styryl-3-(2-hydroxyimino-2-phenylacetamido)-2-oxo-1-azetidinyl]-2-phenylacetate (mixture of two cis isomers at the third and fourth positions of the azetidine ring).

I R—$\nu$cm$^{-1}$ (film): 3350, 1770 to 1740, 1670.

EXAMPLE 89

Methyl D-2-[3-(2-hydroxyimino-2-phenylacetamido)-4-hydroxymethyl-2-oxo-1-azetidinyl]-2-phenylacetate (mixture of two cis isomers at the third and fourth positions of the azetidine ring).

This compound was subjected to column chromatography for isolation of said isomers to give isomer (a) and (b).

Isomer (a); mp 179° to 181.5° C.

Isomer (b); mp 196° to 198° C.

EXAMPLE 90

Hydrazine (one hydrate, 0.050 g.) was added to an ethanol (20 ml.) solution containing a mixture of cis and trans isomers of methyl 3-methyl-3-(5-methyl-1,3,4-thiadiazol-2-ylthiomethyl)-2-(2-oxo-3-phthalimido-1- azetidinyl)acrylate (0.350 g.), whereafter the mixture was stirred at ambient temperature for 19 hours. The reaction mixture was evaporated to dryness under reduced pressure to give a residue, which was dissolved in dilute hydrochloric acid. The aqueous solution was washed with ethyl acetate, adjusted to pH 8.5 with sodium bicarbonate and then extracted with ethyl acetate. The extract was washed with water and then dried over magnesium sulfate. The solution was evaporated to dryness under reduced pressure to give a residue, which was dissolved in dichloromethane (10 ml.). To the solution, there was dropwise added a dichloromethane (5 ml.) solution containing 2-phenoxyacetyl chloride (0.0612 g.) at −15° to −10° C., whereafter the mixture was stirred at the same temperature for 2 hours. The reation mixture was washed with dilute hydrochloric acid, water, 5% aqueous sodium bicarbonate and water, and then dried over magnesium sulfate. The solution was evaporated to dryness under reduced pressure to give an oily residue (0.120 g.), which was subjected to column chromatography on silica gel (4 g.). Elution was carried out with chloroform and the fractions containing a desired compound were collected. The first fractions containing a trans isomer of methyl 3-methyl-3-(5-methyl-1,3,4-thiadiazol-2-ylthiomethyl)-2-[2-oxo-3-(2-phenoxyacetamido)-1-azetidinyl]acrylate was evaporated to dryness under reduced pressure to give the same object compound (0.023 g.). A mixture of cis and trans isomers of the above object compound (0.020 g.) was obtained in the same manner and then a cis isomer of the above object compound (0.027 g.) was obtained in the same manner.

Trans isomer;

I R—$\nu$cm$^{-1}$ (CHCl$_3$): 3450, 1760, 1730, 1685.

N M R (TMS)—$\delta$ppm (CDCl$_3$): 2.27 (3H, s), 2.63 (3H, s), 3.76 (3H, s), 3.64, 3.68 (1H, d,d, J=2 Hz, 5 Hz), 3.96 (1H, t, J=5 Hz), 4.06, 4.44 (2H, AB-q, J=14 Hz), 4.56 (2H, s), 5.22 to 5.38 (1H, m), 6.86 to 7.40 (5H, m), 7.86 (1H, d, J=8 Hz).

Cis isomer;

I R—$\nu$cm$^{-1}$ (CHCl$_3$): 3450, 1765, 1725, 1690.

N M R (TMS)—$\delta$ppm (CDCl$_3$): 2.06 (3H, s), 2.62 (3H, s), 3.81 (3H, s), 3.69, 3.73 (1H, d,d, J=2 Hz, 5 Hz), 3.90 (1H, t, J=5 Hz), 4.32 (2H, s), 4.36 (2H, s), 5.00 to 5.08 (1H, m), 6.84 to 7.48 (5H, m).

EXAMPLE 91

2-[3-{4-(3-Amino-3-carboxypropoxy)phenylglyoxyloylamino}-2-oxo-1-azetidinyl]-2-(2-thienyl)acetic acid (400 mg.) and hydroxylamine hydrochloride (130 mg.) were suspended in water (7 ml.), and the suspension was adjusted to pH 7.0 with sodium bicarbonate to dissolve it. The mixture was stirred at 35° to 38° C. for 1.5 hours and the reaction mixture was treated with charcoal. The filtrate was adjusted to pH 3.2 to 3.0 with dilute hydrochloric acid, and then was concentrated to a volume of about 15 ml. under reduced pressure at 35° to 38° C. The concentrate was subjected to column chromatography on an adsorption resin Amberlite XAD-4 (Trade Mark, maker; Rohm & Haas Co., 80 ml.). Elution was carried out with water and next with methanol, and the fractions containing a desired compound were collected. The solvent was removed by distillation from the eluate under reduced pressure to give a residue, which was powdered with acetonitrile to give 2-[3-[2-{4-(3-amino-3-carboxypropoxy)phenyl}-2-hydroxyiminoacetamido]-2-oxo-1-azetidinyl]-2-(2-thienyl)acetic acid (240 mg.).

I R—$\nu$cm$^{-1}$ (Nujol): 3400 (broad), 1740, 1660 to 1640, 1610.

N M R (TMSP)—$\delta$ppm (D$_2$O): 2.38 to 2.48 (2H, m), 3.36 to 4.00 (3H, m), 4.08 to 4.28 (2H, m), 5.00 to 5.10 (1H, m), 5.60 and 5.68 (1H, s), 6.98 to 7.59 (7H, m).

The following compounds (Examples 92 to 102) were obtained by reacting the compound having phenylglyoxyloyl group with hydroxylamine hydrochloride in substantially the same manner as one described in Example 91.

EXAMPLE 92

Methyl 2-[3-(2-hydroxyimino-2-phenylacetamido)-2-oxo-1-azetidinyl]-3-(phenylthio)propionate.

I R—$\nu$cm$^{-1}$ (Nujol): 3480, 1760, 1730, 1670.

EXAMPLE 93

Methyl 2-[3-(2-hydroxyimino-2-phenylacetamido)-2-oxo-1-azetidinyl]-3-(phenylthio)acrylate.

I R—$\nu$cm$^{-1}$ (Nujol): 1750, 1710, 1660.

EXAMPLE 94

Methyl erythro-2-[3-(2-hydroxyimino-2-phenylacetamido)-2-oxo-1-azetidinyl]-3-methoxy-3-phenylpropionate.

I R—$\nu$cm$^{-1}$ (Nujol): 3300, 1725, 1665.

EXAMPLE 95

Methyl 2-[3-(2-hydroxyimino-2-phenylacetamido)-2-oxo-1-azetidinyl]-2-(2-thienyl)acetate.

I R—$\nu$cm$^{-1}$ (Nujol): 3300, 1755, 1730, 1665.

EXAMPLE 96

Methyl 2-[3-(2-hydroxyimino-2-phenylacetamido)-2-oxo-1-azetidinyl]-2-(1-naphthyl)acetate.

I R—$\nu$cm$^{-1}$ (film): 3250, 1740, 1660.

EXAMPLE 97

Methyl 2-[3-(2-hydroxyimino-2-phenylacetamido)-2-oxo-1-azetidinyl]-3-methyl-3-(5-methyl-1,3,4-thiadiazol-2-ylthiomethyl)acrylate (a mixture of trans and cis isomers).

This compound was subjected to column chromatography for isolation of said isomers to give each of trans and cis isomers.

| I R $\nu$cm$^{-1}$ (film) : Trans isomer; | Cis isomer; |
| --- | --- |
| 3300 | 3300 |
| 1760 | 1770 |
| 1730 | 1730 |
| 1670 | 1670 |

EXAMPLE 98

Methyl 3-(2-benzothiazolylthiomethyl)-2-[3-(2-hydroxyimino-2-phenylacetamido)-2-oxo-1-azetidinyl]-3-methylacrylate (mixture of trans and cis isomers).

I R—$\nu$cm$^{-1}$ (film): 3250, 1760, 1720, 1670.

EXAMPLE 99

2-[3-(2-Hydroxyimino-2-phenylacetamido)-2-oxo-1-azetidinyl]-2-(2-furyl)acetic acid.

I R—$\nu$cm$^{-1}$ (Nujol): 3300, 1755, 1735, 1710, 1660.

EXAMPLE 100

Methyl 2-[3-(2-hydroxyimino-2-phenylacetamido)-2-oxo-1-azetidinyl]-3-(4-hydroxyphenyl)propionate.

I R—νcm$^{-1}$ (Nujol): 3230, 1750, 1725, 1642.

EXAMPLE 101

Methyl D-2-[4-trans-styryl-3-(2-hydroxyimino-2-phenylacetamido)-2-oxo-1-azetidinyl]-2-phenylacetate (mixture of two cis isomers at the third and fourth positions of the azetidine ring).

I R—νcm$^{-1}$ (film): 3350, 1770 to 1740, 1670.

EXAMPLE 102

Methyl D-2-[3-(2-hydroxyimino-2-phenylacetamido)-4-hydroxymethyl-2-oxo-1-azetidinyl]-2-phenylacetate (a mixture of two cis isomers at the third and fourth positions of the azetidine ring).

This compound was subjected to column chromatography for isolation of said isomers to give each of two cis isomers.

One of two cis isomers;
mp 179° to 181.5° C.
The other cis isomer;
mp 196° to 198° C.

EXAMPLE 103

Triphenylphosphine (0.39 g.) was dissolved in anhydrous acetonitrile (10 ml.) and to the solution was added dropwise an anhydrous acetonitrile (5 ml.) solution containing bromine (0.24 g.) in 5 minutes at 5° C., whereafter the mixture was stirred at the same temperature for 25 minutes. An anhydrous acetonitrile (5 ml.) solution containing 2-azido-3-(α-methoxycarbonylbenzylamino)propionic acid hydrochloride (0.32 g.) and triethylamine (0.4 g.) was added dropwise to said mixture at 5° C. in 15 minutes. The mixture was stirred at the same temperature for half an hour and then at room temperature for 4 hrs. The acetonitrile was distilled off from the reaction mixture under reduced pressure and ether was added to the residue. The insoluble material was filtered off, and the solvent was distilled off from the filtrate under reduced pressure. The residue was subjected to column chromatography on silica gel (20 g.). The elution was conducted with chloroform and the fractions containing the object compound were collected. The solvent was distilled off from the solution under reduced pressure to give a mixture of two isomers (a) and (b) of methyl 2-(3-azido-2-oxo- 1-azetidinyl)-2-phenylacetate (90 mg.).

I R—νcm$^{-1}$ (film): 2080, 1760, 1730.

| NMR (TMS) δppm (CDCl$_3$): Isomer (a); | Isomer (b); |
|---|---|
| 2.93 (1H, q, J=2Hz, J=6Hz) | 3.26–3.76 (2H, m) |
| 3.73 (3H, s) | 3.80 (3H, s) |
| 3.86 (1H, t, J=6Hz) | 4.50 (1H, q, J=2Hz, J=5Hz) |
| 4.63 (1H, q, J=2Hz, J=6Hz) | 5.60 (1H, s) |
| 5.56 (1H, s) | 7.33 (5H, s) |
| 7.28 (5H, s) | |

The same object compound of Example 103 was obtained by using the following condensing agent or base, (a)–(d), in substantially the same manner as one described in Example 103.

(a) N,N'-dicyclohexylcarbodiimide,
(b) N,N'-diisopropylcarbodiimide,
(c) N,N-dimethylaniline, [2-azido-3-(α-methoxycarbonylbenzylamino)propionyl chloride hydrochloride was used as a starting compound],
(d) ethylmagnesium bromide, [methyl 2-azido-3-(α-methoxycarbonylbenzylamino)propionate was used as a starting compound].

The following compounds (Examples 104 to 106) were obtained by subjecting the corresponding 2,3-disubstituted propionic acid with N,N'-dicyclohexylcarbodiimide as a condensing agent in substantially the same manner as described in Example 103.

EXAMPLE 104

D-2-(3-Azido-2-oxo-1-azetidinyl)-2-phenylacetic acid (a mixture of two isomers at the third position of the azetidine ring).

I R—νcm$^{-1}$ (film): 2100, 1750 (broad).

N M R (TMS)—δppm (CDCl$_3$): 3.2 to 3.8 (2H, m), 4.48 (1H, m), 5.54 (1H, broad s), 7.35 (5H, s).

EXAMPLE 105

D-2-(3-Bromo-2-oxo-1-azetidinyl)-2-phenylacetic acid (a mixture of two isomers (a) and (b) at the third position of the azetidine ring).

This compound was subjected to column chromatography for isolation of said isomers to give each of isomers (a) and (b).

| NMR (TMS) δppm (CDCl$_3$): Isomer (a); | Isomer (b); |
|---|---|
| 3.20 (1H, d,d, J=2HZ, 6Hz) | 3.54 to 3.88 (2H, m) |
| 4.17 (1H, d,d, J=5Hz, J=6Hz) | 4.62 to 4.76 (1H, m) |
| 4.83 (1H, d,d, J=2Hz, J=6Hz) | 5.6 (1H, s) |
| 5.68 (1H, s) | 7.17 to 7.45 (5H, m) |
| 7.28 to 7.50 (5H, m) | |

EXAMPLE 106

2-(4-Hydroxyphenyl)-2-(2-oxo-3-tritylamino-1-azetidinyl)acetic acid, mp 135° to 139° C. (dec).

I R—νcm$^{-1}$ (Nujol): 3320, 1740, 1720.

N M R (TMS)—δppm [(CD$_3$)$_2$ SO]: 2.68 (1H, m), 3.60 (1H, t, J=6Hz), 3.92 (1H, m), 5.24 (1H, s), 6.60 to 7.72 (19H, m).

EXAMPLE 107

2-[3-{4-(3-tert-butoxycarbonylamino-3-methoxycarbonylpropoxy)phenylglyoxyloylamino}-2-oxo-1-azetidinyl]-2-(2-thienyl)acetic acid (0.480 g.) was dissolved in methanol (3 ml.), and to the solution, there was added 1 N aqueous sodium hydroxide (2 ml.) under ice-cooling. The mixture was stirred at the same temperature for 7 hours while adjusting to pH 9.0 to 9.5 with 1 N aqueous sodium hydroxide. After the reaction, the reaction mixture was adjusted to pH 7.0 with dilute hydrochloric acid and evaporated to dryness under reduced pressure on a water bath. The resultant residue was dissolved in a small amount of water, and the aqueous solution was adjusted to pH 5.5 with dilute hyrochloric acid and then washed with ethyl acetate. The aqueous solution was adjusted to pH 4.0 to 4.5 with dilute hydrochloric acid and then extracted with ethyl acetate. This extract was evaporated to dryness under reduced pressure to give 2-[3-{4-(3-tert-butoxycarbonylamino-3-carboxypropoxy) phenylglyoxyloylamino}-2-oxo-1-azetidinyl]-2-(2-thienyl) acetic acid (0.350 g.).

I R—νcm$^{-1}$ (film): 3400 to 3300, 1750, 1730, 1710, 1680 to 1660.

EXAMPLE 108

2-[3-{4-(3-tert-Butoxycarbonylamino-3-carboxypropoxy)phenylglyoxyloylamino}-2-oxo-1-azetidinyl]-2-(2-thienyl)acetic acid (0.830 g.) was added to a mixture of benzene (4 ml.) and anisol (1 ml.), and to the mixture, there was added 2,2,2-trifluoroacetic acid (2 ml.) under ice-cooling. The mixture was stirred at the same temperature for 2.5 hours, and diethyl ether (50 ml.) was added to the reaction mixture, whereafter the stirring was continued under ice-cooling for half an hour. Insoluble materials were collected by filtration and suspended in ethyl acetate (30 ml.). The suspension was stirred for an hour, whereafter the insoluble materials were collected by filtration, washed with diethyl ether and then dried to give 2-[3-{4-(3-amino-3-carboxypropoxy)phenylglyoxyloylamino}-2-oxo-1-azetidinyl]-2-(2-thienyl)acetic acid (0.49 g.).

I R—νcm$^{-1}$ (Nujol): 3450 to 3300, 1740, 1680, 1660, 1600.

N M R (TMSP)—δppm (D$_2$O+NaHCO$_3$): 2.28 to 2.54 (2H, m), 3.32 to 4.10 (3H, m), 4.20 to 4.38 (2H, m), 5.00 to 5.12 (2H, m), 5.61 and 5.67 (1H, each s), 7.00 to 8.08 (7H, m).

EXAMPLE 109

2-[3-(N-Benzyloxycarbonyl-2-phenylglycinamido)-2-oxo-1-azetidinyl]-2-(2-thienyl)acetic acid (0.19 g.) was dissolved in methanol (10 ml.), and to the solution, there was added 10% palladium on carbon (0.15 g.) as a catalyst. The mixture was subjected to catalytic reduction in a stream of hydrogen gas at ordinary temperature and ordinary pressure. A calculated volume of hydrogen gas was absorbed into the mixture in the course of 6.5 hours. The catalyst was filtered off from the reaction mixture and the filtrate was evaporated to dryness under reduced pressure to give an oily residue, which was pulverized with ethyl acetate. The powder (0.09 g.) obtained was treated with a mixture of acetonitrile and water (volume ratio, 20:1) to give 2-[3-(2-phenylglycinamido)-2-oxo-1-azetidinyl]-2-(2-thienyl)acetic acid (0.02 g.).

mp 199° to 215° C. (dec.).

I R—νcm$^{-1}$ (Nujol); 3300, 1730, 1690.

N M R (TMS)—δppm (CD$_3$OD): 3.10 (1H, d,d, J=2.5Hz, 5Hz), 3.86 (1H, t, J=5Hz), 4.90 (1H, d,d, J=2.5Hz, 5Hz,), 5.56 (1H, s), 4.92 (1H, s), 6.94 to 7.60 (8H, m).

EXAMPLE 110

Methyl erythro-2-[3-(2-hydroxyimino-2-phenylacetamido)-2-oxo-1-azetidinyl]-3-methoxy-3-phenylpropionate (810 mg.) was dissolved in acetone (4 ml.), and to the solution, there was dropwise added 0.1 N aqueous sodium hydroxide (3.8 ml.) under ice-cooling with stirring. The stirring was continued at the same temperature for 5 minutes. The acetone was removed by distillation from the reaction mixture under reduced pressure, and water (5 ml.) was added to the remaining aqueous solution. The aqueous solution was washed with ethyl acetate and adjusted to pH 2 with 3 N hydrochloric acid. The solution was extracted with two 10 ml. portions of ethyl acetate, and the extract was washed with a saturated aqueous sodium chloride and then dried over magnesium sulfate. The solvent was removed by distillation from the solution under reduced pressure to give 2-[3-(2-hydroxyimino-2-phenylacetamido) -2-oxo-1-azetidinyl]-3-methoxy-3-phenylpropionic acid (65 mg.).

mp 81° to 85° C. (dec.).

IR—νcm$^{-1}$ (film): 3300 (broad), 1750 (shoulder) 1720 (broad), 1650.

N M R (TMS)—δppm[(CD$_3$)$_2$CO]: 3.27 (3H, s), 3.70 (1H, m), 4.10 (1H, t, J=6Hz), 4.56 (1H, d, J=5Hz), 4.93 (1H, d, J=5Hz), 5.20 (1H, m), 7.2 to 7.8 (m), 8.18 (1H, m).

The following compounds (Examples 111 to 126) were obtained by subjecting the corresponding compound having methyl ester bond to hydrolysis in substantially the same manner as one described in Example 110.

EXAMPLE 111

2-[3-(2-Hydroxyimino-2-phenylacetamido)-2-oxo-1-azetidinyl]-3-phenylthiopropionic acid.

IR—νcm$^{-1}$ (film): 3250 (broad), 2900 to 2700, 1730 (broad), 1670 (broad).

N M R (TMS)—δppm [(CD$_3$)$_2$CO]: 3.24 to 3.92 (4H, m), 4.53 (1H, m), 5.14 (1H, m), 7.15 to 7.80 (10H, m), 8.39 (1H, m).

EXAMPLE 112

2-[3-(2-Hydroxyimino-2-phenylacetamido)-2-oxo-1-azetidinyl]-2-(2-thienylacetic) acid.

IR—νcm$^{-1}$(Nujol): 3350, 1755, 1700, 1650.

N M R (TMS)—δppm(CD$_3$OD): 3.43 (1H, d,d, J=2.5Hz, 6Hz), 3.95 (1H, t, J=6Hz), 5.08 (1H, m), 5.84 (1H, s) 6.90 to 7.73 (8H, m).

EXAMPLE 113

2-[3-[4-{3-tert-Butoxycarbonylamino-3-(4-methoxybenzyloxycarbonyl)propoxy}phenylglyoxyloylamino]-2-oxo-1-azetidinyl]-2-(2-thienyl)acetic acid.

IR—νcm$^{-1}$ (film): 3450 to 3300, 1760, 1730, 1710, 1680 to 1660.

EXAMPLE 114

2-[3-(2-Hydroxyimino-2-phenylacetamido)-2-oxo-1-azetidinyl]-2-(1-naphthyl)acetic acid.

IR—νcm$^{-1}$ (film): 3250 (broad), 2900 to 2700, 1730(broad), 1670(broad).

EXAMPLE 115

2-[3-(2-Hydroxyimino-2-phenylacetamido)-2-oxo-1-azetidinyl]-3-phenylthioacrylic acid, mp 78° to 83° C. (dec.).

IR—νcm$^{-1}$ (Nujol): 1740, 1710, 1680 (broad).

N M R (TMS)—δppm[(CD$_3$)$_2$CO]: 3.90 to 4.2 (2H, m), 5.40 (1H, m), 7.2 to 7.8 (11H, m), 8.53 (1H, d, J=8Hz).

EXAMPLE 116

3-Methyl-3-(5-methyl-1,3,4-thiadiazol-2-ylthiomethyl)-2-[2-oxo-3-(2-phenoxyacetamido)-1-azetidinyl]acrylic acid.

IR—νcm$^{-1}$ (Nujol): 3250, 1740, 1720, 1650.

N M R (TMS)—δppm(CD$_3$OD): 2.28 (3H, s), 2.68 (3H, s), 3.72, 3.76 (1H,d,d, J=2Hz, 5Hz), 3.90 (1H,t, J=5Hz), 4.16, 4.46 (2H, AB-q, J=14hz), 4.56 (2H, s), 5.08, 5.12 (1H,d,d, J=2Hz, 5Hz), 6.96 to 6.39 (5H, m).

EXAMPLE 117

2-[3-(2-Hydroxyimino-2-phenylacetamido)-2-oxo-1-azetidinyl]-3-methyl-3-(5-methyl-1,3,4-thiadiazol-2-ylthiomethyl)acrylic acid.

IR—$\nu cm^{-1}$ (Nujol): 3300, 1740, 1720, 1660.

EXAMPLE 118

3-(2-Benzothiazolylthiomethyl)-2-[3-(2-hydroxyimino-2-phenylacetamido)-2-oxo-1-azetidinyl]-3-methylacrylic acid.

IR—$\nu cm^{-1}$ (Nujol): 3250, 1740, 1720, 1660.

EXAMPLE 119

3,3-Bis(5-methyl-1,3,4-thiadiazol-2-ylthiomethyl)-2-[2-oxo-3-{2-(2-thienyl)acetamido}-1-azetidinyl]acrylic acid dicyclohexylamine salt.

IR—$\nu cm^{-1}$ (Nujol): 3300, 1760, 1675, 1640–1620.

N M R (TMS)—$\delta$ppm(CD$_3$OD): 1.28 to 2.18 (10H, m), 2.68 (6H, s), 3.08 to 3.28 (2H, m), 3.52, 3.56 (1H, d,d, J=2Hz, 5hz), 3.75 (1H, t, J=5Hz), 3.76 (2H, s), 4.34 (2H, s) 4.56 (2H, s), 4.98, 5.02 (1H, d,d, J=4Hz), 6.92 to 7.26 (3H, m).

EXAMPLE 120

2-[3-(2-Hydroxyimino-2-phenylacetamido)-2-oxo-1-azetidinyl]-3-(4-hydroxyphenyl)propionic acid.

IR—$\nu cm^{-1}$ (film): 3400, 1735, 1720, 1660.

EXAMPLE 121

2-(4-Benzyloxyphenyl)-2-[4-methylthio-2-oxo-3-(2-phenylacetamido)-1-azetidinyl]acetic acid (a mixture of two trans isomers at the third and fourth positions of the azetidine ring).

IR—$\nu cm^{-1}$(film): 3300, 1760, 1740, 1670.

NMR (TMS)—$\delta$ppm[(CD$_3$)$_2$CO]: 1.22 and 1.89(3H, each s), 3.57(2H, s), 4.51 to 5.03 (2H,m), 5.15(2H,s), 5.30 (1H,s) 6.95 to 7.69(14H,m), 8.10(1H,d, J=8Hz).

EXAMPLE 122

2-[4-(5-Methyl-1,3,4-thiadiazol-2-ylthio)-2-oxo-3-{2-(2-thienyl)acetamido}-1-azetidinyl]-2-phenylacetic acid (a mixture of two cis isomers at the third and fourth positions of the azetidine ring).

IR—$\nu cm^{-1}$ (Nujol): 1775, 1740, 1660.

NMR (TMS)—67 ppm(CD$_3$OD): 2.60(3H,s), 3.72 (2H,s), 5.48(1H,s), 5.66(1H,d, J=4Hz), 6.14(1H,d, J=4Hz), 6.68 to 7.60(8H,m).

EXAMPLE 123

2-[4-(5-Methyl-1,3,4-thiadiazol-2-ylthio)-2-oxo-3-{2-(2-thienyl)acetamido}-1-azetidinyl]-2-phenylacetic acid (a mixture of two trans isomers at the third and fourth positions of the azetidine ring). p IR—$\nu cm^{-1}$ (Nujol): 1775, 1750, 1640.

NMR (TMS)—$\delta$ppm(CD$_3$OD): 2.60 (3H,s), 3.72 (2H,s), 5.10(1H,d,J=2Hz), 5.42 (1H,s),5.66 (1H,d,J=2Hz), 6.60 to 7.36 (8H,m).

EXAMPLE 124

2-[4-Methylthio-2-oxo-3-{2-(2-thienyl)acetamido}-1-azetidinyl]-2-phenylacetic acid (a mixture of two trans isomers at the third and fourth positions of the azetidine ring).

IR—$\nu cm^{-1}$(film): 3300, 1770, 1750, 1670.

NMR (TMS)—$\delta$ppm(CDCl$_3$): 1.82 and 2.05 (3H, each s), 3.60 (2H, s), 3.78 (3H, s), 4.40 to 4.98 (2H, m), 5.12 (2H, s), 5.30 and 5.35 (1H, each s), 6.50 (1H, d, J=8Hz), 6.85 to 7.62 (14H, m).

EXAMPLE 125

2-[4-trans-Styryl-3-(2-hydroxyimino-2-phenylacetamido)-2-oxo-1-azetidinyl]-2-phenylacetic acid.

IR—$\nu cm^{-1}$(Nujol): 3250, 2600 to 2500, 1760, 1740, 1690.

EXAMPLE 126

2-[3-(2-Hydroxyimino-2-phenylacetamido)-4-hydroxymethyl-2-oxo-1-azetidinyl]-2-phenylacetic acid.

IR—$\nu cm^{-1}$ (Nujol): 3380, 3200, 1750, 1720, 1700(shouler), 1650.

EXAMPLE 127

Methyl 2-(2-oxo-3-phthalimido-1-azetidinyl)-2-(2-thienyl) acetate (3.0 g.) and lithium iodide (3.4 g.) were added to an dried pyridine (40 ml.), whereafter the mixture was refluxed under heating for 2 hours. After the reaction, the reaction mixture was poured into a mixture of ice-water (250 ml.) and ethyl acetate (300 ml.).

The resulting mixture was adjusted to pH 2 with 10% hydrochloric acid under ice-cooling, and the precipitating crystals were collected by filtration to give 2-(2-oxo-3-phthalimido-1-azetidinyl)-2-(2-thienyl)acetic acid (0.21 g.). The ethyl acetate layer was separated out and the remaining aqueous solution was further extracted with ethyl acetate (200 ml.). This extract and the above ethyl acetate layer were combined, washed with diluted hydrochloric acid and water, and then dried over magnesium sulfate. The solvent was removed by distillation from the solution under reduced pressure to give the same object compound (2.26 g.). The same compound (0.17 g.) was further recovered from the mother liquor. Total yield was 2.64 g.

mp 199° to 201° C.

IR—$\nu cm^{-1}$ (Nujol): 2750 to 2500, 1770, 1740, 1720.

N M R (TMSP)—$\delta$ppm(D$_2$O+NaHCO$_3$): 3.36 (1H,q, J=3Hz, 5Hz), 3.91 (1H,t, J=5hz), 5.38 (1H,q, J=3Hz, 5Hz), 5.74 (1H, s), 7.00 to 7.80 (7H, m).

The following compounds (Examples 128 and 129) were obtained by reacting the corresponding compound having methyl ester bond with anhydrous lithium iodide in pyridine in substantially the same manner as one described in Example 127.

EXAMPLE 128

2-(3-Azido-2-oxo-1-azetidinyl)-2-phenylaetic acid (a mixture of two isomers (a) and (b) at the third position of the azetidine ring).

IR—$\nu cm^{-1}$ (film): 2570, 2100, 1740, 1720.

| NMR (TMS) $\delta$ppm (CD$_3$OD): | |
|---|---|
| Isomer (a); | Isomer (b); |
| 2.95(1H,q, J=2Hz, 5Hz) | 3.39(1H,t, J=5Hz) |
| 3.90(1H,t, J=5Hz) | 3.56(1H,q, J=2Hz, 5Hz) |
| 4.77(1H,q, J=2Hz, 5Hz) | 4.59(1H,q, J=2Hz, 5Hz) |
| 5.56(1H, s) | 5.54(1H, s) |
| 7.36(5H, s) | 7.36(5H, s) |

EXAMPLE 129

D-2-(2-Oxo-3-phenoxy-1-azetidinyl)-2-phenylacetic acid [a mixture of two isomers (a) and (b) at the third position of the azetidine ring].

IR—$\nu$cm$^{-1}$(film): 1740 (broad).

NMR (TMS)
$\delta$ppm[(CD$_3$)$_2$CO]:

| Isomer(a); | Isomer(b); |
|---|---|
| 3.18(1H,d,d, J=2Hz,6Hz) | 3.56 (1H, m) |
| 4.02(1H,t, J=6Hz) | 3.77(1H,m) |
| 5.27(1H,m) | 5.13(1H,m) |
| 5.72(1H,s) | 5.69(1H,s) |
| 6.8 to 7.5(10H,m) | 6.8 to 7.5(10H,m) |

EXAMPLE 130

D-2-(3-Benzyloxy-2-oxo-1-azetidinyl)-2-phenylacetic acid [a mixture of two isomers (a) and (b) at the third position of the azetidine ring] (105 mg.) was obtained by reacting benzyl D-2-(3-benzyloxy-2-oxo-1-azetidinyl)-2-phenylacetate (280 mg.) with anhydrous lithium iodide (280 mg.) in pyridine (3m l.) in substantially the same manner as one described in Example 127.

IR—$\nu$cm$^{-1}$ (film): 1730 (broad).

NMR (TMS)
$\delta$ppm [(CD$_3$)$_2$CO]:

| Isomer (a); | Isomer (b); |
|---|---|
| 3.14(1H,d,d, J=3Hz, 6Hz) | 3.5 to 3.8 (1H,m) |
| 4.00(1H,t, J=6Hz) | 5.30(1H,d,d, J=3Hz,6Hz) |
| 5.41(1H,d,d, J=3Hz, 6Hz) | 5.63(1H,s) |
| 5.65(1H,s) | 6.8 to 7.5 (10H,m) |
| 6.8 to 7.5 (10H,m) | |

EXAMPLE 131

0.1 N Aqueous sodium hydroxide (20 ml.) was added to an acetone (15 ml.) solution containing methyl 2-(3-amino-2-oxo-1-azetidinyl)-3-methyl-3-(5-methyl-1,3,4-thiadiazol-2-ylthiomethyl)-acrylate (656 mg.) under ice-cooling with stirring. The mixture was stirred at 10° to 15° C. for 5 hours, and then sodium bicarbonate (200 mg.) was added to the mixture. To the mixture, there was added dropwise an acetone (5 ml.) solution containing N-(2,2,2-trichloroethoxycarbonyl)-2-phenylglycyl chloride (830 mg.) at 0° to 5° C. with stirring, whereafter the mixture was stirred at the same temperature for 2 hours. The acetone was removed from the reaction mixture under reduced pressure to give an aqueous solution, which was extracted with ethyl acetate. The extract was washed with dilute hydrochloric acid, water and 5% aqueous sodium bicarbonate in turn, and then dried over magnesium sulfate. The solution was evaporated to dryness under reduced pressure to give an oily residue, which was subjected to column chromatography on silica gel (12 g.). Elution was carried out with chloroform and the fractions containing a desired compound were collected. The solvent was removed by distillation from the eluate under reduced pressure to give 2-[3-{N-(2,2,2-trichloroethoxycarbonyl)-2-phenylglycinamido}-2-oxo-1-azetidinyl]-3-methyl-3-(5-methyl-1,3,4-thiadiazol-2-ylthiomethyl)acrylic acid (130 mg.).

IR—$\nu$cm$^{-1}$(film): 3250, 1760, 1720, 1700, 1670.

N M R (TMS)—$\delta$ppm(CDCl$_3$): 2.24(3H,s), 2.66(3H,s), 3.56, 3.60(1H,d,d, J=2Hz, 5Hz), 3.84(1H,t), 3.98, 4.52(2H, AB-q, J=14Hz), 4.71(2H,s), 4.88, 4.92(1H,d,d, J=2Hz, 5Hz), 7.28 to 7.48(5H,m).

EXAMPLE 132

Methyl 3-(4-benzyloxyphenyl)-2-(2-oxo-3-phthalimido-1-azetidinylpropionate) (1.5 g.) was dissolved in a mixture of ethanol (20 ml.) and ethyl acetate (10 ml.), whereafter 10% palladium on carbon (1.5 g.) was added to the solution. The reaction mixture was subjected to catalytic reduction in a stream of hydrogen gas at ordinary temperature by using medium pressure apparatus in the course of 3 days and a calculated volume of the hydrogen gas was absorbed into the reaction mixture. After the reaction, the catalyst was removed by filtration from the reaction mixture and the filtrate was evaporated to dryness under reduced pressure. The resulting residue (1.01 g.) was crystallized from a mixture of diethyl ether and ethyl acetate to give methyl 3-(4-hydroxyphenyl)-2-(2-oxo-3-phthalimido-1-azetidinylpropionate) (0.33 g.). The same product (0.05 g.) was recovered from the mother liquor. Total yield was 0.38 g.

IR—$\nu$cm$^{-1}$ (Nujol): 3250, 1780, 1762, 1735, 1690.

EXAMPLE 133

Methyl 2-(3-azido-4-methylthio-2-oxo-1-azetidinyl)-2-phenylacetate (two trans isomers) (0.60 g.) was dissolved in methylene chloride (10 ml.), and to the solution was added dropwise a methylene chloride (5 ml.) solution containing chlorine (77 mg.) at −65° to −70° C. in 10 minutes. The mixture was stirred at the same temperature for an hour, washed with a sodium thiosulfate aqueous solution and water, and then dried over anhydrous magnesium sulfate. The solvent was distilled off from the solution under reduced pressure, and the residue (0.64 g.) was subjected to column chromatography on silica gel (15 g.). The elution was conducted with chloroform and the fractions containing the object compound were collected. The solvent was distilled off from the solution under reduced pressure to give an oily mixture of four isomers (two trans and two cis monomers) of methyl 2-(3-azido-4-chloro-2-oxo-1-azetidinyl)-2-phenylacetate (0.44 g.).

IR

Mixture of two cis isomers—$\nu$cm$^{-1}$ (liquid film): 2120, 1785, 1745.

Mixture of two trans isomers—$\nu$cm$^{-1}$ (liquid film): 2120, 1790, 1750.

N.M.R. (TMS) of two cis isomers
$\delta$ppm (CDCl$_3$):

| one of cis isomers | another cis isomer |
|---|---|
| 3.76 (3H, s) | 3.76 (3H, s) |
| 4.74 (1H, d, J=5 Hz) | 4.86 (1H, d, J=5 Hz) |
| 5.34 (1H, s) | 5.48 (1H, s) |
| 5.68 (1H, d, J=5 Hz) | 6.07 (1H, d, J=5 Hz) |
| 7.40 (5H, s) | 7.40 (5H, s) |

EXAMPLE 134

Methyl 2-(3-azido-4-chloro-2-oxo-1-azetidinyl)-2-phenylacetate (a mixture of two trans and two cis isomers at the third and fourth positions of the azetidine ring (240 mg.) was obtained by reacting methyl 2-(3-azido-4-5-methyl-1, 3, 4-thiadiazol-2-ylthio)-2-oxo-1-azetidnyl-2-phenylacetate (two trans isomers) (0.37 g.) with chlorine (0.1 g.) in substantially the same manner as described in Example 133.

IR

Mixture of two trans isomers—$\nu$cm$^{-1}$ (film): 2120, 1790, 1750.

Mixture of two cis isomers—$\nu$cm$^{-1}$ (film): 2120, 1785, 1745.

EXAMPLE 135

Methyl 2-(3-azido-4-chloro-2-oxo-1-azetidinyl)-2-phenylacetate (two trans and two cis isomers) (4.0 g.) was dissolved in dried methylene chloride (50 ml.), and to the solution were added anhydrous potassium carbonate (1.13 g.) and 5-methyl-1,3,4-thiadiazole-2-thiol (2.10 g.). The mixture was stirred at room temperature for 8 hrs, poured into icewater and then extracted with ether. The extract was washed with 1% aqueous potassium carbonate and water, and dried over anhydrous magnesium sulfate. The solvent was distilled off from the solution under reduced pressure, and the residue (4.05 g.) was subjected to column chromatography on silica gel (160 g.). The elution was conducted with chloroform and the fractions containing the object compound were collected. The solvent was distilled off from the solution under reduced pressure to give methyl 2-[3-azido-4-(5-methyl-1,3,4-thiadiazol-2-ylthio)-2-oxo-1-azetidinyl]-2-phenylacetate (two trans and two cis isomers) (2.81 g.).

Two transisomers:

m.p.: 81° to 84° C.

IR—$\nu$cm$^{-1}$ (Nujol): 2130, 1790, 1780 (shoulder), 1745.

Two cis isomers:

IR—$\nu$cm$^{-1}$ (film): 2120, 1780, 1745.

EXAMPLE 136

Methyl 3,3-dimethyl-2-(2-oxo-3-phthalimido-1-azetidinyl)acrylate (0.334 g.), N-bromosuccinimide 0.360 g.) and benzoyl peroxide (0.020 g.) were suspended in carbon tetrachloride (30 ml), whereafter the mixture was refluxed under heating for an hour. After the reaction, the precipitating materials were filtered off from the reaction mixture and the filtrate was evaporated to dryness under reduced pressure to give an oily residue. The residue was pulverized with carbon tetrachloride to give crystalline methyl 3,3-bis(bromomethyl)-2-(2-oxo-3-phthalimido-1-azetidinyl)acrylate (0.300 g.), mp 127.5° to 131° C.

IR—$\nu$cm$^{-1}$ (Nujol): 1790, 1770, 1730, 1720.

N.M.R. (TMS)—$\delta$ppm[(CD$_3$)$_2$CO]: 3.75 (3H, s), 4.37 (2H, d, J=5Hz) 4.55, 4.75 (2H, AB-q, J=10Hz), 4.60, 4.87 (2H, AB-q, J=10Hz), 5.65 (1H, t, J=5Hz), 7.93 (4H, S).

EXAMPLE 137

A mixture of cis and trans isomers of methyl 3-bromomethyl-3-methyl-2-(2-oxo-3-phthalimido-1-azetidinyl)-acrylate (331.5 mg.) was obtained by reacting methyl 3,3-dimethyl-2-(2-oxo-3-phthalimido-1-azetidinyl)acrylate (0.344 g.) with N-bromosuccinimide (0.178 g.) in substantially the same manner as one discribed in Example 136.

IR—$\nu$cm$^{-1}$ (film): 1780, 1765, 1710.

N.M.R. (TMS)—$\delta$ppm (CDCl$_3$): 2.31 and 2.37 (3H, s,), 3.84 and 3.88 (3H,s), 3.88 to 4.12 (2H,m), 4.12,4.76 and 4.38,4.70 (2H, each AB-q, J=10Hz), 5.52 to 5.64 (1H,m), 7.72 to 7.96 (4H,m).

EXAMPLE 138

A mixture of cis and trans isomers of methyl 3-bromomethyl-3-methyl-2-(2-oxo-3-phthalimido-1-azetidinyl)-acrylate (107 mg.) was dissolved in N,N-dimethylformamide (2 ml.) and to the solution, there was added 5-methyl-1,3,4-thiadiazole-2-thiol (41 mg.). Triethylamine (31 mg.) was added dropwise to the above solution under ice-cooling with stirring, whereafter the mixture was stirred at the same temperature for an hour. The reaction mixture was poured into ice-dilute hydrochloric acid and then extracted with ethyl acetate. The extract was washed with dilute hydrochloric acid, water, 5% aqueous sodium bicarbonate and water in turn, and then dried over magnisium sulfate. The solution was evaporated to dryness under reduced pressure to give a residue, which was subjected to column chromatography on silica gel (4 g). Elution was carried out with chloroform and the fractions containing a desired compound were collected. The eluates containing a trans isomer of methyl 3-methyl-3-(5-methyl-1,3,4,-thiadiazol-2-ylthimethyl)-2-(2-oxo-3-phthalimido-1-azetidinyl)-acrylate were evaporated to dryness under reduced pressure to give the same compound (18 mg.) The fractions containing a mixture of cis and trans isomers of the above compound were treated in the same manner to give the mixture of cis and trans isomers of the compound (30 mg.). And further, a cis isomer of the above compound (28 mg.) was given in the same manner. Physical constant:

Trans isomer;

IR—$\nu$cm$^{-1}$(film): 1790, 1770, 1730, 1720.

NMR(TMS)—$\delta$ppm(CDCl$_3$): 2.38 (3H,s), 2.73(3H,s), 3.85(3H,s), 4.10(2H, d, J=5Hz),4,28, 4.78(2H, AB-q, J=10Hz), 5.64(1H,t, J=5Hz), 8.00 to 7.76(4H,m).

Cis isomer;

$\nu$cm$^{-1}$(Nujol): 1780, 1760, 1730, 1720.

NMR (TMS)—$\delta$ppm(CDCl$_3$): 2.33(3H,s), 2.74(3H,s), 3.86(3H,s), 3.92 to 4.08(2H,m), 4.85, 4.72(2H, AB-q, J=10Hz), 5.56, 5.60(1H, d,d, J=5Hz), 7.76 to 7.98 (4H,m).

EXAMPLE 139

Methyl 3,3-bis(5-methyl-1,3,4-thiadiazol-2-ylthiomethyl)-2-(2-oxo-3-phthalimido-1-azetidinyl)acrylate (590 mg.) was obtained by reacting methyl 3,3-bis(bromomethyl)-2-(2-oxo-3-phthalimido-1-azetidinyl)acrylate (500 mg.) with 5-methyl-1,3,4-thiadiazole-2-thiol (310 mg.) in substantially the same manner as described in Example 138.

IR—$\nu$cm$^{-1}$(film): 1790, 1770, 1730 1720.

NMR(TMS)—$\delta$ppm(CDCl$_3$): 2.75(3H,s), 2.77(3H,s), 3.90(3H,s), 4.13 (2H,d, J=4Hz), 4.47, 4.80(2H, AB-q, J=14Hz), 4.77(2H,s), 5.62(1H,t, J=4Hz), 7.40 to 7.90 (4H,m).

EXAMPLE 140

A mixture of methyl 3-(2-benzothiazolylthiomethyl)-3-methyl-2-(2-oxo-3-phthalimido-1-azetidinyl)acrylate and methyl 3,3-bis(2-benzothiazolylthiomethyl)-2-(2-oxo-3-phthalimido-1-azetidinyl)acrylate (2.53 g.) was obtained by reacting a mixture of methyl 3-bromomethyl-3-methyl-2-(2-oxo-3-phthalimido-1-azetidinyl)acrylate and methyl 3,3-bis(bromomethyl)-2-(2-oxo-3-phthalimido-1-azetidinyl)acrylate (2.54 g.) with benzothiazole-2-thiol (0.870 g.) in substantially the same manner as one described in Example 138.

IR—$\nu$cm$^{-1}$(film): 1780, 1760, 1720.

EXAMPLE 141

2-(3-Amino-2-oxo-1-azetidinyl)-2-(4-hydroxyphenyl)acetic acid (0.236 g.) was suspended in dried chloroform (10 ml.) and to the suspension, there was added bis(trimethylsilyl)acetamide (0.406 g.), whereafter the mixture was stirred at ambient temperature overnight. 1-(1,1-Dimethoxymethyl)perhydroazepine (0.200 g.) was added to the resulting mixture and the mixture obtained was stirred at ambient temperature for 2 hours. Water (3 ml.) was added to the reaction mixture and the mixture was stirred for a while. The mixture was evaporated to dryness under reduced pressure to give a residue, which was suspended in a small amount of acetone. The suspension was stirred at ambient temperature for 20 minutes and the powdery materials were collected by decantation and then this operation was repeated three times. The powders obtained were washed with acetone to give 2-(4-hydroxyphenyl)-2-[2-oxo-3-(perhydro-1-azepinylmethyleneamino-1-azetidinyl]acetic acid (0.330 g.)

IR—$\nu cm^{-1}$ (Nujol): 3500 to 3400, 1740, 1690, 1600.

EXAMPLE 142

Methyl 2-(2-oxo-3-phthalimido-1-azetidinyl)-3-phenylthiopropionate (5.1 g.) and pyridine (4.0 g.) were dissolved in dichloromethane (100 ml.), and to the solution, there was added dichloromethane (20 ml.) solution containing sulfuryl chloride (2.0 g.) at 35° to 40° C. in the course of 70 minutes with stirring. The stirring was continued at the same temperature for an hour. After the reaction, the reaction mixture was evaporated to dryness under reduced pressure. Ethyl acetate (100 ml.) and water (50 ml.) were added to the residue obtained, and the resultant mixture was stirred for a while. The ethyl acetate layer was separated from the mixture and the remaining aqueous solution was extracted with ethyl acetate. This extract and the above ethyl acetate layer were combined, washed with three portions of diluted hydrochloric acid, three portions of saturated aqueous sodium bicarbonate, two portions of water and then dried over magnesium sulfate. The solvent was removed by distillation from the solution under reduced pressure to give an oily residue (4.95 g.), which was subjected to column chromatography on silica gel(30 g.). Elution was carried out with chloroform and the fractions containing a desired compound were collected. The solvent was removed by distillation from the solution under reduced pressure to give methyl 2-(2-oxo-3-phthalimido-1-azetidinyl)-3-phenylthioacrylate (a mixture of trans and cis isomer) (4.23 g.).

This compound was pulverized and recrystallized from ethanol to give one of cis or trans isomers of the object compound (0.84 g.), mp 170° to 171° C.

IR—$\nu cm^{-1}$ (Nujol): 1780, 1760, 1720(shoulder), 1710, 1610.

NMR(TMS)—$\delta ppm(CDCl_3)$: 3.80(3H,s), 4.13(1H,t, J=6Hz), 4.29(1H, d,d, J=6Hz, 3Hz), 5.63(1H, d,d, J=6Hz, 3Hz), 7.3 to 8.0 (10H,m).

EXAMPLE 143

A mixture of D-2-(3-bromo-2-oxo-1-azetidinyl)-2-phenylacetate acid (120 mg.) and sodium azide (114 mg.) in N,N-dimethylformamide (1.2 ml.) was stirred for 3 hours at 70° C. After the solvent was removed by vacuum distillation, the residue was taken up into ethyl acetate (5 ml.) and washed with 3% hydrochloric acid and water. The ethyl acetate layer was then extracted twice with each 3 ml. of saturated aqueous sodium bicarbonate. The aqueous extracts were combined, adjusted to pH 2 with 10% hydrochloric acid and then extracted three times with each 3 ml. of ethyl acetate. The ethyl acetate extracts were combined, dried over magnesium sulfate and evaporated to dryness under reduced pressure. The oily residue was preparatively fractionated by thin layer chromatography on silica gel, developed with a mixture of benzene, ethyl acetate and acetic acid (6:2:1 by volume, respectively) and collected the desired fraction to give D-2-(3-azido-2-oxo-1-azetidinyl)-2-phenylacetic acid, which was identified with the authentic specimen prepared in aforementioned Example 103 by direct comparison of the IR.

EXAMPLE 144

Methyl 2-[4-trans-styryl-2-oxo-3-phthalimido-1-azetidinyl]-2-phenylacetate (a mixture of two cis isomers at the third and fourth positions of the azetidine ring, 13.0 g.) was dissolved in dichloromethane (300 ml.) and ozon gas was absorbed into the solution until the color of ozon was appeared in the mixture at −78° C. in the course of 45 minutes. After nitrogen gas was bubbled into the mixture at the same temperature for half an hour, dimethylsulfide (6.4 ml.) was added thereto and allowed to stand for a while. The reaction mixture was evaporated to dryness under reduced pressure to give a residue, which was dissolved in dichloromethane. The solution was washed twice with water (100 ml.) and an aqueous sodium chloride, and then dried over magnesium sulfate. The solution was evaporated to dryness under reduced pressure to give a residue, which was subjected to column chromatography on alumina (200 g.). Elution was carried out with benzene, and then chloroform and the fractions containing a desired compound were collected. The solvent was removed by distillation under reduced pressure to give methyl 2-(4-formyl-2-oxo-2-phthalimido-1-azetidinyl)-2-phenylacetate (a mixture of two cis isomers at the third and fourth positions of the azetidine ring, 9.14 g.).

IR —$\nu cm^{-1}$ (film): 1785, 1740(shoulder), 1730, 1710(shoulder).

NMR (TMS) —$\delta ppm(CDCl_3)$: 3.80(3H,s), 4.27 and 4.78(1H, each d,d J=4Hz, 6Hz), 5.51 and 5.79(1H, each d, J=6Hz), 5.88 and 5.93 (1H, each s), 7.43(5H,s), 7.64 to 7.94 (4H,m), 8.79 and 9.98(1H, each d, J=4Hz).

EXAMPLE 145

Methyl 2-(4-formyl-2-oxo-3-phthalimido-1-azetidinyl)-2-phenylacetate (390 mg.) and O-benzyl hydroxylamine (170 mg.) were dissolved in dried benzene (10 ml), and the solution was stirred at ambient temperature for 4 hours and then heated at 50° to 60° C. for an hour. The reaction mixture was washed with 1% hydrochloric acid (10 ml.), water and an aqueous sodium chloride and then dried over magnesium sulfate. The solution was evaporated to dryness under reduced pressure to give a residue (560 mg.), which was subjected to column chromatography on silica gel (15 g.). Elution was carried out with chloroform and the fractions containing a desired compound were collected. The solution was removed by distillation from the solution under reduced pressure to give methyl 2-(4-benzyloxyimino-methyl-2-oxo-3-phthalimido-1-azetidinyl)-2-phenylacetate (530 mg.).

IR—$\nu cm^{-1}$ (film): 1790, 1780, 1750(shoulder), 1730.

EXAMPLE 146

A mixture of methyl 2-(3-azido-4-formyl-2-oxo-1-azetidinyl)-2-phenylacetate (2.30 g.), sodium borohydride (310 mg), ethanol (40 ml.) and water (5 ml.) was stirred at −10° to 0° C. for an hour. The reaction mixture was adjusted to pH 4 to 5 with 10% hydrochloric acid at the same temperature, whereafter the ethanol was removed by distillation from the solution to give an aqueous residue, to which sodium chloride was added. The resultant solution was extracted twice with chloroform and the extract was washed with an aqueous sodium chloride. After drying the solution over magnesium sulfate, the solution was evaporated to dryness under reduced pressure to give a residue(2.02 g.), which was subjected to column chromatography on alumina(20 g.). Elution was carried out with chloroform and the fractions containing a desired compound were collected. The solvent was removed by distillation under reduced pressure to give methyl 2-(3-azido-4-hydroxymethyl-2-oxo-1-azetidinyl)-2-phenylacetate(0.95 g.).

IR—$\nu cm^{-1}$(film): 3450, 2130, 1780(shoulder), 1770, 1740.

EXAMPLE 147

A mixture of methyl 2-(4-formyl-2-oxo-3-phthalimido-1-azetidinyl)-2-phenylacetate (0.38 g.), silver oxide(0.92 g), tetrahydrofuran (9 ml.) and water (1 ml.) was stirred at ambient temperature for 40 hours. The insoluble materials were filtered off from the reaction mixture and the tetrahydrofuran was removed by distillation from the filtrate under reduced pressure. Water was added to the resultant residue and adjusted to pH 2 with 10% hydrochloric acid, whereafter the mixture was extracted with ethyl acetate. The extract was washed with 1% Aqueous sodium bicarbonate, and the washings were adjusted to pH 2 with 10% hydrochloric acid. The aqueous solution was extracted with ethyl acetate, whereafter this extract and the above-obtained extract were combined, washed with water and then dried over magnesium sulfate. The solvent was removed by distillation from the solution under reduced pressure to give methyl 2-(4-carboxy-2-oxo-3-phthalimido-1-azetidinyl)-2-phenylacetate [a mixture of two cis isomers (a) and (b) at the third and fourth positions of the azetidine ring, (200 mg.)].

IR—$\nu cm^{-1}$(film): 2600 to 2500, 1770, 1760, 1740 to 1720.

| NMR (TMS) ppm[(CD$_3$)$_2$CO]: Isomer (a): | Isomer (b): |
|---|---|
| 3.66(3H, s) | 3.69(3H, s) |
| 4.89(1H,d, J=5Hz) | 4.78(1H,d, J=5Hz) |
| 5.59(1H, s) | 5.56(1H, s) |
| 5.89(1H,d, J=5Hz) | 5.79(1H,d, J=5Hz) |
| 7.28 to 7.70(5H, m) | 7.28 tp 7.70(5H, m) |
| 7.80 to 8.54(4H, m) | 7.80 to 8.54(4H, m) |

The following compounds (Examples 148 to 150) were obtained in substantially the same manner as described in Example 30.

EXAMPLE 148

Methyl D-2-(3-amino-2-oxo-4-phenyl-1-azetidinyl)-2-(4-hydroxyphenyl)acetate (3-α-4-α-configuration of the azetidine ring).

IR—$\nu cm^{-1}$ (Nujol): 3250, 1745, 1735 (shoulder).

NMR (TMS)—δppm (CDCl$_3$): 3.73 (3H, s), 4.52 (1H,d,J=6 Hz), 5.13 (1H,d,J=6 Hz), 5.37 (1H, s), 6.47 to 7.34 (9H, m).

EXAMPLE 149

Methyl D-2-(3-amino-2-oxo-4-phenyl-1-azetidinyl)-2-(4-hydroxyphenyl)acetate (3-β-4-β-configuration of the azetidine ring).

IR—$\nu cm^{-1}$ (film): 3300, 1750, 1730.

NMR (TMS)—δppm (CDCl$_3$): 3.48 (2H, broad s), 3.58 (3H, s), 4.21 (1H,d,J=6 Hz), 4.78 (1H,d,J=6 Hz), 5.20 (1H, s), 6.70 (2H,d,J=10 Hz), 7.08 (2H,d,J=10 Hz), 7.16 to 7.52 (5H, m).

EXAMPLE 150

Methyl D-2-(3-amino-4-hydroxymethyl-2-oxo-1-azetidinyl)-2-phenylacetate (a mixture of two cis isomers at the third and fourth positions of the azetidine ring).

IR—$\nu cm^{-1}$ (film): 3400, 1760, 1740.

The following compounds (Example 151 and 152) were obtained by reacting 3-amino-2-azetidinone compound with 2-(2,2-dichloroacetoxyimino)-2-phenylacetic acid in substantially the same manner as described in Example 79.

EXAMPLE 151

Methyl D-2-[3-(2-hydroxyimino-2-phenylacetamido)-2-oxo-4-phenyl-1-azetidinyl]-2-(4-hydroxyphenyl)acetate (3-α-4-α-configuration of the azetidine ring), mp 209° to 211° C.

IR—$\nu cm^{-1}$ (Nujol): 3270, 1765, 1735, 1645.

EXAMPLE 152

Methyl D-2-[3-(2-hydroxyimino-2-phenylacetamido)-2-oxo-4-phenyl-1-azetidinyl]-2-(4-hydroxyphenyl)acetate (3-β-4-βconfiguration of the azetidine ring), mp 191° to 192.5° C.

IR—$\nu cm^{-1}$ (Nujol): 3350, 3280, 1740, 1710, 1670.

NMR (TMS)—δppm [(CD$_3$)$_2$SO]: 3.56 (3H, s), 4.95 (1H,d,J=6 Hz), 5.28 (1H, s), 5.38 (1H,d,d,J=6, 8 Hz), 6.48 to 7.56 (14H, m), 9.40 (1H,d,J=8 Hz), 9.54 (1H, s).

The following compounds (Example 153) was obtained by subjecting the corresponding compound having methyl ester bond to hydrolysis in substantially the same manner as one described in Example 110.

EXAMPLE 153

2-[3-(2-Hydroxyimino-2-phenylacetamido)-2-oxo-4-phenyl-1-azetidinyl]-2-(4-hydroxyphenyl)acetic acid (cis isomer at the third and fourth position of the azetidine ring).

IR—$\nu cm^{-1}$ (Nujol): 3260, 1735 (shoulder), 1710, 1650.

IR—$\nu cm^{-1}$ (Nujol): 3260, 1735 (shoulder), 1710, 1650.

What we claim is:

1. A compound of the formula:

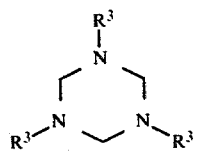

wherein R$^3$ is a group of the formula:

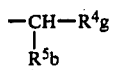

in which
$R_g^4$ is hydrogen;
phenyl which may have at least one suitable substituent selected from groups consisting of $C_1$-$C_3$ alkanesulfonamido, phenyl ($C_1$-$C_4$)alkoxy, phenyl ($C_1$-$C_2$) alkoxycarbonyloxy, phenacyloxy and nitro;
naphthyl;
phenyl ($C_1$-$C_5$)alkyl having at least one suitable substituent selected from groups consisting of $C_1$-$C_5$ alkoxy in the alkyl moiety thereof and phenyl ($C_1$-$C_4$)alkoxy in the phenyl ring thereof;
phenylthio($C_1$-$C_5$)alkyl;
thienyl;
or furyl; and
$R_b^5$ is carboxy or its ester selected from groups consisting of $C_1$-$C_5$ alkoxycarbonyl, phenyl($C_1$-$C_2$)alkoxycarbonyl, phenacyloxycarbonyl or $C_1$-$C_5$ alkyl having $C_1$-$C_5$ alkoxycarbonyl.

2. A compound according to claim 1, wherein $R_g^4$ is hydrogen, and $R_b^5$ is $C_1$-$C_5$alkoxycarbonyl or phenyl($C_1$-$C_2$)alkoxycarbonyl.

3. A compound according to claim 2, wherein $R_b^5$ is methoxycarbonyl, ethoxycarbonyl, or benzyloxycarbonyl.

4. A compound according to claim 1, wherein $R_g^4$ is phenyl which may have at least one suitable substituent selected from groups consisting of $C_1$-$C_3$ alkanesulfonamido, phenyl ($C_1$-$C_4$)alkoxy, phenyl ($C_1$-$C_2$) alkoxycarbonyloxy, phenacyloxy and nitro.

5. A compound according to claim 4, wherein $R_g^4$ is phenyl, and $R_b^5$ is $C_1$-$C_5$alkoxycarbonyl or phenyl($C_1$-$C_2$)alkoxycarbonyl.

6. A compound according to claim 5, wherein $R_b^5$ is methoxycarbonyl, or benzyloxycarbonyl.

7. A compound according to claim 4, wherein $R_g^4$ is phenyl, and $R_b^5$ is $C_1$-$C_5$alkyl having $C_1$-$C_5$alkoxycarbonyl.

8. A compound according to claim 7, wherein $R_b^5$ is methoxycarbonylmethyl.

9. A compound according to claim 4, wherein $R_g^4$ is $C_1$-$C_3$alkanesulfonamidophenyl, and $R_b^5$ is $C_1$-$C_5$ alkoxycarbonyl.

10. A compound according to claim 9, wherein $R_g^4$ is methanesulfonamidophenyl.

11. A compound according to claim 10, wherein $R_g^4$ is 3-methanesulfonamidophenyl, and $R_b^5$ is methoxycarbonyl.

12. A compound according to claim 4, wherein $R_g^4$ is phenyl ($C_1$-$C_4$)alkoxyphenyl, and $R_b^5$ is $C_1$-$C_5$alkoxycarbonyl or phenyl ($C_1$-$C_2$)alkoxycarbonyl.

13. A compound according to claim 12, wherein $R_g^4$ is benzyloxyphenyl.

14. A compound according to claim 13, wherein $R_g^4$ is 4-benzyloxyphenyl, and $R_b^5$ is methoxycarbonyl, or benzyloxycarbonyl.

15. A compound according to claim 4, wherein $R_g^4$ is phenyl ($C_1$-$C_2$)alkoxycarbonyloxyphenyl, and $R_b^5$ is $C_1$-$C_5$alkoxycarbonyl.

16. A compound according to claim 15, wherein $R_g^4$ is benzyloxycarbonyloxyphenyl.

17. A compound according to claim 16, wherein $R_g^4$ is 4-benzyloxycarbonyloxyphenyl, and $R_b^5$ is methoxycarbonyl.

18. A compound according to claim 4, wherein $R_g^4$ is phenacyloxyphenyl, and $R_b^5$ is phenacyloxycarbonyl.

19. A compound according to claim 18, wherein $R_g^4$ is 4-phenacyloxyphenyl.

20. A compound according to claim 4, wherein $R_g^4$ is nitrophenyl, and $R_b^5$ is $C_1$-$C_5$alkoxycarbonyl.

21. A compound according to claim 20, wherein $R_g^4$ is 3-nitrophenyl, and $R_b^5$ is methoxycarbonyl.

22. A compound according to claim 1, wherein $R_g^4$ is naphthyl, and $R_b^5$ is $C_1$-$C_5$alkoxycarbonyl.

23. A compound according to claim 22, wherein $R_g^4$ is 1-naphthyl, and $R_b^5$ is methoxycarbonyl.

24. A compound according to claim 1, wherein $R_g^4$ is phenyl ($C_1$-$C_5$)alkyl having at least one substituent selected from groups consisting of $C_1$-$C_5$ alkoxy in the alkyl moiety thereof and phenyl ($C_1$-$C_4$) alkoxy in the phenyl ring thereof, and $R_b^5$ is $C_1$-$C_5$ alkoxycarbonyl.

25. A compound according to claim 24, wherein $R_g^4$ is phenyl ($C_1$-$C_5$)alkyl having $C_1$-$C_5$ alkoxy in the alkyl moiety thereof.

26. A compound according to claim 25, wherein $R_5^4$ is α-methoxybenzyl, and $R_b^5$ is methoxycarbonyl.

27. A compound according to claim 24, wherein $R_5^4$ is phenyl ($C_1$-$C_5$)alkyl having phenyl ($C_1$-$C_4$)alkoxy in the phenyl ring thereof.

28. A compound according to claim 27, wherein $R_g^4$ is benzyloxybenzyl.

29. A compound according to claim 28, wherein $R_g^4$ is 4-benzyloxybenzyl, and $R_b^5$ is methoxycarbonyl.

30. A compound according to claim 1, wherein $R_g^4$ is phenylthio ($C_1$-$C_5$)alkyl, and $R_b^5$ is $C_1$-$C_5$alkoxycarbonyl.

31. A compound according to claim 30, wherein $R_g^4$ is phenylthiomethyl, and $R_b^5$ is methoxycarbonyl.

32. A compound according to claim 1, wherein $R_g^4$ is furyl, and $R_b^5$ is $C_1$-$C_5$ alkoxycarbonyl.

33. A compound according to claim 32, wherein $R_g^4$ is 2-furyl, and $R_b^5$ is methoxycarbonyl.

34. A compound according to claim 1, wherein $R_g^4$ is thienyl, and $R_b^5$ is $C_1$-$C_5$ alkoxycarbonyl.

35. A compound according to claim 34, wherein $R_g^4$ is 2-thienyl, and $R_b^5$ is methoxycarbonyl.

* * * * *

UNITED STATES PATENT AND TRADEMARK OFFICE
CERTIFICATE OF CORRECTION

PATENT NO. : 4,181,800

DATED : January 1, 1980

INVENTOR(S) : Takashi Kamiya et al.

It is certified that error appears in the above-identified patent and that said Letters Patent are hereby corrected as shown below:

```
Col. 12, line 65, "organic" should read --inorganic--.
Col. 14, line 17, "tolymesyl" should read --tolylmesyl--.
Col. 15, line 64, "unsabstituted" should read --unsubstituted--.
Col. 17, line 1, insert "aryl" after "heterocyclic-alkyl,".
Col. 19, line 4, "[R¹]" should read --[R²]--.
Col. 19, line 57, "lease" should read --least--.
Col. 40, line 2, "bellow" should read --below--.
Col. 40, line 25, "112" should be immediately below "108" and on
         line with "Staphlococcus aureaus  3.75".
Col. 40, line 54, before "included", "in" should read --is--.
Col. 43, line 3, "(6L H," should read --(6H, --.
Col. 50, line 7, Example 19, "7,38" should read --7.38--.
Col. 51, line 45, "thid" should read --third--.
Col. 55, lines 20-27, the formula should read:
```

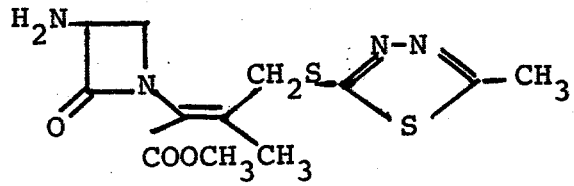

```
Col. 56, line 43, "Гppm" should read --δppm--.
Col. 57, line 54, "(time-" should read -- (trime- --.
Col. 58, line 31, "acrylating" should read --acylating--.
Col. 58, line 53, after "3250" insert a --,--.
Col. 67, line 63, cancel "and" (first occurrence).
Col. 69, line 55, cancel "p".
```

UNITED STATES PATENT AND TRADEMARK OFFICE
CERTIFICATE OF CORRECTION

PATENT NO. : 4,181,800
DATED : January 1, 1980
INVENTOR(S) : Takashi Kamiya et al.

It is certified that error appears in the above-identified patent and that said Letters Patent are hereby corrected as shown below:

Col. 12, line 65, "organic" should read --inorganic--.
Col. 14, line 17, "tolymesyl" should read --tolylmesyl--.
Col. 15, line 64, "unsabstituted" should read --unsubstituted--.
Col. 17, line 1, insert "aryl" after "heterocyclic-alkyl,".
Col. 19, line 4, "[$R^1$]" should read --[$R^2$]--.
Col. 19, line 57, "lease" should read --least--.
Col. 40, line 2, "bellow" should read --below--.
Col. 40, line 25, "112" should be immediately below "108" and on line with "Staphlococcus aureaus  3.75".
Col. 40, line 54, before "included", "in" should read --is--.
Col. 43, line 3, "(6L H," should read --(6H, --.
Col. 50, line 7, Example 19, "7,38" should read --7.38--.
Col. 51, line 45, "thid" should read --third--.
Col. 55, lines 20-27, the formula should read:

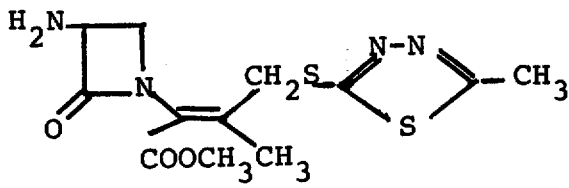

Col. 56, line 43, "Γppm" should read --δppm--.
Col. 57, line 54, "(time-" should read -- (trime- --.
Col. 58, line 31, "acrylating" should read --acylating--.
Col. 58, line 53, after "3250" insert a --,--.
Col. 67, line 63, cancel "and" (first occurrence).
Col. 69, line 55, cancel "p".

UNITED STATES PATENT AND TRADEMARK OFFICE
CERTIFICATE OF CORRECTION

PATENT NO. : 4,181,800

DATED : January 1, 1980

INVENTOR(S) : Takashi Kamiya et al.

It is certified that error appears in the above-identified patent and that said Letters Patent are hereby corrected as shown below:

Col. 72, line 41, "mono-" should read -- iso- --.
Col. 73, lines 61-62, "discribed" should read --described--.
Col. 77, line 52, "ppm" should read --δppm--.
Col. 78, cancel lines 56 and 57.

Signed and Sealed this

First Day of July 1980

[SEAL]

Attest:

SIDNEY A. DIAMOND

Attesting Officer

Commissioner of Patents and Trademarks